US008409795B2

(12) United States Patent
Schneider et al.

(10) Patent No.: US 8,409,795 B2
(45) Date of Patent: Apr. 2, 2013

(54) SELEX AND PHOTOSELEX

(75) Inventors: Daniel J. Schneider, Arvada, CO (US);
Sheri K. Wilcox, Longmont, CO (US);
Dominic Zichi, Boulder, CO (US); Dan Nieuwlandt, Longmont, CO (US); Jeff Carter, Longmont, CO (US); Larry Gold, Boulder, CO (US)

(73) Assignee: Somalogic, Inc., Boulder, CO (US)

(*) Notice: Subject to any disclaimer, the term of this patent is extended or adjusted under 35 U.S.C. 154(b) by 535 days.

(21) Appl. No.: 12/175,388

(22) Filed: Jul. 17, 2008

(65) Prior Publication Data

US 2009/0098549 A1     Apr. 16, 2009

Related U.S. Application Data

(60) Provisional application No. 60/950,281, filed on Jul. 17, 2007, provisional application No. 60/950,293, filed on Jul. 17, 2007, provisional application No. 60/950,283, filed on Jul. 17, 2007, provisional application No. 61/031,420, filed on Feb. 26, 2008, provisional application No. 61/051,594, filed on May 8, 2008.

(51) Int. Cl.
*C12Q 1/68* (2006.01)
(52) U.S. Cl. ............ 435/6; 435/325; 435/375; 536/24.5; 536/24.31; 536/24.1
(58) Field of Classification Search ................. None
See application file for complete search history.

(56) References Cited

U.S. PATENT DOCUMENTS

| | | | |
|---|---|---|---|
| 4,683,195 A | 7/1987 | Mullis | |
| 4,753,983 A | 6/1988 | Ngo | |
| 5,035,996 A | 7/1991 | Hartley | |
| 5,270,163 A | 12/1993 | Gold et al. | |
| 5,472,841 A | 12/1995 | Jayasena et al. | |
| 5,475,096 A | 12/1995 | Gold et al. | |
| 5,610,287 A | 3/1997 | Nikiforov et al. | |
| 5,639,868 A | 6/1997 | Janjic et al. | |
| 5,645,985 A | 7/1997 | Froehler | |
| 5,705,337 A | 1/1998 | Gold et al. | |
| 5,723,323 A | 3/1998 | Kauffman et al. | |
| 5,737,498 A | 4/1998 | Murray | |
| 5,763,177 A | 6/1998 | Gold et al. | |
| 5,866,336 A | 2/1999 | Nazarenko et al. | |
| 5,874,218 A | 2/1999 | Drol et al. | |
| 5,945,527 A * | 8/1999 | Tu et al. | 536/27.6 |
| 5,962,219 A | 10/1999 | Gold et al. | |
| 5,962,225 A * | 10/1999 | Ramberg | 435/6 |
| 5,985,548 A | 11/1999 | Collier et al. | |
| 5,998,142 A | 12/1999 | Gold et al. | |
| 6,001,577 A | 12/1999 | Gold et al. | |
| 6,020,130 A | 2/2000 | Gold et al. | |
| 6,083,696 A * | 7/2000 | Biesecker et al. | 435/6.11 |
| 6,235,471 B1 | 5/2001 | Knapp et al. | |
| 6,291,184 B1 | 9/2001 | Gold et al. | |
| 6,458,539 B1 | 10/2002 | Gold et al. | |
| 6,482,594 B2 | 11/2002 | Gold et al. | |
| 2003/0054360 A1 * | 3/2003 | Gold et al. | 435/6 |
| 2004/0106145 A1 | 6/2004 | Gold et al. | |
| 2004/0132067 A1 | 7/2004 | Gold et al. | |

FOREIGN PATENT DOCUMENTS

| | | |
|---|---|---|
| AU | 692469 | 11/1998 |
| GB | 2 183 661 A | 6/1987 |
| WO | WO 89/06694 | 7/1989 |
| WO | WO 91/19813 | 12/1991 |
| WO | WO 92/06380 | 4/1992 |
| WO | WO 92/14843 | 9/1992 |
| WO | WO 93/05182 | 3/1993 |
| WO | WO 95/07364 | 3/1995 |
| WO | WO 95/08003 | 3/1995 |
| WO | WO 02/077262 | 10/2002 |
| WO | WO 03/014369 | 2/2003 |
| WO | WO 2004/024950 | 3/2004 |

OTHER PUBLICATIONS

Allen et al. (1991) J. Biol. Chem. 266(10):6113-6119, "Identification of Amino Acids in *lac* Repressor Protein Cross-linked to Operator DNA Specifically Substituted with Bromodeoxyuridine".
Barbier et al. (1984) Biochemistry 23:2933, Photochemical crosslinking of *lac* repressor to nanoperator 5-bromouracil-substituted DNA.
Bartel and Szostak (Sep. 10, 1993) Science 261:1411-1418, "Isolation of New Ribozymes from a Large Pool of Random Sequences".
Bayley et al. (1977) Methods in Enzymology 46:69, "Photoaffinity Labeling".
Beaudry et al. (Jul. 31, 1992) Science 257:635-641, "Directed Evolution of an RNA Enzyme".
Beckett et al. (1988) J. Mol. Biol. 204:939-947, "Roles of Operator and Non-Operator RNA Sequences in Bacteriophage R17 Capsid Assembly".
Blatter et al.. (Oct. 1992) Nature 359:650-653, "Identification of an amino acidbase contact in the GCN4-DNA complex by bromouracil-mediated photocrosslinking".
Carey et al.. (1983) Biochemistry 22:4723, "Sequence-Specific Interaction of R17 Coat Protein with Its Ribonucleic Acid Binding Site".
Chen et al. (1977) Biochemistry 16(15):3310-3315, "Kinetic and Photochemical Studies and Alteration of Ultraviolet Sensitivity of *Escherichia coli* Thymidine Kinase by Halogenated Allosteric Regulators and Substrate Analogues".

(Continued)

*Primary Examiner* — Kimberly Chong
(74) *Attorney, Agent, or Firm* — Swanson & Bratschun, L.L.C.

(57) ABSTRACT

The present disclosure describes improved SELEX methods for generating nucleic acid ligands that are capable of binding to target molecules and improved photoSELEX methods for generating photoreactive nucleic acid ligands that are capable of both binding and covalently crosslinking to target molecules. The disclosure further describes nucleic acid libraries having expanded physical and chemical properties and their use in SELEX and photoSELEX; methods for increasing the crosslinking efficiencies of photoaptamers; methods for producing photoaptamers having selective modifications that enhance functionality and minimize non-specific photoreactions; and methods for generating truncated nucleic acid ligands from nucleic acid ligands of longer length. The disclosure further describes aptamers and photoaptamers obtained by using any of the foregoing.

13 Claims, 25 Drawing Sheets

OTHER PUBLICATIONS

Crameri et al. (1993) Nucleic Acid Research 21:4410, "10(20)-fold aptamer library amplification without gel purification".
Czarnecki et al. (1979) Methods in Enzymology 56:642-651, "Synthesis and Use of Azido Photoaffinity Analogs of Adenine and Guanine Nucleotides".
Dietz et al. (1987) J. Am. Chem. Soc. 109:1793, "Photochemical coupling of 5 bromouracil BU to a peptide linkage a model for BU DNA protein".
Dietz et al. (1987) Photochem. & Photobiol. 46(6):971-978, "Photochemical Coupling of 5-Bromouracil to Tryptophan, Tyrosine and Histidine, Peptidelike Derivatives in Aqueous Fluid Solution".
Dietz et al. (1989) Photochem. & Photobiol. 49(2):121-129, "Photochemical Reduction of 5-Bromouracil by Cysteine Derivatives and Coupling of 5-Bromouracil to Cystine Derivatives".
Eggen et al. (1969) J. Mol. Biol. 39:293-305, "Regulation of Protein Synthesis Directed by Coliphage MS2 RNA".
Ellington & Szostak (1990) Abstracts presented at Cold Spring Harbor, NY: Meeting on RNA Processing, p. 84.
Evans et al. (1989) Biochemistry 28:713-720, "Photoaffinity labeling of Terminal Deoxynucleotidyl Transferase. 2. Identification of Peptides in the Nucleotide Binding Domain".
Expert-Bezacon et al. (Jan. 1980) European Journal of Biochemistry, 103(2):365-375, "Synthesis and properties of N-acetyl-N'-(p-glyocylylbenzoyl) cystamine, a new reagent for RNA-RNA and RNA-protein cross-linking".
Farrar et al. (1991) Biochemistry 30:3075, "Interactions of photoactive DNAs with terminal deoxynucleotidyl transferase: Identification of peptides in the DNA binding domain".
Favre (1990) Bioorganic Chemistry, vol. 1, Chapter 5, p. 379-425, "4-Thiouridine as an Intrinsic Photoaffinity Probe of Nucleic Acid Structure and Interactions".
Gott et al. (1991) Biochemistry 30:6290, "A Specific, UV-induced RNA-protein cross-link using 5-Bromouridine-substituted RNA".
Grobe et al. (1988) Nucleic Acid Research 16(24):11725-11734, "Characterization of RNA hairpin loop stability".
Hanna et al. (1993) Nucleic Acid Research 21(9):2073-2079, "Synthesis and characterization of a new photocrosslinking CTP analog and its use in photoaffinity labeling *E.coli* and T7 RNA polymerases".
Hutchinson et al. (1980) Prog. In Sucell Biol. 7:1, "The Photochemistry of 5-Bromouracil and 5-Iodouracil in DNA".
Ito et al. (1980) J. Am. Chem. Soc. 102(25):7535-7541, "Acetone-Sensitized Photocoupling of 5-Bromouridine to Tryptophan Derivatives via Electron-Transfer Process".
Ito et al. (1980) Photochemistry and Photobiology 32:683-685, "Photochemical Addition of L-Lysine 1,3-Dimethyl-4-Thiouracil".
Jensen et al. (1995) Proc. Natl. Acad. Sci. 92:1220, "Using in vitro selection to direct the covalent attachment of human immunodeficiency virus type 1 Rev protein to high-affinity RNA ligands".
Joyce (1989) Gene 82:83-87, "Amplication, Mutation and Selection of Catalytic RNA".
Joyce (1989) Nucleic Acids Research 17(2):711-722, "A novel technique for the rapid preparation of mutant RNA's".
Katouzian-Safadi et al. (1991) Nucleic Acid Research 19:4937, "Determination of the DNA-Interacting Region of the Archaebacterial Chromosomal Protein MC1. Photocrosslinks with 5-Bromouracil-Susbtituted DNA".
Katouzian-Safadi et al. (1991) Photochemistry and Photobiology 53:(5)611-615, "Photochemical Cross-Linking of the Cyclic Adenosine 3',5' Monophosphate Receptor Protein to *Escherichia coli* 5-Bromouracil Protein to *Escherichia coli* 5-Bromouracilsubstituted DNA Role of the Effectors".
Khalili et al. (1988) The EMBO Journal 7(4):1205-1210, "Nuclear factors in human brain cells bind specifically to the JCV regulatory region".
Kinzler et al. (1989) Nucleic Acids Research 17:3645-3653, "Whole genome PCR: application to the identification of sequences bound by gene regulatory proteins".
Kramer et al. (1974) J. Mol. Biol. 89:719-736, "Evolution in vitro: Sequence and Phenotype of a Mutant RNA Resistant to Ethidium Bromide".
Lee et al. (Sep. 1991) J. of Biological Chemistry 266(25):16478-16584, "Contacts between 5 S DNA and *Xenopus* TFIIIA Identified Using 5-Azido-2'-deoxyuridine-substituted DNA".
Lehman et al. (Jan. 1993) Nature 361:182-185, "Evolution in vitro of an RNA enzyme with altered metal independence".
Levisohn & Spiegelman (1968) Proc. Natl. Acad. Sci. 60:866-872, "The cloning of a self replication RNA molecule".
Levisohn & Spiegelman (1969) Proc. Natl. Acad. Scie. 63:805-811, "Further Extracellular Darwinian Experiments with Replicating RNA Molecules Diverse Variants Isolated under Different Selective Conditions".
Lin et al. (Mar. 1974) Proc. Natl. Acad. Sci. 71(3):947-951, "Photochemical Attachment of *lac* Repressor to Bromodcoxyuridine Substituted *lac* Operator by Ultraviolet Radiation".
Ling et al. (1970) Virology 40:920-929, "Independent Assembly of Qβ and MS2 Phages in Doubly Infected *Escherichia coli*".
Liu et al. (1992) Tetrahedron Letters 33(30):4265-4268, "Synthesis of Photoactive DNA: Incorporation of 8•Bromo-2'-Deoxyadenosine into Synthetic Oligonucleotides".
Mee (1987) Radiation Chemistry: Principles and Applications, Ch. 16 p. 477-499, "Radiation Chemistry of Biopolymers".
Milligan et al. (1987) Nucleic Acid Research 15(21):8783-8798, "Oligoribonucleotide synthesis using T7 RNA polymerase and synthetic DNA templates".
OA issued Apr. 30, 2008 in U.S. Appl. No. 10/681,882.
OA issued Jan. 8, 2007 in U.S. Appl. No. 10/681,882.
OA issued Jun. 27, 2006 in U.S. Appl. No. 10/681,882.
OA issued Jun. 29, 2005 in U.S. Appl. No. 10/681,882.
OA issued Sep. 20, 2007 in U.S. Appl. No. 10/681,882.
Office Action issued Apr. 9, 2003 in U.S. Appl. No. 09/723,718.
Office Action issued Jun. 13, 2002 in U.S. Appl. No. 09/723,718.
Office Action issued Jun. 6, 2001 in U.S. Appl. No. 09/723,718.
Office Action issued Jan. 15, 2002 in U.S. Appl. No. 09/882,246.
Office Action issued Mar. 3, 1995 in U.S. Appl. No. 08/123,935.
Office Action issued May 31, 1994 in U.S. Appl. No. 08/123,935.
Office Action issued Nov. 8, 1996 in U.S. Appl. No. 08/443,959.
Office Action issued Sep. 10, 1995 in U.S. Appl. No. 08/443,959.
Office Action issued Mar. 28, 1997 in U.S. Appl. No. 08/612,895.
Ogata et al. (Nov. 1977) Proc. Natl. Acad. Sci. 74(11):4973-4976, "Contacts between the *lac* repressor and thymines in the *lac* operator".
Oliphant et al. (1986) Gene 44:177-183, "Cloning of random sequence oligodeoxynucleotides".
Oliphant et al. (1987) Methods in Enzymology 155:568-582, "The use of random-sequence oligonucleotides for determining consensus sequences".
Oliphant et al. (1988) Nucleic Acids Research 16(15):7373-7683, "Defining the consensus sequences of I promoter elements by random selection".
Oliphant et al. (1989) Mol. Cell. Biol. 9:2944-2949, "Defining the Sequence Specificity of DNA-Binding Proteins by Selecting Binding Sites from Random-Sequence Oligonucleotides: Analysis of Yeast GCN4 Protein".
Rahn et al. (1979) Photochemistry and Photobiology 30:449-454, "Photochemistry of DNA Containing Iodinated Cytosine".
Rahn et al. (1982) Photochemistry and Photobiology 35:459-465, "Action Spectra for the Photolysis of 5-Iododeoxyuridine in DNA and Related Model Systems: Evidence for Short-Range Energy Transfer".
Robertson et al. (Mar. 1990) Nature 344:467-468, "Selection in vitro of an RNA enzyme that specifically cleaves single-stranded DNA".
Rothman et al. (1967) Photochemistry and Photobiology 6:775-778, "Triplet States of Bromouracil and Iodouracil".
Saito et al. (1986) J. Org. Chem. 51:5148-5153, "Photochemistry of 5- and 6-Iodouracils in the Presence of Allylsilanes and Alkenes. A Convenient Route to C5- and C6-Substituted Uracils".
Saito et al. (1990) Bioorganic Photochemistry 3:317-340, "Photoreactions of Nucleic Acids and Their Constituents with Amino Acids and Related Compounds".

Salvucci et al. (1990) Planta 181:287-295, "Photoaffinity labeling or ribulose-bisphosphate carboxylase/oxygenase with 8-azidoadenosis 5'-triphophate".

Schneider et al. (1992) J. Mol. Biol. 228:862-869, "Selection of High Affinity RNA Ligands to the Bacteriophage R17 Coat Protein".

Shetlar (1980) Photochemistry and Photobiology 5:105, "Cross-linking of proteins to nucleic acids by ultraviolet light".

Sperling et al. (1980) Annals of the New York Academy of Sciences, 346:386-388, "Photochemical cross-linking between proteins and nucleic acids as a probe of nucleoprotein interactions".

Sugiyama et al. (1993) J. Am. Chem. Soc. 115:4443-4448, Photoinduced Deoxyribose C2' Oxidation in DNA. Alkali-Dependent Cleavage of Erythrose-Containing Sites via a Retroaldol Reaction.

Szostak (1988) "Structure and Activity of Ribozymes," in *Redesigning the Molecules of Life*, (S.A. Benner ed.) Springer-Verlag Berline Heidelberg, pp. 87-113.

Szybalski (Jul./Aug. 1974) Cancer Chemotherapy Reports 58(4):539-557, "X-Ray Sensitization by Halopyrimidines".

Talbot et al. (1990) Nucleic Acids Research 18(12):3521-3528, "Use of synthetic oligoribonucleotides to probe RNA—protein interactions in the MS2 translational operator complex".

Tanner et al. (1988) Biochemistry 27:8852-8861, "Binding Interactions between Yeast tRNA Ligase and a Precursor Transfer Ribonucleic Acid Containing Two Photoreactive Uridine Analogues".

Thiesen et al. (1990) Nucleic Acid Research 18(11):3203-3209, "Target Detection Assay (TDA): a versatile procedure to determine DNA binding sites as demonstrated on SP1 protein".

Tuerk et al. (1990) Science 249:505-510, "Systematic Evolution of Ligands by Exponential Enrichment: RNA Ligands to Bacteriophage T4 DNA Polymerase".

Van Houton (Oct. 1986) Journal of Biological Chemistry 261(30):14135-14141, "Construction of DNA Substrates Modified with Psoralen at a Unique Site and Study of the Action Mechanism of ABC Excinuclease on These Uniformly Modified Substrates".

Weber (1967) Biochemistry 6:3144-3154, "Amino Acid Sequence Studies on the Tryptic Peptides of the Coat Protein of the Bacteriophage R17".

Weintraub (1973) Cold Spring Harbor Symposium on Quantum Biol. 38:247, "The assembly of newly replicated DNA into chromatin".

Wick et al. (Apr. 1991) J. of Biol. Chem. 266(10):6106-6112, "Interactions between *lac* Repressor Protein and Site-specific Bromodeoxyuridine-substituted Operator DNA".

Wolfes et al. (1986) Eur. J. Biochem. 159:267-273, "Cross-linking of bromodeoxyuridine-substituted oligonucleotides to the *Eco*RI and *Eco*RV restriction endonucleases".

Wower et al. (1988) Biochemistry 27:8114-8121, "Photochemical Cross-Linking of Yeast tRNA$^{Phe}$ Containing 8-Azidoadenosine at Positions 73 and 76 to the *Escherichia coli* Ribosome".

Wower et al. (1989) Biochemistry 28:1563-1567, "Photochemical Labeling of Bovine Pancreatic Ribonuclease A with 8-Azidoadenosine 3',5'-Bisphosphate".

Wyatt et al. (1992) Genes & Development 6:2542-2553, "Site-specific cross-linking of mamlualian U5 snRNP to the 5' splice site before the first step of pre-mRNA splicing".

IPRP issued Jan. 19, 2010 in PCT/US2008/070371.

ISR and Written Opinion mailed Dec. 12, 2008 in PCT/US2008/070371.

Vaught, Jonathan David, Thesis Oct. 2008, "Enhancing the Functionality of Nucleic Acids".

European Search Report issued Dec. 29, 2009 in EP application serial No. 08781998.3.

European Search Report issued Apr. 1, 2011 in EP application serial No. 10176864.6.

European Partial Search Report issued Oct. 24, 2012 in EP application serial No. 12160299.9.

\* cited by examiner

Figure 2A
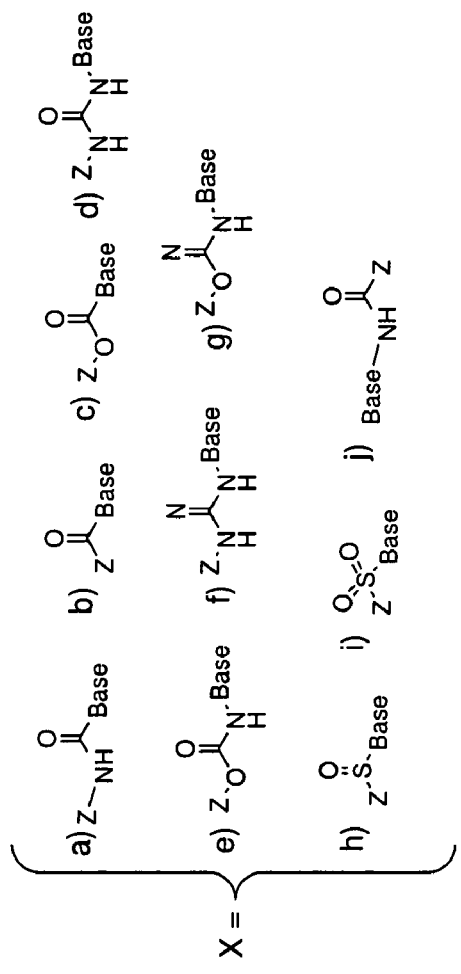
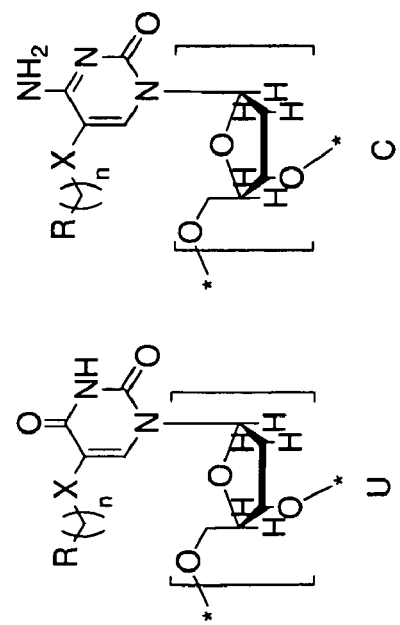

* Denotes point of attachment of the R group to (CH₂)ₙ

Template 1

5'- ABABCCCGCTCGTCGTCTG-(N)$_{40}$-CAGGCAGACGGTCACTC - 3'   (SEQ ID NO: 1)

Forward BrdU Primer 1

5'- BrdU - ATATATATGAGTGACCGTCTGCCTG - 3'   (SEQ ID NO: 2)

Forward ANA Primer 1

5'- ANA - ATATATATGAGTGACCGTCTGCCTG - 3'   (SEQ ID NO: 2)

Forward AQ Primer 1

5'- AQ - ATATATATGAGTGACCGTCTGCCTG - 3'   (SEQ ID NO: 2)

Forward Psor Primer 1

5'- Psor - ATATATATGAGTGACCGTCTGCCTG - 3'   (SEQ ID NO: 2)

Forward PCR Primer 1

5'- ATATATATGAGTGACCGTCTGCCTG - 3'   (SEQ ID NO: 3)

Reverse Primer 1

5'- TTTTTTTTCCCGCTCGTCGTCTG - 3'   (SEQ ID NO: 4)

Reverse PCR Primer 1

5'- ABABTTTTTTTCCCGCTCGTCGTCTG - 3'   (SEQ ID NO: 5)

Figure 3A

Template 2

5'- ABABGTGTCTGTCTGTGTCCTC-(N)$_{40}$-GGTGGAGTGTGGTGAGG - 3'   (SEQ ID NO: 6)

Forward BrdU Primer 2

5'- BrdU - ATATATATCCTCACCACACTCCACC - 3'          (SEQ ID NO: 7)

Forward ANA Primer 2

5'- ANA - ATATATATCCTCACCACACTCCACC - 3'           (SEQ ID NO: 7)

Forward AQ Primer 2

5'- AQ - ATATATATCCTCACCACACTCCACC - 3'            (SEQ ID NO: 7)

Forward Psor Primer 2

5'- Psor - ATATATATCCTCACCACACTCCACC - 3'          (SEQ ID NO: 7)

Forward PCR Primer 2

5'- ATATATATCCTCACCACACTCCACC - 3'                     (SEQ ID NO: 8)

Reverse Primer 2

5'- TTTTTTTTGTGTCTGTCTGTGTCCTC - 3'                    (SEQ ID NO: 9)

Reverse PCR Primer 2

5'- ABABTTTTTTTTGTGTCTGTCTGTGTCCTC - 3'                (SEQ ID NO: 10)

Figure 3B

Anthraquinone (AQ)
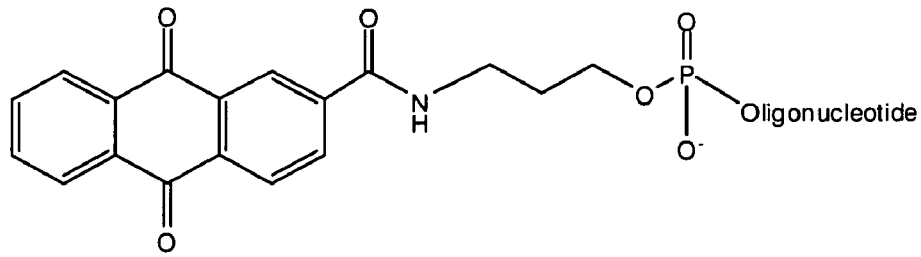
4-Azido-2-nitro-aniline (ANA)
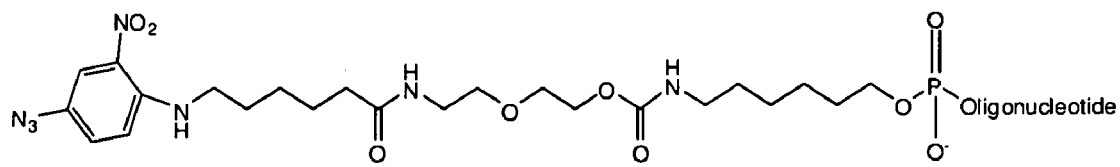
Psoralen (Psor)
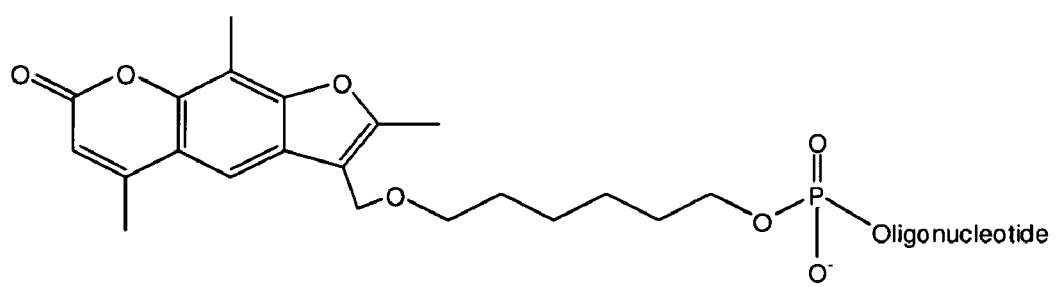
5-bromo-dUTP (BrdU)
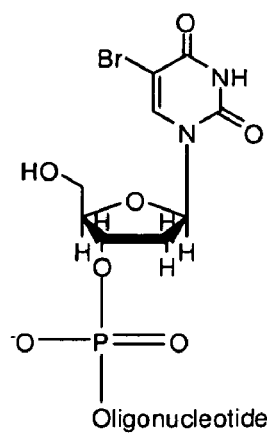
Figure 4

2092-68_5:
ATATATAXGAGTGACCGTCTGCCTGAGCZGCGGZZGAZGAZAZACZZCGCZ
ZZCACZGCZCACACCAGACGACGAGCGGGA        (SEQ ID NO: 11)

2092-68_6:
ATATATAXGAGTGACCGTCTGCCTGAGCZGCGGZZGAZGAZAZACZZCGCZ
ZZCACZGCZCACAC        (SEQ ID NO: 12)

T8-3P7
           TTTTTTTTTCCCGCTCGTCGTCTG        (SEQ ID NO: 13)

Figure 6

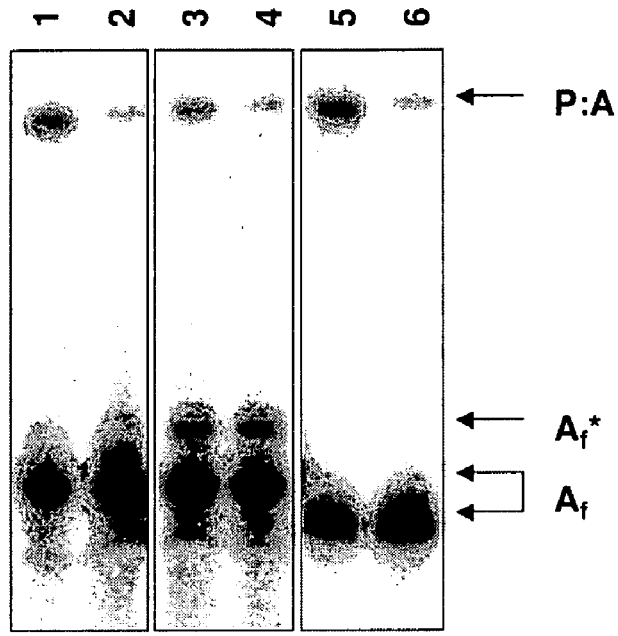
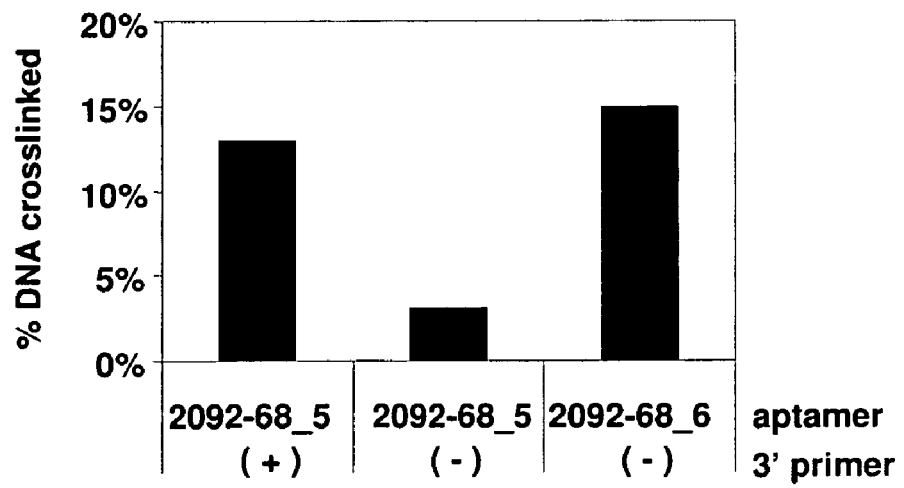
Figure 7

A.

| | | |
|---|---|---|
| 1546-23 (SEQ ID NO: 14) | CCGTATGCCGCCGTCGGCGTTTTAAGACCTTAG | |
| 1546-23*ab* (SEQ ID NO: 15) | CCGTATGCCGCCGTCGGCGTTTTAAGACCTTAG | A = dA |
| 1546-23*cd* (SEQ ID NO: 16) | CCGTATGCCGCCGTCGGCGTTTTAAGACCTTAG | C = dC |
| 1546-23*ef* (SEQ ID NO: 17) | CCGTATGCCGCCGTCGGCGTTTTAAGACCTTAG | C = BrdC |
| 1546-23*gh* (SEQ ID NO: 18) | CCGTATGCCGCCGTCGGCGTTTTAAGACCTTAG | G = dG |
| 1546-23*ij* (SEQ ID NO: 19) | CCGTATGCCGCCGTCGGCGTTTTAAGACCTTAG | T = BndU |

B.

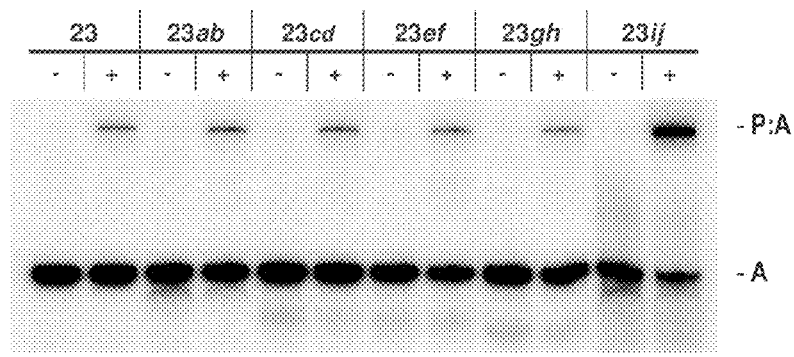

C.

| Variant | Percent Crosslinked |
|---|---|
| 1546-23 | 7 |
| 1546-23*ab* | 10 |
| 1546-23*cd* | 7 |
| 1546-23*ef* | 11 |
| 1546-23*gh* | 8 |
| 1546-23*ij* | 58 |

Figure 8

Figure 10
A.
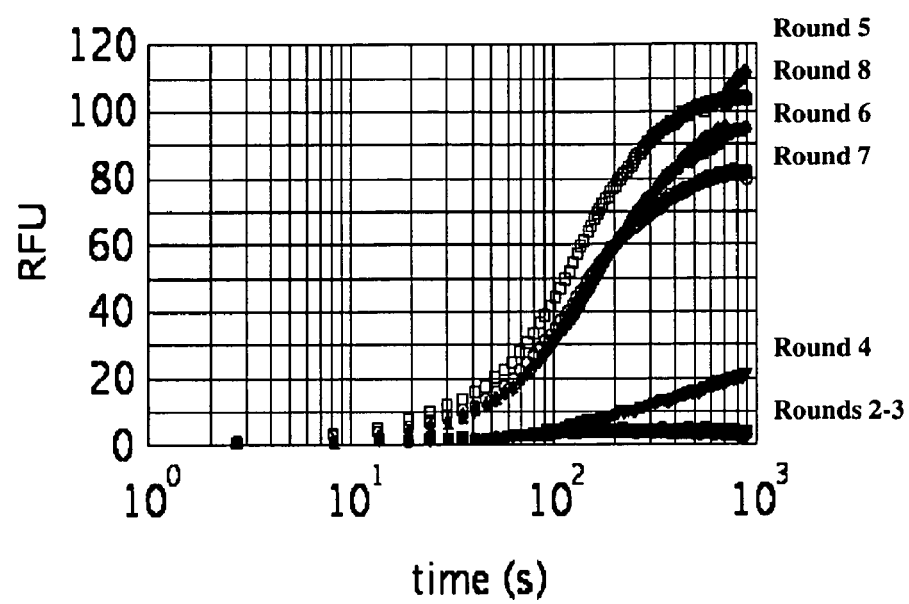
B.
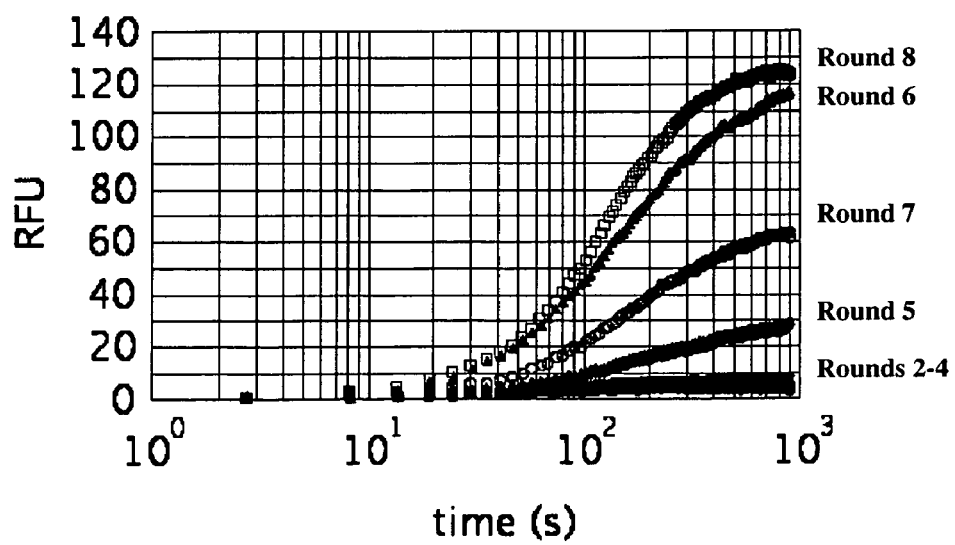

P-cadherin

Pattern 1

| Seq Id | Count | | |
|---|---|---|---|
| 1679-71 | 8 | TCGTCT ATATATTTAC AGTGTGGGCCGTGCTGCCACGAGG | SEQ ID NO: 20 |
| 1679-68 | 4 | GAGAGGCTCTG ATATATTTAC GTAGTCTGCGAGACCAGTC | SEQ ID NO: 21 |

Pattern 2

| Seq Id | Count | | |
|---|---|---|---|
| 1679-67 | 1 | TGAGCCCGGGGGATTGACCA ATATCGTATGATACG GGTGG | SEQ ID NO: 22 |
| 1679-79 | 1 | ATCATGGGCTTGATTGGCAAC ATATCGTATGATACG TGCA | SEQ ID NO: 23 |

Orphans

| Seq Id | Count | | |
|---|---|---|---|
| 1679-78 | 2 | CTGACGACGTTCGGTATTCATCTTCCAATACCACGCGGGT | SEQ ID NO: 24 |
| 1679-75 | 2 | TCGGAGGGGGATCTGCCTGGCTTGCTACGCGCGGTCGT | SEQ ID NO: 25 |
| 1679-93 | 1 | TACCTTGAAAGGGGACATGATGCCTTCGTATCGGGTTCGC | SEQ ID NO: 26 |
| 1679-70 | 2 | CGCATTGCCAACTGATATGATCCAACAGCCTTGTACGTGA | SEQ ID NO: 27 |
| 1679-77 | 1 | GTGTGGAGGGCTGCGGTAGGGAGCATCAGTAGCCGGGTGG | SEQ ID NO: 28 |
| 1679-80 | 1 | GGGTCGCTGGTGTGGGGTGGGTGGGTGGGCTTCTGTGAT | SEQ ID NO: 29 | gp130

Pattern 1

| Seq Id | Count | | |
|---|---|---|---|
| 1704-12 | 7 | TGCCTGAGGCCCGTCTTA GATCCATTTCGAGTTAGGGC GGT | SEQ ID NO: 30 |
| 1704-22 | 1 | TGGTACAGCTCTTG GATCCATTTCGAGTTAGGGC CCCCGG | SEQ ID NO: 31 |

Pattern 2

| Seq Id | Count | | |
|---|---|---|---|
| 1704-2 | 2 | GGCCTATGCGTGGGTGATTTGAAGGGCG GCTGGTCGG TAG | SEQ ID NO: 32 |
| 1704-11 | 1 | GCTGGCGTAGCCTGGGGGGTC GCTGGTCGG GGTGGGCGGG | SEQ ID NO: 33 |
| 1704-23 | 1 | GCGGTAGGTAGAGTTAGGGGGGTG GCTGGTCGG TTGCGCT | SEQ ID NO: 34 |

Pattern 3

| Seq Id | Count | | |
|---|---|---|---|
| 1704-10 | 3 | GGCGCTTGC ATCCATTCGTTTAG CGCAAGGGCTCAG | SEQ ID NO: 35 |
| 1704-9 | 1 | CGGCTTGG ATCCATTCGTTTAG TGG | SEQ ID NO: 36 |
| 1704-6 | 1 | ACCAACCCGCTTTG ATCCATTAGTTTAG CGCCTAGGTGGG | SEQ ID NO: 37 |

Orphans

| Seq Id | Count | | |
|---|---|---|---|
| 1704-3 | 4 | GTAGTAAGCGGATTCATTAACTGTCTCATCCCTGACTGAG | SEQ ID NO: 38 |
| 1704-13 | 3 | GGTCCGCGGATTTGCGGCGCTTGATCAAGCGTTTAGCCCCC | SEQ ID NO: 39 |
| 1704-1 | 1 | TATTTGGGAGGATTCCTAACCCTATGTCCAACTCGGCCCA | SEQ ID NO: 40 |
| 1704-5 | 1 | TAACTAGTTACGACTGTTGGAACCCTTTGGCCGGCACTGCA | SEQ ID NO: 41 |
| 1704-31 | 1 | TCTATCGTGTTTGATTGGTGCGCTGCATTGGCAGGACGCG | SEQ ID NO: 42 |
| 1704-29 | 1 | GTAAGGGGATTGCACCAGTTGAGGCCTTTTGGGGTGGCGG | SEQ ID NO: 43 |
| 1704-27 | 1 | AAGGGCAGGCATGGAGCTGTCGGTAAGCTAGGTTTGGCCA | SEQ ID NO: 44 |

FIGURE 12

SELEX AND PHOTOSELEX

RELATED APPLICATIONS

This application claims the benefit of U.S. Provisional Application Ser. No. 60/950,281, filed Jul. 17, 2007, U.S. Provisional Application Ser. No. 60/950,293, filed Jul. 17, 2007, U.S. Provisional Application Ser. No. 60/950,283, filed Jul. 17, 2007, U.S. Provisional Application Ser. No. 61/031, 420, filed Feb. 26, 2008 and U.S. Provisional Application Ser. No. 61/051,594, filed May 8, 2008. Each of these applications is incorporated by reference herein in its entirety.

FIELD OF THE INVENTION

The present disclosure relates generally to methods for the generation of aptamers and photoaptamers having improved properties and the improved aptamers and photoaptamers generated thereby.

BACKGROUND

The following description provides a summary of information relevant to the present disclosure and is not a concession that any of the information provided or publications referenced herein is prior art to the presently claimed current invention.

The SELEX process is a method for the in vitro evolution of nucleic acid molecules that are able to bind with high specificity to target molecules and is described in U.S. Pat. No. 5,475,096 entitled "Nucleic Acid Ligands" and U.S. Pat. No. 5,270,163 (see also WO 91/19813) entitled "Nucleic Acid Ligands" each of which is specifically incorporated by reference herein in its entirety. These patents, collectively referred to herein as the SELEX Patents, describe methods for making a nucleic acid ligand to any desired target molecule.

The basic SELEX process has been modified to achieve a number of specific objectives. For example, U.S. Pat. No. 5,707,796, entitled "Method for Selecting Nucleic Acids on the Basis of Structure" describes the use of the SELEX process in conjunction with gel electrophoresis to select nucleic acid molecules with specific structural characteristics, such as bent DNA. U.S. Pat. No. 5,580,737, entitled "High-Affinity Nucleic Acid Ligands That Discriminate Between Theophylline and Caffeine" describes a method for identifying highly specific nucleic acid ligands able to discriminate between closely related molecules, termed Counter-SELEX. U.S. Pat. No. 5,567,588, entitled "Systematic Evolution of Ligands by EXponential Enrichment: Solution SELEX" describes a SELEX-based method which achieves highly efficient partitioning between oligonucleotides having high and low affinity for a target molecule. U.S. Pat. No. 5,496, 938, entitled "Nucleic Acid Ligands to HIV-RT and HIV-1 Rev" describes methods for obtaining improved nucleic acid ligands after SELEX has been performed. U.S. Pat. No. 5,705,337, entitled "Systematic Evolution of Ligands by Exponential Enrichment Chemi-SELEX" describes methods for covalently linking a nucleic acid ligand to its target.

The SELEX process encompasses the identification of high-affinity nucleic acid ligands containing modified nucleotides conferring improved characteristics on the ligand, such as improved in vivo stability or improved delivery characteristics. Examples of such modifications include chemical substitutions at the ribose and/or phosphate and/or base positions. SELEX process-identified nucleic acid ligands containing modified nucleotides are described in U.S. Pat. No. 5,660,985, entitled "High Affinity Nucleic Acid Ligands Containing Modified Nucleotides" that describes oligonucleotides containing nucleotide derivatives chemically modified at the 5- and 2'-positions of pyrimidines. U.S. Pat. No. 5,580, 737, see supra, describes highly specific nucleic acid ligands containing one or more nucleotides modified with 2'-amino (2'—$NH_2$), 2'-fluoro (2'-F), and/or 2'-O-methyl (2'-OMe).

Further modifications of the SELEX process are described in U.S. Pat. No. 5,763,177, U.S. Pat. No. 6,001,577, and U.S. Pat. No. 6,291,184, each of which is entitled "Systematic Evolution of Nucleic Acid Ligands by Exponential Enrichment: Photoselection of Nucleic Acid Ligands and Solution SELEX"; see also, e.g., U.S. Pat. No. 6,458,539, entitled "Photoselection of Nucleic Acid Ligands". These patents, collectively referred to herein as "the PhotoSELEX Patents," describe various SELEX methods for selecting nucleic acid ligands containing photoreactive functional groups capable of binding and/or photocrosslinking to and/or photoinactivating a target molecule. The resulting photoreactive nucleic acid ligands are referred to as photocrosslinking nucleic acid ligands or photoaptamers.

Although these SELEX and photoSELEX processes are useful, there is always a need for processes that lead to improved properties of nucleic acid ligands generated from in vitro selection techniques. For example, a need exists for a method for producing nucleic acid ligands to target molecules with better binding affinities than those achieved with naturally occurring DNA or RNA nucleotides. Additionally, a need exists for a method for producing photoaptamers with increased photocrosslinking yields and enhanced photo-selectivity. Also, there is a need for methods for producing nucleic acid ligands, both affinity- and photo-aptamers, with a minimal number of nucleotides required to impart the properties of interest.

SUMMARY

The present disclosure describes improved SELEX methods for generating nucleic acid ligands that are capable of binding to target molecules and improved photoSELEX methods for generating photoreactive nucleic acid ligands that are capable of both binding and covalently crosslinking to target molecules. The disclosure further describes nucleic acid libraries having expanded physical and chemical properties and their use in SELEX and photoSELEX; methods for increasing the crosslinking efficiencies of photoaptamers; methods for producing photoaptamers having selective modifications that enhance functionality and minimize non-specific photoreactions; and methods for generating truncated nucleic acid ligands from nucleic acid ligands of longer length. The disclosure further describes aptamers and photoaptamers obtained using any of the foregoing methods.

In one aspect, the disclosure provides methods for selecting and identifying modified nucleic acid ligands from a candidate mixture of randomized modified nucleic acid sequences on the basis of the ability of the randomized modified nucleic acid sequences to either (1) bind to a target molecule or (2) bind to a target molecule and subsequently form a covalent linkage with the target molecule upon irradiation. Suitable modifications include but are not limited to 5-position adducts on the pyrimidine bases, 2'-position modifications on ribose rings, and phosphodiester backbone modifications. Adduct groups can alter fundamental aptamer properties, such as, for example, the hydrophobicity, hydrophilicity, charge, polarizability, and hydrogen bonding character of the overall aptamer. Altering the physical characteristics of the nucleic acid sequences used in SELEX or photoSELEX by introducing modified nucleotides allows for high affinity binding to targets that show little binding to nucleic acid sequences comprised of the naturally occurring nucleotide bases.

In one embodiment, the method comprises: (a) preparing a candidate mixture of nucleic acid sequences that contain modified nucleotide bases; (b) contacting the candidate mixture with a target molecule wherein nucleic acid sequences with the highest relative affinities to the target molecule preferentially bind the target molecule, forming nucleic acid-target molecule complexes; (c) partitioning the bound nucleic acid-target molecule complexes from free nucleic acids in the candidate mixture; and (d) identifying the nucleic acid sequences that were bound to the target molecule. The process can further include the iterative step of amplifying the nucleic acids that bind to the target molecule to yield a mixture of nucleic acids enriched in sequences that are able to bind to the target molecule. In addition to the modified base, the candidate mixture can also contain photoreactive nucleotides in the sequence. These photoreactive nucleotides can be used to secure the target to the nucleic acid ligand either covalently or by ionic interactions.

In one embodiment, the variable region of the aptamer includes nucleotides having base modifications. These aptamers can be used in the methods, devices, and kits relying on the assay sequence described here. These modified nucleotides have been shown to produce novel aptamers that have very slow off-rates for the release of the specific target while maintaining high affinity to the target.

In one embodiment, the method comprises the inclusion in the candidate mixture of modified pyrimidines having a non-hydrogen group at position C-5 that resembles a photoreactive group from a steric or polarity standpoint, but is essentially non-photoreactive (a "non-photoreactive placeholding pyrimidine"), allowing for the post-SELEX substitution of one or more photoreactive pyrimidines into an affinity-selected aptamer and the production of a photoaptamer without substantial loss of affinity.

In other embodiments, the method comprises inclusion in the candidate mixture of pyrimidines having modifications at the C-5 base position, which confer other properties to the candidate mixture, for example, modifications that provide additional functional properties to the candidate mixture (a "modified pyrimidine"). In either instance, the C-5 modification can be introduced through an amide linkage, directly, or through another type of linkage. However, other methods for modification may be suitable.

In some embodiments the modifications can be selected from the group of compounds shown in FIG. 2, which illustrates particular base modifications of nucleotides which are described in the instant disclosure. With reference to FIG. 2, R denotes 5-position modifications and X illustrates various linkers that can be used between the nucleotide attachment point and the R group. The positions of attachment for the various "R" groups are also indicated on the respective R groups.

Aptamers containing nucleotides with modified bases have a number of properties that are different than standard aptamers. It has been surprisingly observed that the structure of the identified aptamers does not appear to be entirely what base pairing models may predict. This is supported by the fact that the measured melting temperatures of the aptamers are not what the models may predict. On average, the calculated Tm is 6° C. lower than the measured Tm. The measured melting temperatures indicate the aptamers including these modified nucleotides are more stable than may be predicted and potentially possess novel secondary structures. These modified aptamers also have different circular dichroism spectra than the corresponding standard aptamers. Additionally, identification of slow off-rate aptamers are more likely when modified nucleotides are used in the production of the initial library or candidate mixture compared to standard nucleotide libraries.

In another embodiment, photoaptamers that are initially selected from a candidate nucleic acid mixture containing photoreactive functional groups at all locations of a particular pyrimidine in the nucleic acid sequence (for example, all BrdU or all BrdC) can be optimized by retaining those photoreactive functional groups that are involved in photocrosslinking to the target and eliminating other photoreactive functional groups that may contribute to non-specific crosslinking.

In one series of embodiments, improved photoaptamers can be obtained by a method where affinity aptamers are first obtained from a candidate mixture comprising at least one modified non-photoreactive placeholding pyrimidine. Once an affinity aptamer is obtained, one or more modified non-photoreactive placeholding pyrimidines is replaced with one or more photoreactive pyrimidines and the best photoaptamer is identified by screening these aptamer variants for photocrosslinking activity. More specifically, this embodiment includes a method for identifying a photoaptamer of a target molecule comprising: (a) preparing a candidate mixture of nucleic acids comprising modified non-photoreactive placeholding pyrimidines; (b) contacting the candidate mixture with the target, wherein nucleic acids having an increased affinity to the target relative to the candidate mixture can be partitioned from the remainder of the candidate mixture; (c) partitioning the increased affinity nucleic acids from the remainder of the candidate mixture; (d) amplifying the increased affinity nucleic acids to yield a nucleic acid ligand-enriched mixture of nucleic acids; (e) repeating steps (b)-(d) as desired; (f) producing from said nucleic acid ligand-enriched mixture of nucleic acids a candidate photoaptamer, or a mixture of candidate photoaptamers, by replacing in each nucleic acid of the ligand-enriched mixture of nucleic acids one or more non-photoreactive placeholding pyrimidines with a photoreactive pyrimidine; (g) contacting said candidate photoaptamer(s) with said target molecule wherein a candidate photoaptamer-target complex is formed; (h) irradiating said candidate photoaptamer-target complex; (i) determining whether said candidate photoaptamer-target complex has photocrosslinked; (j) repeating steps (f)-(i) as necessary; and (k) identifying at least one photocrosslinking nucleic acid ligand to the target.

In another series of embodiments, improved photoaptamers can be obtained by a method where affinity aptamers are first obtained from a candidate mixture comprising at least one non-photoreactive placeholding nucleotide and at least one modified nucleotide. Once an affinity aptamer is obtained, one or more of the non-photoreactive placeholding nucleotides is replaced with one or more photoreactive nucleotides, and a photoaptamer is identified by screening these aptamer variants for photocrosslinking activity. More specifically, this embodiment includes a method for identifying a photoaptamer to a target molecule, the method comprising: (a) preparing a candidate mixture of nucleic acids comprising: (i) at least one non-photoreactive placeholding nucleotide; (ii) at least one pyrimidine nucleotide modified at the C-5 position of the base, where the modification is selected from the group shown in FIG. 2; (b) contacting the candidate mixture with the target molecule, wherein nucleic acids having an increased affinity to the target relative to the candidate mixture can be partitioned from the remainder of the candidate mixture; (c) partitioning the increased affinity nucleic acids from the remainder of the candidate mixture; (d) amplifying the increased affinity nucleic acids to yield a ligand-enriched mixture of nucleic acids; (e) repeating (b)-(d) as desired; (f) producing from said nucleic acid ligand-enriched mixture of nucleic acids a candidate photoaptamer, or a mixture of candidate photoaptamers, by replacing in each nucleic acid of the ligand-enriched mixture of nucleic acids one or more non-photoreactive placeholding pyrimidines with a photoreactive pyrimidine; (g) contacting said candidate photoaptamer(s) with said target wherein a candidate photoaptamer-target complex is formed; (h) irradiating said candidate photoaptamer-target complex; (i) determining whether said candidate photoaptamer-target complex has photocrosslinked; (j) repeating steps (f)-(i) as necessary; and (k) identifying at least one photoaptamer to the target molecule.

In another series of embodiments, photoaptamers having a plurality of photoreactive pyrimidines are selected, a determination is made to identify the one or more photoreactive pyrimidines that photocrosslink to the target molecule, and one or more of the photoreactive pyrimidines that are not included in the photocrosslink to the target are subsequently substituted with non-photoreactive pyrimidines. This embodiment can provide photoaptamers with a lower incidence of non-specific crosslinking. More specifically, this embodiment includes a method for identifying a photoaptamer comprising: (a) preparing a candidate mixture of nucleic acids, wherein each member of said candidate mixture comprises a plurality of photoreactive pyrimidines, and contacting said candidate mixture with a target molecule, wherein nucleic acids having an increased affinity to the target relative to the candidate mixture form nucleic acid-target molecule complexes; (b) irradiating said complexes, wherein said nucleic acid-targets photocrosslink; (c) partitioning the photocrosslinked nucleic acid-target molecule complexes from the candidate mixture; (d) identifying a candidate photoaptamer that photocrosslinked to the target; (e) determining which photoreactive pyrimidine(s) in said candidate photoaptamer photocrosslinks to said target by (i) scanning replacements, including chemically synthesizing a set of candidate photoaptamer variants that vary in the photoreactive pyrimidine positions that are replaced with non-photoreactive pyrimidines, or (ii) gel mobility shift-based photocrosslink site identification; and (f) replacing one or more photoreactive pyrimidines in said candidate photoaptamer other than the photoreactive base(s) identified in (e) with non-photoreactive pyrimidines.

In another aspect, the disclosure provides nucleic acid sequences containing photoreactive functional groups. The nucleic acid sequences can contain single or multiple photoreactive functional groups. Further, in the case of nucleic acid sequences containing multiple photoreactive functional groups, the photoreactive functional groups can be the same or different. The photoreactive groups incorporated into the nucleic acids can include any chemical group capable of forming a crosslink with a target molecule upon irradiation.

In another aspect, the disclosure provides methods for obtaining photoaptamers with more varied photoreactive chromophores as compared to previous photoSELEX methods. In this embodiment, one places one or more photoreactive group(s) at the 3' or 5' end of the nucleic acid sequence, close to the 3' or 5' end of the nucleic acid sequence or internally in the nucleic acid sequence. The photoreactive group(s) can include virtually any appropriate chromophore and need not be directly attached to a nucleotide base. Photoreactive chromophores can be tuned to absorb radiation at relatively longer wavelengths, thereby reducing the likelihood of inadvertently exciting chromophores on target molecules. For example, tryptophan residues in protein target molecules absorb UV light at 295 nm, so photoreactive chromophores that absorb light at wavelengths within the range of visible light (>400 nm) will reduce the likelihood of exciting protein molecules. Also, using chromophores with high molar absorbtivity at the excitation wavelength allows for the use of inexpensive light sources, such as LEDs, for photoactivation. In one embodiment, called "5' Fixed PhotoSELEX", the chromophore is placed at or near the 5' end of the nucleic acid sequence. This placement of the chromophore at or near the 5'-end of the sequence also facilitates the nucleic acid amplification process.

In one embodiment, the method comprises preparing a candidate mixture of nucleic acid sequences wherein each nucleic acid contains at least one photoreactive functional group; contacting the candidate mixture with a target molecule wherein nucleic acid sequences having the highest relative affinities to the target molecule preferentially bind the target molecule, forming nucleic acid-target molecule complexes; irradiating the nucleic acid-target molecule mixture, wherein some nucleic acids incorporated in nucleic acid-target molecule complexes crosslink to the target molecule via the photoreactive functional group; partitioning the crosslinked nucleic acid-target molecule complexes from both free nucleic acids and non-covalent nucleic acid-target complexes in the candidate mixture; and identifying the nucleic acid sequences that photocrosslinked to the target molecule. The process can further include the iterative step of amplifying the nucleic acids that photocrosslinked to the target molecule to yield a mixture of nucleic acids enriched in sequences that are able to photocrosslink to the target molecule.

In another embodiment, nucleic acid sequences containing one or more photoreactive groups are selected in the initial rounds of SELEX without the use of an irradiation step, resulting in a candidate mixture with a partially enhanced affinity for the target molecule. Additional rounds of photoSELEX are conducted with the irradiation step to select nucleic acid ligands that are able to photocrosslink to the target molecule.

In another aspect, the disclosure provides methods for obtaining aptamers or photoaptamers with truncated lengths compared to the sequences used in the initial SELEX candidate mixtures. In this embodiment, the nucleic acid sequences of a SELEX candidate mixture include a 5'-fixed end (or 5'-fixed region) separated from a 3'-fixed end (or 3'-fixed region) by a nucleotide sequence that varies, depending upon the aptamer, that is, a variable region. The fixed regions facilitate efficient enzymatic amplification of selected nucleic acid ligands. SELEX is performed using a candidate mixture with the 5'-fixed region, the 3'-fixed region, or both regions hybridized to oligonucleotide(s) with complementary sequence to form a long stem(s). The SELEX process is performed as described above with the variant that the nucleic acid pool includes nucleic acid sequences that have either one or both fixed regions hybridized to its complement prior to contacting the target molecule. In each round of SELEX, the amplified pool is hybridized with the appropriate complement prior to equilibration with the target. Once a set of clones has been isolated and sequenced, removal of the fixed region(s) on each clone that was hybridized to its complement during the SELEX procedure produces truncated molecules.

In one embodiment, a randomized set of nucleic acid sequences having each of their respective 3'-fixed regions hybridized to its complement is mixed with a quantity of the target molecule and allowed to establish binding equilibrium with the target molecule. This embodiment of SELEX in which a 3'-fixed region hybridizes to its complement is compatible with the previously described photoSELEX method (for example with a chromophore at or near the 5' end) for obtaining photoaptamers with increased numbers of photoreactive functional groups. In another embodiment, a randomized set of nucleic acid sequences having each of their respective 5'-fixed regions hybridized to its complement is mixed with a quantity of the target molecule and allowed to establish binding equilibrium with the target molecule.

In another embodiment, both the 5'-fixed region and 3'-fixed region of the nucleic acid sequences are each hybridized to their respective complements prior to contacting the target molecule. As one skilled in the art will appreciate, the chromophore for photoSELEX should not be placed in a region that will subsequently be truncated.

In another aspect, any feasible combination of the various methods and steps described herein can be used to generate a nucleic acid ligand capable of either (1) binding to a target molecule or (2) binding to a target molecule and subsequently forming a covalent linkage with the target molecule upon irradiation.

In another aspect, any feasible combination of the various methods and steps described herein can be used to generate a nucleic acid ligand capable of modifying the bioactivity of a target molecule through binding and/or crosslinking to the target molecule, for example, as an agonist or antagonist. In one embodiment, a nucleic acid ligand to a unique target molecule associated with a specific disease process is identified. In another embodiment, a nucleic acid ligand to a target molecule associated with a disease state is used to treat the disease in vivo.

In another aspect, the disclosure provides aptamers and photoaptamers identified by the improved methods, diagnostic kits that include such aptamers and photoaptamers, and therapeutic uses of such aptamers and photoaptamers. The aptamers and photoaptamers identified herein can be used in any diagnostic, imaging, high throughput screening or target validation techniques or procedures or assays for which aptamers, oligonucleotides, antibodies and ligands, without limitation can be used. For example, aptamers and photoaptamers identified herein can be used according to the methods described in detail in the concurrently filed U.S. application Ser. No. 12/175,446, entitled "Multiplexed Analyses of Test Samples", which is incorporated by reference herein in its entirety.

BRIEF DESCRIPTION OF THE FIGURES

FIGS. 2A and 2B exhibit the base modifications of nucleotides discussed in this disclosure. The R groups that can be used are described in addition to the linkers (X) that can be used between the nucleotide attachment point and the R group is shown (FIG. 2A). The positions of attachment for the various "R" groups are also indicated on the respective R groups (FIG. 2B).

FIGS. 3A and 3B show oligonucleotides that were used to prepare the candidate mixtures or perform various steps in the selection process. The oligonucleotides were prepared by standard solid-phase synthesis techniques. Two candidate mixture sequences were used in this example, designated 1 and 2. BrdU, Anthraquinone (AQ), and psoralen (Psor) chromophores were purchased as phosphoramidites and added to the 5' terminus of the forward primer during synthesis. 4-azido-2-nitro-aniline (ANA) was prepared as a para-nitrophenyl carbonate derivative and coupled to a 5' hexylamine phosphoramidite after synthesis. (FIG. 3A) Template 1 was only used with candidate mixtures containing 5'-BrdU, AQ, and ANA, and (FIG. 3B) Template 2 was only used with candidate mixtures containing 5'-Psor in the examples. B=dT-biotin.

FIG. 4 shows the chemical structures of the chromophores coupled to the 5' terminus of the forward primer.

FIG. 6 shows the sequences of aptamer 2092-68 with (2092-68_5) (SEQ ID NO:11) and without (2092-68_6) (SEQ ID NO:12) the 3' fixed region, and 3' primer T8-3P7 (SEQ ID NO:13). Sequences are shown in a 5'-3' orientation with the 40N region in boldface. X=ANA-dT, Z=BndU.

FIGS. 7A and 7B show a PAGE analysis of crosslink activity of β-catenin aptamer 2092-68 with and without the 3' fixed region. FIG. 7A. Image of radiolabeled species after PAGE separation of free aptamer ($A_f$), intramolecular crosslinked aptamer ($A_f^*$), and crosslinked protein:aptamer complexes (P:A). Lanes 1, 2, 5, 6: Aptamer 2092-68_5 (3' fixed region present). Lanes 3, 4: Aptamer 2092-68_6 (3' fixed region removed). Lanes 1, 3, 5: 10 nM b-catenin. Lanes 2, 4, 6: no protein. Lanes 1, 2: 3' primer was hybridized prior to binding and crosslinking. Lanes 3-6: no 3' primer hybridized. P:A complexes in lanes 1, 3, and 5 are large and do not migrate far from the origin, which is visible in lanes 2, 4, and 6 from residual DNA remaining in the wells. FIG. 7B. Calculated crosslink activities of samples 1-6. Values have been corrected by subtracting residual DNA signal.

FIGS. 8A, 8B, and 8C illustrate a method for converting an affinity aptamer to a photo-aptamer and identifying the photoreactive position. FIG. 8A. Variants of VEGF-sR2 BndU aptamer 1546-23 with consecutive pairs of dC positions substituted with BrdC. Only the variable region of the aptamer is shown. FIG. 8B. PAGE analysis of products of photocrosslinking each aptamer variant to either 100 nM VEGF-sR2 protein (+) or no protein (−). Free aptamer (A) migrates faster than covalent photo-aptamer: VEGF-sR2 complexes (P:A). FIG. 8C. Crosslink yields (percent of total aptamer crosslinked to 100 nM VEGF-sR2) for each aptamer variant.

FIGS. 10A and 10B depict renaturation response curves for selection rounds 2-8. FIG. 10A. P-Cadherin/IgG1-Fc/6-His. FIG. 10B. gp130/IgG1-Fc/6-His.

FIG. 11A. Libraries binding to P-Cadherin/IgG1-Fc/His$_6$ protein (● Enriched Library 5137-R8-S30 ($K_d$=2.0×10$^{-9}$ M), ■ Random Library 40N53.21 (Kd>1× 10$^{-7}$ M)). FIG. 11B. Libraries binding to gp130/IgG1-Fc/His$_6$ protein (● Enriched Library S138-R8-S29 ($K_d$=7.9×10$^{-10}$ M), ■ Random Library 40N53.21 ($K_d$>1×10$^{-7}$M)).

FIG. 12 depicts sequence alignments of high affinity libraries. In each alignment, TrpdU is represented by T. Orphans are sequences that do not contain any of the conserved patterns.

FIG. 13A. Aptamers binding to P-cadherin/IgG1-Fc/His$_6$ protein (● Aptamer 1679-70 ($K_d$=7.2×10$^{-10}$ M), ■ Aptamer 1679-71 ($K_d$=5.9×10$^{-10}$ M), ▼ Aptamer 1679-77 ($K_d$=3.3×10$^{-9}$ M), ◆ Aptamer 1679-79 ($K_d$=2.8×10$^{-9}$ M), ▲ Random Library 40N53.21 ($K_d$>1×10$^{-7}$ M). FIG. 13B. Aptamers binding to gp130/IgG1-Fc/His$_6$ protein (● Aptamer 1704-10 ($K_d$=1.5×10$^{-9}$ M), ■ Aptamer 1704-12 ($K_d$=3.5×10$^{-10}$ M), ▼ Aptamer 1704-2 ($K_d$=7.6×10$^{-10}$ M), ◆ Aptamer 1704-3 ($K_d$=2.1×10$^{-10}$ M), ▲ Random Library 40N53.21 ($K_d$>1×10$^{-7}$ M).

FIG. 14A. Aptamers binding to P-cadherin/IgG1-Fc/His$_6$ protein (● 5-MedC Aptamer 1679-71 ($K_d$=9.5×10$^{-11}$ M), ■ 5-BrdC Aptamer 1679-71 ($K_d$=5.6×10$^{-10}$ M). FIG. 14B. Aptamers binding to gp130/IgG1-Fc/His$_6$ protein (● 5-MedC Aptamer 1704-3 ($K_d$=1.2×10$^{-10}$ M), ■ 5-BrdC Aptamer 1704-3 ($K_d$=2.2×10$^{-10}$ M). FIG. 14C. Aptamers binding to gp130/IgG1-Fc/His$_6$ protein (● 5-MedC Aptamer 1704-12 ($K_d$=6.1×10$^{-10}$ M), ■ 5-BrdC Aptamer 1704-12 ($K_d$=2.3×10$^{-9}$ M).

FIG. 16A. Results from gel mobility shift-based photocrosslink site identification (explained in Examples, Material and Methods) for a photoaptamer (1192-2) to matrix metalloproteinase 1 (MMP-1). Whether binding reactions were irradiated with 1.0 J 308 nm light, and whether MMP-1 was included in the reaction mixtures, is indicated at the top of the figure. Two putative crosslinked (to MMP-1) BrdU nucleotide positions were identified (I and J in the figure; BrdU positions were alphabetically assigned, 5' to 3'). FIG. 16B. Variants of MMP-1 photoaptamer 1192-2 (●) were chemically synthesized with dT substituted for each BrdU position except position I (1192-2-I; ■) or except position J (1192-2-J; ▼), the photocrosslinking activities of each were assayed. The graph illustrates quantity of MMP-1 photocrosslinked as a function of MMP-1 concentration. Each data point represents the mean of triplicates. Standard deviation bars are shown. FIG. 16C. Results from gel mobility shift-based photocrosslink site identification for a photoaptamer (987-51) to tissue plasminogen activator protein (tPA). The dominant crosslinked BrdU nucleotide position was identified (position H). FIG. 16D. A variant of tPA photoaptamer 987-51 (●) was chemically synthesized with dT substituted for each BrdU position except position H (987-51-H; ■), the photocrosslinking activities of each were assayed. The graph illustrates quantity of tPA photocrosslinked as a function of tPA concentration. Each data point represents the mean of triplicates. Standard deviation bars are shown.

DETAILED DESCRIPTION

Figure 1:
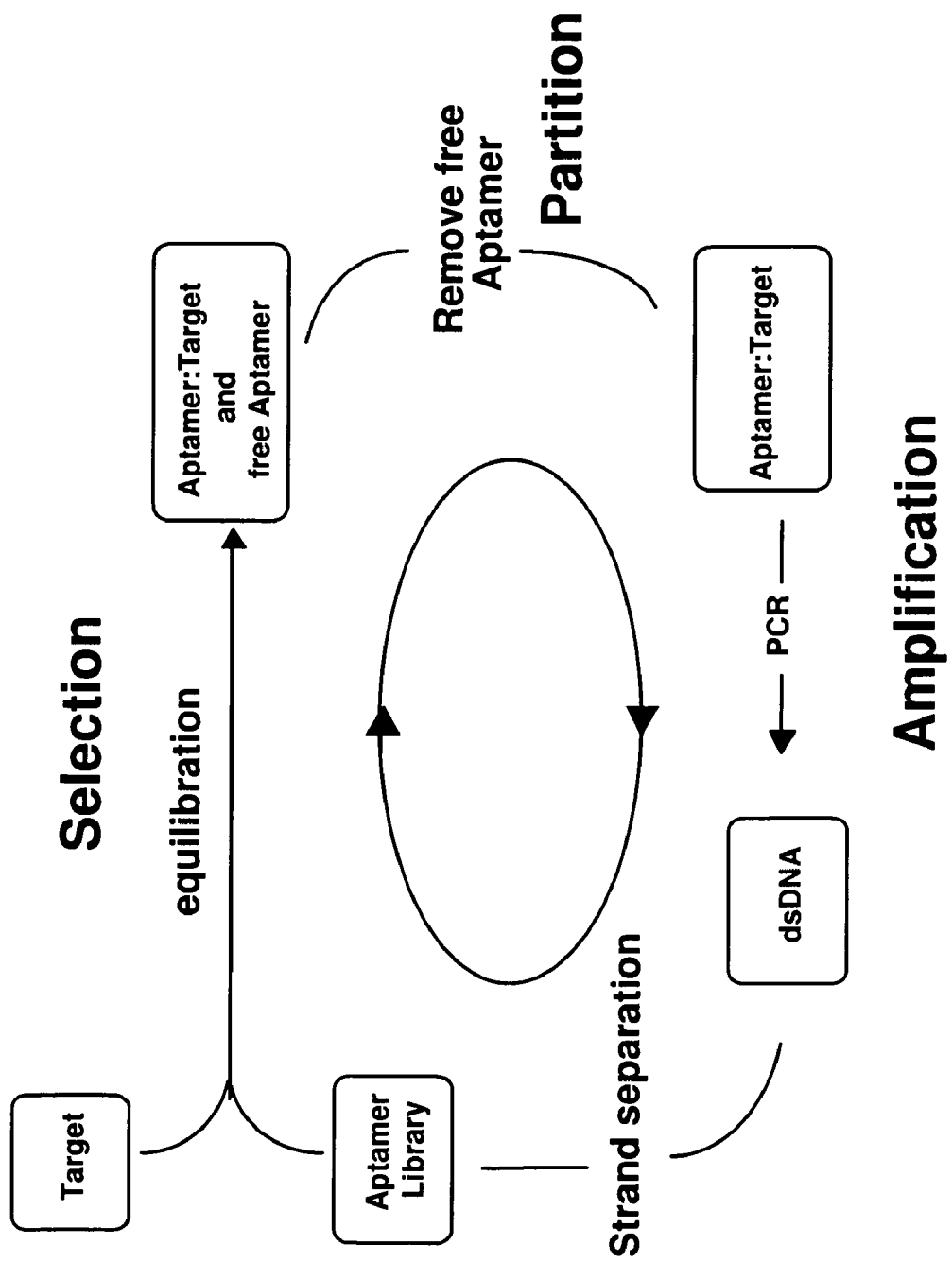
FIG. 1 illustrates the basic SELEX method.

The practice of the current invention employs, unless otherwise indicated, conventional methods of chemistry, microbiology, molecular biology, and recombinant DNA techniques within the level of skill in the art. Such techniques are explained fully in the literature. See, e.g., Sambrook, et al. *Molecular Cloning: A Laboratory Manual* (Current Edition); *DNA Cloning: A Practical Approach*, vol. I & II (D. Glover, ed.); *Oligonucleotide Synthesis* (N. Gait, ed., Current Edition); *Nucleic Acid Hybridization* (B. Hames & S. Higgins, eds., Current Edition); *Transcription and Translation* (B. Hames & S. Higgins, eds., Current Edition).

All publications, published patent documents, and patent applications cited in this specification are indicative of the level of skill in the art(s) to which the current invention pertains. All publications, published patent documents, and patent applications cited herein are hereby incorporated by reference to the same extent as though each individual publication, published patent document, or patent application was specifically and individually indicated as being incorporated by reference.

As used in this specification, including the appended claims, the singular forms "a," "an", and "the" include plural references, unless the content clearly dictates otherwise, and are used interchangeably with "at least one" and "one or more." Thus, for example, reference to "an aptamer" includes mixtures of aptamers.

As used herein, the term "about" represents an insignificant modification or variation of the numerical values such that the basic function of the item to which the numerical value relates is unchanged.

As used herein, the terms "comprises," "comprising," "includes," "including," "contains," "containing," and any variations thereof, are intended to cover a non-exclusive inclusion, such that a process, method, product-by-process, or composition of matter that comprises, includes, or contains an element or list of elements does not include only those elements but can include other elements not expressly listed or inherent to such process, method, product-by-process, or composition of matter.

As used herein, "nucleic acid ligand," "aptamer," and "clone" are used interchangeably to refer to a non-naturally occurring nucleic acid that has a desirable action on a target molecule. A desirable action includes, but is not limited to, binding of the target, catalytically changing the target, reacting with the target in a way that modifies or alters the target or the functional activity of the target, covalently attaching to the target (as in a suicide inhibitor), and facilitating the reaction between the target and another molecule. In one embodiment, the action is specific binding affinity for a target molecule, such target molecule being a three dimensional chemical structure other than a polynucleotide that binds to the nucleic acid ligand through a mechanism which is independent of Watson/Crick base pairing or triple helix binding, wherein the nucleic acid ligand is not a nucleic acid having the known physiological function of being bound by the target molecule. Nucleic acid ligands include nucleic acids that are identified from a candidate mixture of nucleic acids, said nucleic acid ligand being a ligand of a given target, by the method comprising: (a) contacting the candidate mixture with the target, wherein nucleic acids having an increased affinity to the target relative to other nucleic acids in the candidate mixture can be partitioned from the remainder of the candidate mixture; (b) partitioning the increased affinity nucleic acids from the remainder of the candidate mixture; and (c) amplifying the increased affinity nucleic acids to yield a ligand-enriched mixture of nucleic acids, whereby nucleic acid ligands of the target molecule are identified. It is recognized that affinity interactions are a matter of degree; however, in this context, the "specific binding affinity" of an aptamer for its target means that the aptamer binds to its target generally with a much higher degree of affinity than it binds to other, non-target, components in a mixture or sample. An "aptamer" or "nucleic acid ligand" is a set of copies of one type or species of nucleic acid molecule that has a particular nucleotide sequence. An aptamer can include any suitable number of nucleotides. "Aptamers" refer to more than one such set of molecules. Different aptamers can have either the same or different numbers of nucleotides. Aptamers may be DNA or RNA and may be single stranded, double stranded, or contain double stranded regions.

As used herein, "candidate mixture" is a mixture of nucleic acids of differing sequence from which to select a desired ligand. The source of a candidate mixture can be from naturally-occurring nucleic acids or fragments thereof, chemically synthesized nucleic acids, enzymatically synthesized nucleic acids or nucleic acids made by a combination of the foregoing techniques. Modified nucleotides, such as nucleotides with photoreactive groups or non-photoreactive placeholding groups, can be incorporated into the candidate mixture. In addition, a first SELEX process can be used to produce a candidate mixture, that is, a ligand-enriched mixture of nucleic acids that is used as the candidate mixture in a second SELEX process experiment. A candidate mixture can also comprise nucleic acids with one or more common structural motifs. As used herein, a candidate mixture is also sometimes referred to as a "pool" or a "library." For example, an "RNA pool" refers to a candidate mixture comprised of RNA.

As used herein, "nucleic acid," "oligonucleotide," and "polynucleotide" are used interchangeably to refer to a polymer of nucleotides of any length, and such nucleotides can include deoxyribonucleotides, ribonucleotides, and/or analogs or chemically modified deoxyribonucleotides or ribonucleotides. The terms "polynucleotide," "oligonucleotide," and "nucleic acid" include double- or single-stranded molecules as well as triple-helical molecules.

If present, chemical modifications of a nucleotide can include, singly or in any combination, 2'-position sugar modifications, 5-position pyrimidine modifications, modifications at exocyclic amines, substitution of 4-thiouridine, substitution of 5-bromo- or 5-iodo-uracil, backbone modifications, methylations, unusual base-pairing combinations such as the isobases isocytidine and isoguanidine, and the like. Modifications can also include 3' and 5' modifications, such as capping. Other modifications can include substitution of one or more of the naturally occurring nucleotides with an analog, internucleotide modifications such as, for example, those with uncharged linkages (e.g., methyl phosphonates, phosphotriesters, phosphoamidates, carbamates, etc.) and those with charged linkages (e.g., phosphorothioates, phosphorodithioates, etc.), those with intercalators (e.g., acridine, psoralen, etc.), those containing chelators (e.g., metals, radioactive metals, boron, oxidative metals, etc.), those containing alkylators, and those with modified linkages (e.g., alpha anomeric nucleic acids, etc.). Further, any of the hydroxyl groups ordinarily present in a sugar can be replaced by a phosphonate group or a phosphate group; protected by standard protecting groups; or activated to prepare additional linkages to additional nucleotides or to a solid support. The 5' and 3' terminal OH groups can be phosphorylated or substituted with amines, organic capping group moieties of from about 1 to about 20 carbon atoms, or organic capping group moieties of from about 1 to about 20 polyethylene glycol (PEG) polymers or other hydrophilic or hydrophobic biological or synthetic polymers. Other modifications include pyrimidine modification at the C-5 position which can be produced through an amide linkage directly at the C-5 position or by other types of linkages. In one embodiment, the method for modification of the nucleotides is through an amide linkage. However, other methods for modification can be suitable. Additionally, the modification can be made indirectly through other groups.

Figure 2B:
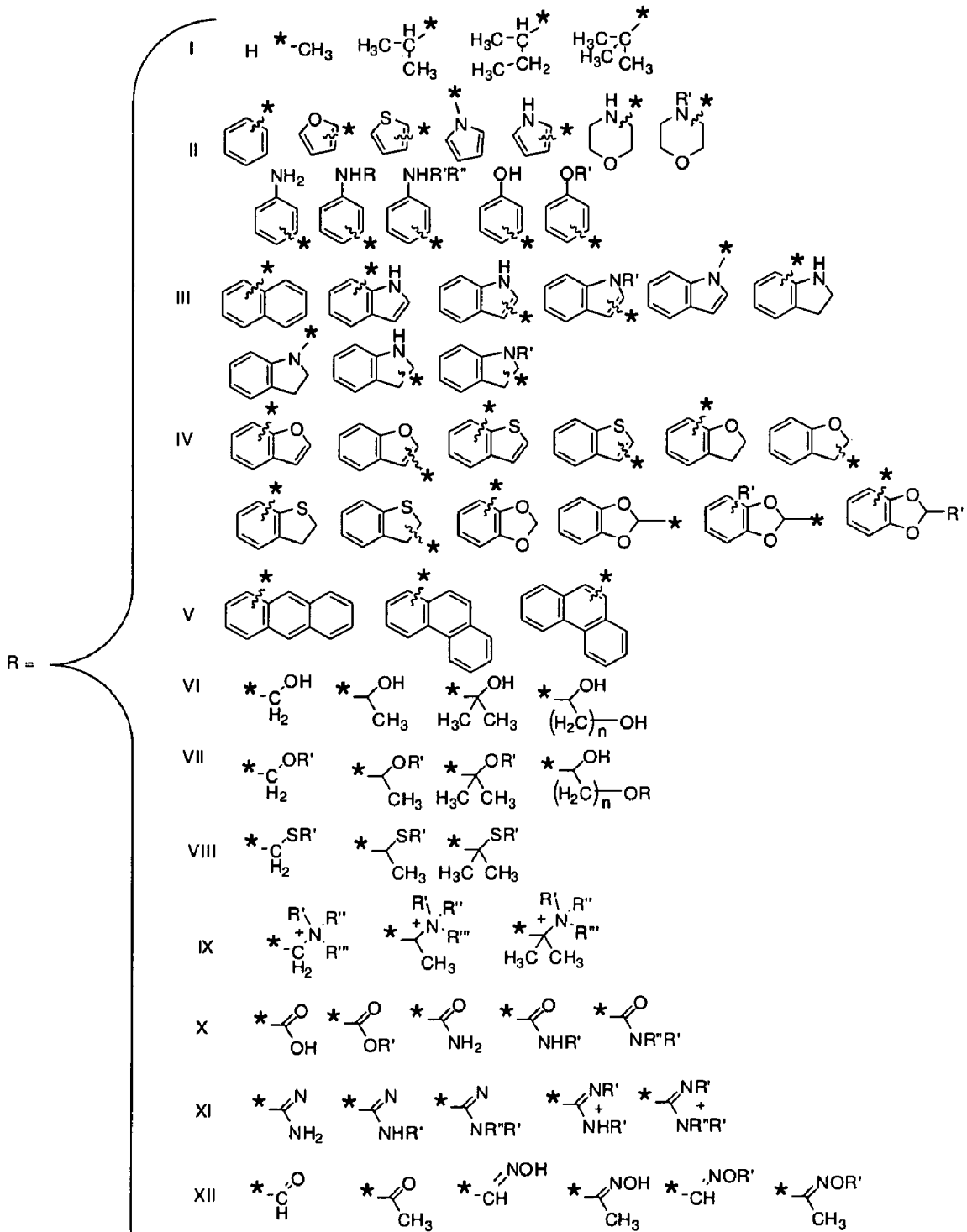

In one embodiment, the term "C-5 modified pyrimidine" refers to a pyrimidine with a modification at the C-5 position including, but not limited to those moieties illustrated in FIG. 2. Examples of a C-5 modified pyrimidine include those described in U.S. Pat. Nos. 5,719,273 and 5,945,527. Examples of a C-5 modification include substitution of deoxyuridine at the C-5 position with a substituent selected from: benzylcarboxyamide (alternatively benzylaminocarbonyl) (Bn), naphthylmethylcarboxyamide (alternatively naphthylmethylaminocarbonyl) (Nap), tryptaminocarboxyamide (alternatively tryptaminocarbonyl) (Trp), and isobutylcarboxyamide (alternatively isobutylaminocarbonyl) (iBu) as illustrated immediately below.

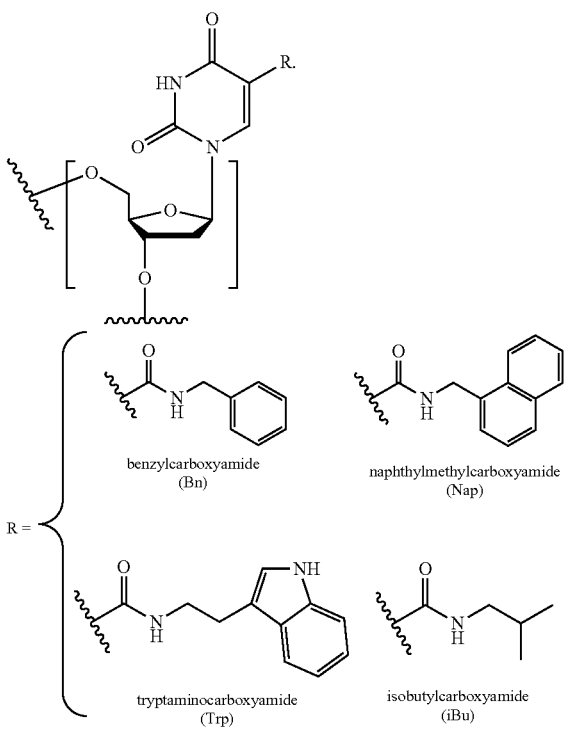

Representative C-5 modified pyrimidines include: 5-(N-benzylcarboxyamide)-2'-deoxyuridine (BndU), 5-(N-isobutylcarboxyamide)-2'-deoxyuridine (iBudU), 5-(N-tryptaminocarboxyamide)-2'-deoxyuridine (TrpdU), 5-(N-[1-(3-trimethylamonium) propyl]carboxyamide)-2'-deoxyuridine chloride, 5-(N-napthylmethylcarboxyamide)-2'-deoxyuridine (NapdU), or 5-(N-[1-(2,3-dihydroxypropyl)] carboxyamide)-2'-deoxyuridine). If present, a modification to the nucleotide structure can be imparted before or after assembly of a polymer. A sequence of nucleotides can be interrupted by non-nucleotide components. A polynucleotide can be further modified after polymerization, such as by conjugation with a labeling component.

Polynucleotides can also contain analogous forms of ribose or deoxyribose sugars, including 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. As noted above, one or more phosphodiester linkages can be replaced by alternative linking groups. These alternative linking groups include embodiments wherein phosphate is replaced by P(O)S ("thioate"), P(S)S ("dithioate"), (O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. Substitution of analogous forms of sugars, purines, and pyrimidines can be advantageous in designing a final product, as can alternative backbone structures like a polyamide backbone, for example.

In some aspects, it is desirable that certain modified nucleotides used in the SELEX process are capable of being amplified.

As used herein, "modified nucleic acid" refers to a nucleic acid sequence containing one or more modified nucleotides that are compatible with the SELEX process.

"Polypeptide," "peptide," and "protein" are used interchangeably herein to refer to polymers of amino acids of any length. The polymer can be linear or branched, it can comprise modified amino acids, and/or it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. Polypeptides can be single chains or associated chains.

As used herein, "non-photoreactive placeholding nucleotide" refers to a nucleotide which has been modified so as to be essentially equivalent to a photoreactive group from a steric and/or polarity standpoint. A "non-photoreactive placeholding pyrimidine" refers to a pyrimidine having a non-hydrogen group at position C-5 that resembles a photoreactive group from a steric and/or polarity standpoint and is essentially non-photoreactive. Examples of non-photoreactive placeholding steric pyrimidines include, but are not limited to, 5-methyl-dC and dT. 5-fluoro-dU and 5-fluoro-dC are examples of polarity placeholding pyrimidines suitable for replacement by the photoreactive 5-bromo-dU and 5-bromo-dC, respectively; in that the dipole moment of the C—F bond is similar to the dipole moment of the C—Br bond. Although the fluoro substitution is known to be photoreactive, it is much less reactive than bromo at 308 nM and therefore is essentially non-photoreactive. 5-methyl-dC is a non-photoreactive placeholding pyrimidine.

As used herein, "photoreactive nucleotide" means any modified nucleotide capable of photocrosslinking with a target protein upon irradiation with certain wavelengths of light. For example, photoaptamers produced by the photoSELEX process can include a photoreactive group selected from the following: 5-bromouracil (BrdU), 5-iodouracil (IdU), 5-bromovinyluracil, 5-iodovinyluracil, 5-azidouracil, 4-thiouracil, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-azidoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-bromodeoxyuridine, 8-bromo-2'-deoxyadenine, 5-iodo-2'-deoxyuracil, 5-iodo-2'-deoxycytosine, 5-[(4-azidophenacyl)thio] cytosine, 5-[(4-azidophenacyl)thio]uracil, 7-deaza-7-iodoadenine, 7-deaza-7-iodoguanine, 7-deaza-7-bromoadenine, and 7-deaza-7-bromoguanine. A "photoreactive pyrimidine" means any modified pyrimidine that is capable of photocrosslinking with a target upon irradiation of certain wavelengths. Exemplary photoreactive pyrimidines include 5-bromo-uracil (BrdU), 5-bromo-cytosine (BrdC), 5-iodo-uracil (IdU), and 5-iodo-cytosine (IdC). In various embodiments, the photoreactive functional group will absorb wavelengths of light that are not absorbed by the target or the non-modified portions of the oligonucleotide.

"SELEX" refers to a process that combines the selection of nucleic acid ligands that interact with a target in a desirable manner (e.g., binding to a protein) with the amplification of those selected nucleic acids. Optional iterative cycling of the selection/amplification steps allows selection of one or a small number of nucleic acids that interact most strongly with the target from a pool that contains a very large number of nucleic acids. Cycling of the selection/amplification procedure is continued until a selected goal is achieved. The SELEX methodology is described in the SELEX Patents. In some embodiments of the SELEX process, aptamers that bind non-covalently to their targets are generated. In other embodiments of the SELEX process, aptamers that bind covalently to their targets are generated.

As used herein the term "amplification" or "amplifying" means any process or combination of process steps that increases the amount or number of copies of a molecule or class of molecules.

"SELEX target" or "target molecule" or "target" refers herein to any compound upon which a nucleic acid can act in a desirable manner. A SELEX target molecule can be a protein, peptide, nucleic acid, carbohydrate, lipid, polysaccharide, glycoprotein, hormone, receptor, antigen, antibody, virus, pathogen, toxic substance, substrate, metabolite, transition state analog, cofactor, inhibitor, drug, dye, nutrient, growth factor, cell, tissue, any portion or fragment of any of the foregoing, etc., without limitation. Virtually any chemical or biological effector can be a suitable SELEX target. Molecules of any size can serve as SELEX targets. A target can also be modified in certain ways to enhance the likelihood or strength of an interaction between the target and the nucleic acid. A target can also include any minor variation of a particular compound or molecule, such as, in the case of a protein, for example, minor variations in amino acid sequence, disulfide bond formation, glycosylation, lipidation, acetylation, phosphorylation, or any other manipulation or modification, such as conjugation with a labeling component, which does not substantially alter the identity of the molecule. A "target molecule" or "target" is a set of copies of one type or species of molecule or multimolecular structure that is capable of binding to an aptamer. "Target molecules" or "targets" refer to more than one such set of molecules. Embodiments of the SELEX process in which the target is a peptide are described in U.S. Pat. No. 6,376,190, entitled "Modified SELEX Processes Without Purified Protein" incorporated herein by reference in its entirety.

As used herein, "competitor molecule" and "competitor" are used interchangeably to refer to any molecule that can form a non-specific complex with a non-target molecule. A "competitor molecule" or "competitor" is a set of copies of one type or species of molecule. "Competitor molecules" or "competitors" refer to more than one such set of molecules. Competitor molecules include oligonucleotides, polyanions (e.g., heparin, single-stranded salmon or herring sperm DNA, and polydextran), abasic phosphodiester polymers, dNTPs, and pyrophosphate.

As used herein, "non-specific complex" refers to a non-covalent association between two or more molecules other than an aptamer and its target molecule. A non-specific complex represents an interaction between classes of molecules.

Non-specific complexes include complexes formed between an aptamer and a non-target molecule, a competitor and a non-target molecule, a competitor and a target molecule, and a target molecule and a non-target molecule.

As used herein, the terms "slow off-rate enrichment process", refers to a process designed to enrich for an aptamer affinity complex with a slow dissociation rate from a set of nucleic acid-target complexes that includes a variety of dissociation rates. Slow off-rate enrichment can be applied by the addition of a competitor molecule, or by sample dilution, or by a combination of these methods. The effect of a slow off-rate enrichment depends upon the differing dissociation rates of aptamer affinity complexes. The duration of the slow off-rate enhancement process is chosen so as to retain a high proportion of aptamer affinity complexes with slow dissociation rates while substantially reducing the number of aptamer affinity complexes with fast dissociation rates. A slow off-rate enhancement process can be used before and after the partition process. When dilution is used as the slow off-rate enhancement process, the fold dilution can be as large as possible to minimize re-association of fast off rate aptamers with the target but not more than makes recovery of the desired nucleic acid ligand from the solution impractical. This concept is described in detail in concurrently filed U.S. application Ser. No. 12/175,434, entitled "Method For Generating Aptamers With Improved Off-Rates", which is incorporated by reference herein in its entirety.

"Tissue target" or "tissue" refers herein to a certain subset of the SELEX targets described above. According to this definition, tissues are macromolecules in a heterogeneous environment. As used herein, tissue refers to a single cell type, a collection of cell types, an aggregate of cells, or an aggregate of macromolecules. This differs from simpler SELEX targets that are typically isolated soluble molecules, such as proteins. In some embodiments, tissues are insoluble macromolecules that are orders of magnitude larger than simpler SELEX targets. Tissues are complex targets made up of numerous macromolecules, each macromolecule having numerous potential epitopes. The different macromolecules which comprise the numerous epitopes can be proteins, lipids, carbohydrates, etc., or combinations thereof. Tissues are a physical array of macromolecules that can be either fluid or rigid, both in terms of structure and composition. Extracellular matrix is an example of a more rigid tissue, both structurally and compositionally, while a membrane bilayer is more fluid in structure and composition. Tissues are typically not soluble and remain in solid phase, and thus partitioning can be accomplished relatively easily. Tissue includes, but is not limited to, an aggregate of cells usually of a particular kind together with their intercellular substance that form one of the structural materials commonly used to denote the general cellular fabric of a given organ, e.g., kidney tissue, brain tissue. The four general classes of tissues are epithelial tissue, connective tissue, nerve tissue and muscle tissue.

Examples of tissues which fall within this definition include, but are not limited to, heterogeneous aggregates of macromolecules such as fibrin clots which are acellular; homogeneous or heterogeneous aggregates of cells; higher ordered structures containing cells which have a specific function, such as organs, tumors, lymph nodes, arteries, etc., and individual cells. Tissues or cells can be in their natural environment, isolated, or in tissue culture. The tissue can be intact or modified. The modification can include numerous changes such as transformation, transfection, activation, and substructure isolation, e.g., cell membranes, cell nuclei, cell organelles, etc.

Sources of the tissue, cell or subcellular structures can be obtained from prokaryotes as well as eukaryotes. This includes human, animal, plant, bacterial, fungal, and viral structures.

As used herein, the term "labeling agent," "label", or "detectable moiety" refers to one or more reagents that can be used to detect a target molecule that is bound to an aptamer. A detectable moiety or label is capable of being detected directly or indirectly. In general, any reporter molecule that is detectable can be a label. Labels include, for example, (i) reporter molecules that can be detected directly by virtue of generating a signal, (ii) specific binding pair members that can be detected indirectly by subsequent binding to a cognate that contains a reporter molecule, (iii) mass tags detectable by mass spectrometry, (iv) oligonucleotide primers that can provide a template for amplification or ligation, and (v) a specific polynucleotide sequence or recognition sequence that can act as a ligand, such as, for example, a repressor protein, wherein in the latter two instances the oligonucleotide primer or repressor protein will have, or be capable of having, a reporter molecule, and so forth. The reporter molecule can be a catalyst, such as an enzyme, a polynucleotide coding for a catalyst, promoter, dye, fluorescent molecule, quantum dot, chemiluminescent molecule, coenzyme, enzyme substrate, radioactive group, a small organic molecule, amplifiable polynucleotide sequence, a particle such as latex or carbon particle, metal sol, crystallite, liposome, cell, etc., which may or may not be further labeled with a dye, catalyst or other detectable group, a mass tag that alters the weight of the molecule to which it is conjugated for mass spectrometry purposes, and the like. The label can be selected from electromagnetic or electrochemical materials. In one embodiment, the detectable label is a fluorescent dye. Other labels and labeling schemes will be evident to one skilled in the art based on the disclosure herein.

A detectable moiety can include any of the reporter molecules listed above and any other chemical or component that can be used in any manner to generate a detectable signal. The detectable moiety can be detected via a fluorescent signal, a chemiluminescent signal, or any other detectable signal that is dependent upon the identity of the moiety. In the case where the detectable moiety is an enzyme (for example, alkaline phosphatase), the signal can be generated in the presence of the enzyme substrate and any additional factors necessary for enzyme activity. In the case where the detectable moiety is an enzyme substrate, the signal can be generated in the presence of the enzyme and any additional factors necessary for enzyme activity. Suitable reagent configurations for attaching the detectable moiety to a target molecule include covalent attachment of the detectable moiety to the target molecule, non-covalent association of the detectable moiety with another labeling agent component that is covalently attached to the target molecule, and covalent attachment of the detectable moiety to a labeling agent component that is non-covalently associated with the target molecule. Universal protein stains are described in detail in U.S. patent application Ser. No. 10/504,696, filed Aug. 12, 2004, entitled "Methods and Reagents for Detecting Target Binding by Nucleic Acid Ligands".

"Solid support" refers herein to any substrate having a surface to which molecules can be attached, directly or indirectly, through either covalent or non-covalent bonds. The substrate materials can be naturally occurring, synthetic, or a modification of a naturally occurring material. Solid support materials include silicon, graphite, mirrored surfaces, laminates, ceramics, plastics (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), germanium, gallium arsenide, gold, silver, etc., either used by themselves or in conjunction with other materials. Additional rigid materials can be considered, such as glass, which includes silica and further includes, for example, glass that is available as Bioglass. Other materials that can be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

The solid support can take any of a variety of configurations ranging from simple to complex and can have any one of a number of shapes, including a strip, plate, disk, rod, particle, including bead, tube, well, and the like. The surface can be relatively planar (e.g., a slide), spherical (e.g., a bead), cylindrical (e.g., a column), or grooved. Exemplary solid supports include microtiter wells, microscope slides, membranes, paramagnetic beads, charged paper, Langmuir-Blodgett films, silicon wafer chips, flow through chips, and microbeads.

As used herein, "partitioning" means any process whereby nucleic acid ligands bound to target molecules can be separated from nucleic acids not bound to target molecules. More broadly stated, partitioning allows for the separation of all the nucleic acids in a candidate mixture into at least two pools based on their relative affinity to the target molecule. Partitioning can be accomplished by various methods known in the art, including filtration, affinity chromatography, liquid-liquid partitioning, HPLC, etc. For example, nucleic acid-protein pairs can be bound to nitrocellulose filters while unbound nucleic acids are not. Columns that specifically retain nucleic acid-target complexes can also be used for partitioning. For example, oligonucleotides able to associate with a target molecule bound on a column allow the use of column chromatography for separating and isolating the highest affinity nucleic acid ligands. Beads upon which target molecules are conjugated can also be used to partition nucleic acid ligands in a mixture. If the beads are paramagnetic, the partitioning can be achieved through application of a magnetic field. Surface plasmon resonance technology can be used to partition nucleic acids in a mixture by immobilizing a target on a sensor chip and flowing the mixture over the chip, wherein those nucleic acids having affinity for the target can be bound to the target, and the remaining unbound or weakly associated nucleic acid ligands can be washed away. Liquid-liquid partitioning can be used as well as filtration gel retardation and density gradient centrifugation. Affinity tags on the target molecules can also be used to separate nucleic acid molecules bound to the tagged target from those free in solution. For example, biotinylated target molecules, along with nucleic acid ligands bound to them, can be sequestered from the solution of unbound nucleic acid sequences using streptavidin paramagnetic beads. In addition to using streptavidin, other related molecules like neutravidin or ExtrAvidin can be used.

In some aspects, it can be desirable to reduce attachment of nucleic acids to an avidin column during the aptamer selection process. A candidate mixture of nucleic acids can be prepared and contacted with a biotinylated target. Those nucleic acids having an increased affinity to the target relative to the candidate mixture will form nucleic acid-target complexes. These complexes can be partitioned from the candidate mixture with an avidin column. The avidin column can contain streptavidin, neutravidin, or ExtrAvidin, for example. The column is washed with a solution containing biotin, causing displacement of nucleic acids bound to the avidin.

As used herein, "photoSELEX" is an acronym for Photochemical Systematic Evolution of Ligands by EXponential enrichment and refers to embodiments of the SELEX process in which photocrosslinking aptamers are generated. In one embodiment of the photoSELEX process, a photoreactive nucleotide activated by absorption of light is incorporated in place of a native base in either RNA- or in ssDNA-randomized oligonucleotide libraries, the nucleic acid target molecule mixture is irradiated causing some nucleic acids incorporated in nucleic acid-target molecule complexes to crosslink to the target molecule via the photoreactive functional groups, and the selection step is a selection for photocrosslinking activity. The photoSELEX process is described in great detail in the PhotoSELEX Patents.

As used herein, "photoaptamer," "photoreactive nucleic acid ligand," and "photoreactive aptamer" are used interchangeably to refer to an aptamer that contains one or more photoreactive functional groups that can covalently bind to or "crosslink" with a target molecule. For example, a naturally occurring nucleic acid residue can be modified to include a chemical functional group that confers photoreactivity upon the nucleic acid residue upon exposure to a radiation source of an appropriate wavelength. In some embodiments, a photoreactive aptamer is identified initially. In other embodiments, an aptamer is first identified and is subsequently modified to incorporate one or more photoreactive functional groups, thereby generating a photoaptamer. In these embodiments, one or more photoreactive nucleic acid residues can be incorporated into an aptamer either by substituting a photoreactive nucleic acid residue in the place of one or more other nucleotides, such as one or more of the thymidine and/or cytidine nucleotides in the aptamer, for example, or by modifying one or more nucleic acid residues to include a photoreactive functional group.

Exemplary photoreactive functional groups that can be incorporated by a photoaptamer include 5-bromouracil, 5-iodouracil, 5-bromovinyluracil, 5-iodovinyluracil, 5-azidouracil, 4-thiouracil, 5-thiouracil, 4-thiocytosine, 5-bromocytosine, 5-iodocytosine, 5-bromovinylcytosine, 5-iodovinylcytosine, 5-azidocytosine, 8-azidoadenine, 8-bromoadenine, 8-iodoadenine, 8-aziodoguanine, 8-bromoguanine, 8-iodoguanine, 8-azidohypoxanthine, 8-bromohypoxanthine, 8-iodohypoxanthine, 8-azidoxanthine, 8-bromoxanthine, 8-iodoxanthine, 5-[(4-azidophenacyl)thio] cytosine, 5-[(4-azidophenacyl)thio]uracil, 7-deaza-7-iodoadenine, 7-deaza-7-iodo guanine, 7-deaza-7-bromoadenine, and 7-deaza-7-bromoguanine.

In addition to these exemplary nucleoside-based photoreactive functional groups, other photoreactive functional groups that can be added to a terminal end of an aptamer using an appropriate linker molecule can also be used. Such photoreactive functional groups include benzophenone, anthraquinone, 4-azido-2-nitro-aniline, psoralen, derivatives of any of these, and the like.

A photoreactive functional group incorporated by a photoaptamer can be activated by any suitable method. In one embodiment, a photoaptamer containing a photoreactive functional group can be crosslinked to its target by exposing the photoaptamer and its bound target molecule to a source of electromagnetic radiation. Suitable types of electromagnetic radiation include ultraviolet light, visible light, X-rays, and gamma rays. Suitable radiation sources include sources that utilize either monochromatic light or filtered polychromatic light.

In one embodiment, a photoreactive nucleotide, such as 4-azido-2-nitro-aniline, for example, can be incorporated into a photoaptamer, and light having a wavelength ranging from about 325 nm to about 470 nm can be used to irradiate the photoaptamer so that it can form a covalent bond to a bound target molecule. Excitation at these wavelengths can be accomplished, for example, with inexpensive light emitting diodes (LEDs) using either a single LED or an array of LEDs, since the power requirements are modest. Nearly monochromatic light having a wavelength ranging from 465 to 475 nm, a 100 degree viewing angle and providing 38 lumens of light is supplied by one or more high-powered LEDs. In the event that a desired photoreactive functional group cannot be excited at a wavelength produced by an LED, appropriate substitution of electron withdrawing or electron donating groups often can be used to modestly shift the excitation wavelength of the photoreactive functional group to enable excitation of the photoreactive functional group at a wavelength produced by an LED.

In one embodiment, a photoreactive nucleotide is incorporated into a photoaptamer, and light having a wavelength ranging from about 300 nm to about 350 nm can be used to irradiate the photoaptamer so that it can form a covalent bond to a bound target molecule.

In one embodiment, a photoreactive nucleotide, such as a 5-iodouracil or a 5-iodocytosine, for example, can be incorporated into a photoaptamer, and light having a wavelength ranging from about 320 nm to about 325 nm can be used to irradiate a photoaptamer so that it can form a covalent bond to a bound target molecule. This combination facilitates selective photocrosslinking of the chromophore-containing photoaptamer to the target molecule without inducing other, non-specific photoreactions. For example, in the case of target protein, any tryptophan residues that are included in the target protein and any thymine and uracil bases that are included in the photoaptamer can also be photoreactive. Since 5-iodouracil or 5-iodocytosine absorbs light having a wavelength of about 325 nm but tryptophan and naturally occurring nucleic acid bases do not, using light of this wavelength permits a selective photoreaction at the 5-iodouracil(s) or 5-iodocytosine(s) within the photoaptamer. Monochromatic light having a wavelength ranging from about 320 nm to about 325 nm can be supplied, for example, by a frequency doubled tunable dye laser emitting light at a wavelength of about 320 nm or by a helium cadmium laser emitting light at a wavelength of about 325 nm.

As used herein, the term "the affinity SELEX process" refers to embodiments of the SELEX process in which non-photocrosslinking aptamers to targets are generated. Photosensitive nucleotides can be used but no photo-activation steps are involved in the affinity SELEX process. In some embodiments of the affinity SELEX process, the target is immobilized on a solid support either before or after the target is contacted with the candidate mixture of nucleic acids. The association of the target with the solid support allows nucleic acids in the candidate mixture that have bound to target to be partitioned from the remainder of the candidate mixture. The term "bead affinity SELEX process" refers to particular embodiments of the affinity SELEX process where the target is immobilized on a bead, for example, before contact with the candidate mixture of nucleic acids. In some embodiments, the beads can be paramagnetic beads. The term "filter affinity SELEX process" refers to embodiments where nucleic acid target complexes are partitioned from candidate mixture by virtue of their association with a filter, such as a nitrocellulose filter. This includes embodiments where the target and nucleic acids are initially contacted in solution, and contacted with the filter, and also includes embodiments where nucleic acids are contacted with target that is pre-immobilized on the filter. The term "plate affinity SELEX process" refers to embodiments where the target is immobilized on the surface of a plate, such as, for example, a multi-well microtiter plate. In some embodiments, the plate is comprised of polystyrene. In some embodiments, the target is attached to the plate in the plate affinity SELEX process through hydrophobic interactions.

In certain aspects, the affinity SELEX process can used in conjunction with the photoSELEX process. Typically, in such embodiments, a candidate mixture comprised of nucleic acids modified with photoreactive functional groups is subjected to several rounds of affinity SELEX followed by photoSELEX.

The present disclosure describes improved SELEX methods for generating nucleic acid ligands that are capable of binding to target molecules and improved photoSELEX methods for generating photoreactive nucleic acid ligands that are capable of both binding and covalently crosslinking to target molecules. The disclosure further describes nucleic acid sequence libraries having expanded physical and chemical properties and their use in SELEX and photoSELEX; methods for increasing the crosslinking efficiencies for photoaptamers; methods for producing photoaptamers having selective modifications that enhance functionality and minimize non-specific photoreactions; and methods for generating truncated nucleic acid ligands from nucleic acid ligands of longer length. The disclosure further describes aptamers and photoaptamers obtained using any of the foregoing methods.

With reference to FIG. 1, the SELEX process generally begins with the preparation of a candidate mixture of nucleic acids of differing sequence. The candidate mixture can include nucleic acid sequences that include two fixed regions (i.e., each of the members of the candidate mixture contains the same sequences in the same location) that flank a variable region on either side. Typically, the fixed sequence regions are selected such that they (a) assist in the amplification steps described below; (b) mimic a sequence known to bind to the target; or (c) enhance the potential of a given structural arrangement of the nucleic acids in the candidate mixture. The variable region of each nucleic acid in the candidate mixture can be completely randomized (i.e., the probability of finding a base at any position being one in four) or only partially randomized (e.g., the probability of finding a base at any location can be selected at any level between 0 and 100 percent). The prepared candidate mixture is contacted with the selected target under conditions that are favorable for binding to occur between the target and members of the candidate mixture. Under these conditions, the interaction between the target and the nucleic acids of the candidate mixture forms aptamer affinity complexes that have the strongest relative affinity between members of the pair. The nucleic acids with the highest affinity for the target are partitioned from those nucleic acids with lesser affinity to the target. Those nucleic acids selected during partitioning as having a relatively high affinity to the target are amplified to create a new candidate mixture that is enriched in nucleic acids having a relatively high affinity for the target. By repeating the partitioning and amplifying steps above, the newly formed candidate mixture contains fewer and fewer unique sequences, and the average degree of affinity of the nucleic acid mixture to the target will generally increase. Taken to its extreme, the SELEX process will yield a candidate mixture containing one or a very small number of unique nucleic acid ligands representing those nucleic acid ligands from the original candidate mixture that have the highest affinity to the target molecule.

The SELEX Patents and the PhotoSELEX Patents describe and elaborate on this process in great detail. These patents include descriptions of the various targets that can be used in the process; methods for the preparation of the initial candidate mixture; methods for partitioning nucleic acids within a candidate mixture; and methods for amplifying partitioned nucleic acids to generate enriched candidate mixtures. The SELEX Patents also describe nucleic acid ligand solutions obtained to a number of different types of target molecules, including protein targets wherein the protein is and is not a nucleic acid binding protein.

A modified SELEX process is described in U.S. patent application Ser. No. 12/175,434, entitled "Method for Generating Aptamers with Improved Off-Rates," filed concurrently herewith and incorporated herein by reference in its entirety. The modification comprises the optional step of introducing a slow off-rate enrichment step prior to partitioning the nucleic acid-target molecule complex from free aptamer. As noted above, the slow off-rate enrichment step depends upon the differing dissociation rates of aptamer affinity complexes, and as such, the duration of the slow off-rate enrichment step is chosen so as to retain a high proportion of aptamer affinity complexes with slow dissociation rates while substantially reducing the number of aptamer affinity complexes with fast dissociation rates. The purpose of the slow off-rate enrichment step is to provide high affinity aptamers with much slower dissociations than can be attained with the previous SELEX processes.

Modified Nucleotides

The present disclosure provides a method for identifying modified nucleic acid ligands that have the ability to interact with target molecules in ways that are enhanced compared to nucleic acid ligands containing unmodified nucleotides. This encompasses nucleic acid sequences comprised of one or more non-naturally occurring nucleotide base(s) that interact in some desired fashion with target molecules. The incorporation of nucleotides modified with functional groups produce nucleic acid ligands with an increased repertoire of structures and interactions and increases the available binding nucleic acid ligands. Various types of functional groups can be incorporated to produce a spectrum of molecular structures and interactions. In some embodiments, the functional groups are selected from those groups shown in FIG. 2.

As used herein "binding" refers to the formation of a non-covalent association between the ligand and the target, although such binding is not necessarily reversible. The terms "nucleic acid-target complex", "nucleic acid-target molecule complex", "complex" or "affinity complex" are used to refer to the product of such non-covalent binding association. As used herein, the phrase "photoaptamer-target complex" refers to the association of a photoaptamer with a chosen target.

In various embodiments, the nucleic acid ligands can be single- or double-stranded RNA or DNA oligonucleotides. The nucleic acid ligands can contain non-standard or modified bases. Further, the nucleic acid ligands can contain any type of modification. As used herein, a "modified base" can include a relatively simple modification to a natural nucleic acid residue, which modification confers a change in the physical properties of the nucleic acid residue. Such modifications include, but are not limited to, modifications at the 5-position of pyrimidines, substitution with hydrophobic groups, e.g., benzyl, iso-butyl, indole, or napthyl, or substitution with hydrophilic groups, e.g., quaternary amine or guanidinium, or more "neutral" groups, e.g., imidazole and the like. Additional modifications can be present in the ribose ring, e.g., 2'-position, such as 2'-amino (2'—NH$_2$) and 2'-fluoro (2'-F), or the phosphodiester backbone, e.g., phosphorothioates or methyl phosphonates.

In various embodiments, a candidate mixture containing a randomized set of nucleic acid sequences containing modified nucleotide bases is mixed with a quantity of the target molecule and allowed to establish binding equilibrium with the target molecule. Once binding equilibrium between the nucleic acid ligand is established with the target molecule the mixture is partitioned. Generally, only some of those nucleic acid ligands that bind with high affinity to the target molecule will efficiently partition with the target.

In various embodiments, the candidate mixture includes nucleic acid sequences having variable regions that include modified groups. The modified groups can be modified nucleotide bases. The variable region can contain fully or partially random sequences; it can also contain subportions of a fixed sequence that is incorporated within the variable region while being retained for appropriate binding of the nucleic acid ligand. The nucleotides within the fixed regions can also contain modified nucleotide bases, or they can contain the standard set of naturally occurring bases.

In some embodiments, amplification occurs after members of the test mixture have been partitioned, and it is the nucleic acid that is amplified. For example, amplifying RNA molecules can be carried out by a sequence of three reactions: making cDNA copies of selected RNAs, using the polymerase chain reaction to increase the copy number of each cDNA, and transcribing the cDNA copies to obtain RNA molecules having the same sequences as the selected RNAs. Any reaction or combination of reactions known in the art can be used as appropriate, including direct DNA replication, direct RNA amplification and the like. The amplification method results in the proportions of the amplified mixture being essentially representative of the proportions of different sequences in the mixture prior to amplification. Many modified nucleotides in a nucleic acid sequence are compatible with enzymatic amplification. Modifications that are not compatible with amplification can be made after each round of amplification, if necessary. Modifications that impact amplification can be determined experimentally if required.

The nucleic acid test mixture can be modified in various ways to enhance the probability of the nucleic acids having facilitating properties or other desirable properties, for example, properties that enhance the interaction between the nucleic acid and the target. Contemplated modifications include modifications that introduce other chemical groups that have the correct charge, polarizability, hydrogen bonding, or electrostatic interaction to enhance the desired ligand-target interactions. Modifications that can enhance nucleic acid binding, for example, include hydrophilic moieties, hydrophobic moieties, rigid structures, functional groups found in proteins such as imidazoles, primary alcohols, carboxylates, guanidinium groups, amino groups, thiols and the like.

A modified nucleotide library for the purpose of this application is any RNA or DNA library that contains nucleotides other than the naturally occurring ones. Suitable modifications include modifications on every residue of the nucleic acid, on a single residue of the nucleic acid, on random residues, on all pyrimidines or all purines, on all occurrences of a specific base (i.e., G, C, A, T or U) in the nucleic acid ligand, or any other modification scheme that can be suitable for a particular application.

As described above, the nucleotides can be modified in any number of ways, including modifications of the ribose and/or phosphate and/or base positions. Certain modifications are described in U.S. Pat. No. 5,660,985 entitled "High Affinity Nucleic Acid Ligands Containing Modified Nucleotides", U.S. Pat. No. 5,428,149 entitled "Method for Palladium Catalyzed Carbon-Carbon Coupling and Products", U.S. Pat. No. 5,580,972 entitled "Purine Nucleoside Modifications by Palladium Catalyzed Methods", U.S. Pat. No. 5,719,273 entitled "Nucleoside modifications by palladium catalyzed methods" all of which are incorporated by reference herein in their entirety. In one embodiment, modifications are those wherein another chemical group is attached to the 5-position of a pyrimidine or the 2' position of a sugar. There is no limitation on the type of other chemical group that can be incorporated on the individual nucleotides. In some embodiments, the resulting modified nucleotide is amplifiable or can be modified subsequent to the amplification steps (see, e.g., U.S. Pat. No. 6,300,074 entitled "Systematic evolution of ligands by exponential enrichment: Chemi-SELEX").

Use of Non-Photoreactive Placeholding Pyrimidines in the Selection of Photoaptamers Photoaptamers can be identified by first identifying an affinity aptamer and substituting in one or more photoreactive nucleotide residues. While some photoaptamers have been identified by this method previously (Willis et al, 1993, Science 262: 1255, Ruckman et al., 1998, JBC 273:20556), such post-SELEX modifications can be detrimental to aptamer affinity to its target. As disclosed herein, when affinity aptamer selection is conducted with a modified non-photoreactive placeholding pyrimidine, such as 5-methyl-dC or thymine, the post-SELEX substitution of a photoreactive pyrimidine for one or more non-reactive placeholding pyrimidines yields a photoaptamer with good photocrosslinking capabilities and limited to no reduction in affinity. Photoreactive 5-bromo-dC or 5-iodo-dC can substitute for 5-methyl-dC (a bromo or iodo for methyl group substitution) without significantly altering target molecule recognition. The corresponding modifications to uracil can also be used. Aptamers that include the nucleotides dA, dG, dT and 5-methyl-dC and that were selected solely on the basis of target affinity and specificity (not photocrosslinking) can be converted to photoaptamers simply by substituting 5-position pyrimidine methyl groups with bromine or iodo groups. Such substitutions are achieved through either enzymatic (PCR or primer extension-based DNA polymerase methods) or synthetic (standard DNA synthesis methods) means. This process is illustrated in Example 4 wherein an endostatin affinity aptamer was selected from a candidate DNA mixture composed of dA, dG, 5-methyl-dC, and dT. A control endostatin affinity aptamer was also selected from a candidate mixture composed of dA, dG, dC, and dT. Both aptamers were Post SELEX-modified to replace either all or 1:3 of the 5-methyl-dC or dC residues with 5-bromo-dC. The results indicated a significant loss of target affinity when aptamer wild-type dC nucleotides were substituted with 5-bromo-dC (replacement of 5-position protons with bromines), but the affinity remained intact when 5-methyl-dC nucleotides were substituted with 5-bromo-dC (replacement of 5-position methyl groups with sterically similar bromines).

Use of Non-Photoreactive Placeholding Pyrimidines and Modified Nucleotides in the Selection of Photoaptamers Modified nucleotides have been used in SELEX experiments previously to impart additional functional characteristics to an affinity aptamer, such as resistance to nuclease degradation with the use of 2'-F, 2'-amino or 2'-O-methyl groups. To date, however, aptamers have not been identified having both photoreactive nucleotides and modified nucleotides, particularly base modified nucleotides. Examples of modified pyrimidines comprising at the C-5 position a chemical moiety can be selected from the group shown in FIG. 2.

One or more photoreactive nucleotides can be substituted into an affinity aptamer selected from a candidate mixture containing non-photoreactive placeholding pyrimidines and the modified pyrimidines described above. The resulting photoaptamer has greater functionality imparted by the modified pyrimidines and retains target affinity because the photoreactive nucleotide substitution is sterically equivalent to the non-photoreactive placeholding pyrimidine. A method for producing such aptamers is illustrated in Example 5 in which P-cadherin and gp130 affinity aptamers are selected having 5-Trp-dU and 5-methyl-dC in the candidate mixture and 5-bromo-dC is substituted for the 5-methyl-dC to yield photoaptamers.

Post SELEX Optimization/Minimization of Photoreactive Nucleotides

Photoaptamers that contain a plurality of photoreactive nucleotides can sometimes non-specifically photocrosslink to non-targets. Therefore, it can be desirable to optimize photoaptamers to have minimal numbers of photoreactive nucleotides. Methods for determining which photoreactive nucleotides crosslink to the target have been employed. The methods include (i) screening synthetic variants of the photo aptamer, such that each BrdU or BrdC position is individually screened for photocrosslinking (with the remaining wild-type BrdU or BrdC residues being replaced with dT or 5-methyl-dC, respectively), and (ii) gel mobility shift-based photocrosslink site identification. Either method permits identification of the one or more photoreactive nucleotides that crosslink to the target. It is often possible to retain those crosslinking photoreactive nucleotides and substitute non-photoreactive cognate nucleotides for the remaining photoreactive nucleotides without affecting target affinity or crosslinking capability. In Example 6, photoaptamers to the protein targets MMP-1 and tPA that were selected from candidate mixtures composed of dA, dG, dC, and 5-bromo-dU were subjected to gel mobility shift-based photocrosslink site identification. The photoaptamers were synthesized with 5-bromo-dU at the identified sites and dT at all other sites that were previously 5-bromo-dU. The resulting photoaptamers displayed affinity and crosslinking abilities essentially equivalent to that of the wild-type parental sequences, but with reduced non-specific binding.

5'-Fixed PhotoSELEX

The present disclosure provides a method for identifying nucleic acid ligands that bind and form a covalent crosslink to their target molecule upon photo-activation of the affinity complex. This method encompasses nucleic acid ligands that bind, photocrosslink, and/or photoinactivate target molecules. In various embodiments, the nucleic acid ligands contain photoreactive groups that are capable of photocrosslinking to the target molecule upon irradiation with light. In other embodiments, the nucleic acid ligands are capable of bond formation with the target in the absence of irradiation.

In various embodiments, the candidate mixture includes nucleic acid sequences with randomized, or variable, regions as well as conserved, or fixed, regions used during amplification. The variable region can contain fully or partially random sequence; it can also contain sub-portions of conserved sequence incorporated within the variable region. The 5' fixed region includes a chemically reactive or a photoreactive group or groups. The reactive group or groups can be placed at the end or anywhere within the 5' fixed region provided that sufficient fixed region exists 3' from the reactive group to ensure efficient annealing of the primers used for amplification. The candidate mixture can also include oligonucleotides containing more than one type of reactive group.

In various embodiments, each oligonucleotide member of the candidate mixture contains at least one chemically reactive or photoreactive group. In one embodiment, the candidate mixture includes a randomized set of nucleic acid sequences containing a photoreactive group or groups at the terminal 5' position. In another embodiment, the photoreactive group or groups is anywhere within the 5' fixed region. In another embodiment, the photoreactive group or groups is anywhere within five residues of the terminal 5' residue.

In various embodiments, the candidate mixture is mixed with a quantity of the target molecule and allowed to establish binding equilibrium with the target molecule. The nucleic acid-target molecule mixture is irradiated with light until photocrosslinking is complete. Only some of those nucleic acids binding tightly to the target molecules will efficiently crosslink with the target.

A photoreactive group can be any chemical structure that contains a photochromophore and that is capable of photocrosslinking with a target molecule. Although referred to herein as a photoreactive group, in some cases, as described below, irradiation is not necessary for covalent binding to occur between the nucleic acid ligand and the target. In some embodiments, the photoreactive group will absorb light of a wavelength that is not absorbed by the target or the non-modified portions of the oligonucleotide and forms a bond with the target upon irradiation of the associated nucleic acid-target molecule complex. The photocrosslink that typically occurs will be the formation of a covalent bond between the associated nucleic acid and the target. However, a tight ionic interaction between the nucleic acid and target can also occur upon irradiation. Photoreactive groups include 5-halo-uridines, 5-halo-cytosines, 7-halo-adenosines, 2-nitro-5-azidobenzoyls, diazirines, aryl azides, fluorinated aryl azides, benzophenones, amino-benzophenones, psoralens, anthraquinones, etc.

In one embodiment, photocrosslinking occurs due to exposure to electromagnetic radiation. Electromagnetic radiation includes ultraviolet light, visible light, X-ray, and gamma ray.

Affinity complexes that do not form covalent crosslinks can be easily disrupted by adjusting the reaction medium to dissociate non-covalent complexes. For example, affinity complexes can be denatured with heat and/or salt. Nucleic acids covalently bound to the target can be separated from free nucleic acids on a nitrocellulose filter or by other partitioning methods known to those skilled in the art. Alternate methods for separating nucleic acids covalently bound to targets from free nucleic acids include gel electrophoresis followed by electroelution, precipitation, differential solubility, and chromatography. The method of choice will depend at least in part on the target molecule of interest. After partitioning, the crosslinked nucleic acids-target molecule complexes are amplified directly. Since the crosslink is sequestered in the 5'-terminal end of the fixed sequence, amplification is unimpeded by the presence of the crosslinked nucleic acid-target molecule. A copy of the sense strand, during either reverse transcription in the case of RNA SELEX or PCR in the case of DNA SELEX, will include sufficient 5'-fixed sequence for efficient PCR amplification.

Complementary nucleic acid copies of the selected RNA sequences can be prepared with an appropriate primer. The cDNA is amplified with a DNA polymerase and a second primer.

In various other embodiments, a limited selection of oligonucleotides using a SELEX method is followed by selection using a photoSELEX method. The initial SELEX selection rounds are conducted with oligonucleotides containing photoreactive groups. After a number of SELEX rounds, photoSELEX is conducted to select oligonucleotides capable of binding the target molecule.

In other embodiments, photoreactive nucleotides can be incorporated into single stranded DNAs and amplified directly with or without the photoreactive nucleotide triphosphate.

In other embodiments, the SELEX method is performed using modified nucleotides to isolate modified nucleic acids that photocrosslink.

In other embodiments, the SELEX method includes a slow off-rate enrichment step to select slow dissociation rate nucleic acids that photocrosslink.

In other embodiments, the SELEX method is performed using modified nucleotides, a slow off-rate enrichment process, and 5'-fixed photoSELEX to generate slow dissociation rate photoaptamers from modified nucleic acids.

Truncation SELEX

The present disclosure provides a method for identifying nucleic acid ligands that can be truncated from the full-length sequence that is used in the SELEX process while maintaining the same activity as the full-length sequence. As described above, the nucleic acids in candidate mixtures generally contain fixed regions that are used as PCR primer sequences in the amplification step for the selected nucleic acid ligands. Frequently these sequences can not be cleaved from the final nucleic acid ligand without impacting performance. Truncation SELEX utilizes the fixed sequences flanking the random regions in the nucleic acids employed in the process. By hybridizing a complementary sequence to one or both of the fixed regions of a nucleic acid sequence that fixed region cannot participate in any intramolecular structures with the random region or the other fixed region of the sequence. Using the SELEX process, aptamers are enriched for activity that depends primarily on the random region sequence and not the hybridized fixed region. For each iteration of the SELEX process, the same fixed region complementary sequence is hybridized to nucleic acids in the candidate nucleic acid mixture prior to contacting the candidate mixture with the target molecule. At the end of the SELEX procedure, nucleic acid sequences are truncated by removing the fixed sequence that was hybridized to a complementary sequence during the process.

It should be noted that there are two possible outcomes from using this method: One outcome is that the fixed regions can be removed as described above. However, another possible outcome is that the aptamer may actually require the presence of both the fixed region(s) and the complementary sequence(s) to achieve full activity. This is now disclosed herein as a second benefit: Independent of whether the fixed region(s) can be removed, aptamers selected using this method, maintain their full activity when hybridized to the complementary sequence(s) used in the SELEX procedure. This enables a number of applications of these aptamers. In one example, the complementary sequences can be attached to a solid support and the aptamer hybridized to that complementary sequence. This provides a method to specifically attach an aptamer to a surface without loss of aptamer function. In a second example, functional groups such as tags and labels can be appended or inserted into the complementary sequence. By hybridizing complementary sequences with these functions groups to the aptamer, these additional functions can be imparted to the aptamer without loss of the originally selected aptamer function.

The hybridization time for complex mixtures of double stranded oligonucleotides is determined using $C_0t$ analysis. A $C_0t$ analysis is performed by denaturing a nucleic acid ligand-enriched mixture obtained by methods described herein, and allowing the denatured mixture to renature in the presence of a fluorescent dye that undergoes an increase in fluorescence intensity when bound to double-stranded nucleic acid. The intensity of the fluorescent signal is monitored to provide hybridization time.

In various embodiments, the candidate mixture is first contacted with the complementary sequence to the 3'-fixed region, forming a stable double stranded 3'-fixed region on each nucleic acid in the candidate mixture. This candidate mixture is contacted with a quantity of the target molecule and allowed to establish binding equilibrium with the target molecule. The remainder of the SELEX process proceeds unchanged. In another embodiment, the candidate mixture is first contacted with the complement sequence to the 5'-fixed region, forming a stable double stranded 5'-fixed region on each sequence in the mixture. In another embodiment, the candidate mixture is first contacted with the complement sequence to both the 5'- and 3'-fixed regions, forming stable double stranded 5'- and 3'-fixed regions on each sequence in the mixture.

In one embodiment, unmodified nucleic acid molecules are used to create the candidate mixture. In another embodiment, modified nucleotides are used to create the candidate mixture.

In yet another embodiment, truncation SELEX is performed using unmodified nucleic acids along with a slow off-rate enrichment process. In another embodiment, truncation SELEX is performed using modified nucleic acids along with a slow off-rate enrichment process.

In yet another embodiment, 5'-fixed photoSELEX is performed along with a 3'-truncation SELEX procedure using unmodified nucleic acids. In another embodiment, 5'-fixed photoSELEX is performed along with a 3'-truncation SELEX procedure using unmodified nucleic acids and a slow off-rate enrichment process. In another embodiment, 5'-fixed photoSELEX is performed along with a 3'-truncation SELEX procedure using modified nucleic acids. In another embodiment, 5'-fixed photoSELEX is performed along with a 3'-truncation SELEX procedure using modified nucleic acids and a slow off-rate enrichment process.

Displacement of Streptavidin Binding Sequences to Improve Aptamer Selection

Streptavidin beads are useful in partitioning reagent aptamers bound to biotinylated proteins from free aptamers during in vitro selection experiments. Problems can arise, however, from aptamers that bind directly to the streptavidin, rather than the biotinylated target of interest. Currently, the streptavidin-binding aptamers are reduced by counter-selection using streptavidin beads, which are discarded prior to incubation with biotinylated proteins. Counter-selection alone however is insufficient to overcome the problem of non-specific binding of aptamers to the streptavidin support and thus there are many targets for which aptamers are difficult to identify using existing in vitro selection strategies with streptavidin beads. Disclosed herein is a new method for the reduction of streptavidin binders during SELEX: biotin washes can be employed during SELEX to remove streptavidin binding nucleic acids. Example 7 illustrates a method for displacing aptamers bound to streptavidin by incorporating biotin washes following capture onto streptavidin beads. Use of this method enables the selection of aptamers to targets that failed previously.

EXAMPLES

The following examples are provided for illustrative purposes only and are not intended to limit the scope of the subject matter described herein and in the appended claims.

Example 1

Generation of Photoaptamers Using 5'-Fixed PhotoSELEX

A. Preparation of Candidate Mixtures

Candidate mixtures containing dATP, dCTP, dGTP, and BndUTP were prepared by polymerase extension of a primer annealed to a biotinylated template (FIGS. 3A-B). For each template, four different forward primers were used, each possessing a unique chromophore at the 5' terminus (FIG. 4). For each candidate mixture, 11 nmol forward primer (with 5' chromophore) and 10 nmol template were combined in 250 μL Primer Extension Buffer (120 mM Tris-HCl, pH 7.8 at 20° C., 10 mM KCl, 6 mM $(NH_4)_2SO_4$, 7 mM $MgSO_4$, 0.1 mg/mL BSA, 0.1% Triton X-100), heated to 95° C. for 5 minutes, and cooled on ice. 125 μL each primer:template mixture was added to a 1 mL extension reaction containing Primer Extension Buffer, 0.125 U/μL KOD XL DNA Polymerase, and 0.5 mM each dATP, dCTP, dGTP, and BndUTP, and incubated at 70° C. for 30 minutes. Each 1 mL reaction was split into four 250 μL aliquots and chilled on ice. Double-stranded product was captured via the template strand biotins by adding 1 mL streptavidin-coated magnetic beads (Magna-Bind-Streptavidin, Pierce, 5 mg/mL in 1M NaCl+0.05% TWEEN-20) to each 250 μL aliquot and incubating at 25° C. for 60 minutes with mixing. Beads were washed three times with 0.5 mL SB17T Buffer (40 mM HEPES, pH 7.5, 120 mM NaCl, 5 mM KCl, 5 mM $MgCl_2$, 1 mM EDTA, 0.05% TWEEN-20). The aptamer strand was eluted from the beads with 1 mL 20 mM NaOH, neutralized with 0.25 mL 80 mM HCl, and buffered with 10 μL 1 M HEPES, pH 7.5. Candidate mixtures were concentrated with a Centricon-30 to approximately 0.2 mL, and quantified by UV absorbance spectroscopy.

B. Preparation of Target Proteins

Untagged target proteins were biotinylated by covalent coupling of NHS-PEO4-biotin (Pierce) to lysine residues. Proteins (300 pmol in 50 μL) were exchanged into SB17T with a Sephadex G-25 microspin column. NHS-PEO4-biotin was added to 1.5 mM and the reaction was incubated at 4° C. for 16 hours. Unreacted NHS-PEO4-biotin was removed with a Sephadex G-25 microspin column.

C. Aptamer Selection with Slow Off-Rate Enrichment Process and Photocrosslinking Selections were performed separately with each candidate mixture, comparing binding between samples with target protein (signal S) and samples without target protein (background B). The first three rounds were performed with selection for affinity (no photocrosslinking); the second and third included slow off-rate enrichment processes. Rounds four through eight included both slow off-rate enrichment processes and photocrosslinking.

For each sample, a 90 μL DNA mixture was prepared in SB17T with 10-20 pmoles candidate mixture (100 pmoles in the first round) and 100 pmoles reverse primer. Samples were heated to 95° C. for 3 minutes and cooled to 37° C. at a rate of 0.1° C./second. Samples were combined with 10 μL protein competitor mixture (0.1% Human Serum Albumin (HSA), 10 μM casein, and 10 μM prothrombin in SB17T), added to 0.5 mg MyOne Streptavidin C1 beads (pre-washed twice with 20 mM NaOH and once with SB17T), and incubated at 37° C. for 5 minutes with mixing. Beads were removed by magnetic separation.

Binding reactions were performed by adding 10 μL target protein (0.5 μM in SB17T) or SB17T to 40 μL DNA mixture and incubating at 37° C. for 30 minutes.

When slow off-rate enrichment process was employed, samples were diluted 20× by adding 950 μL SB17T (preheated to 37° C.), and incubated at 37° C. for 30 minutes prior to capturing complexes.

Complexes were captured on MyOne-SA beads via protein biotins by adding 0.25 mg MyOne-SA beads and incubating at 37° C. for 15 minutes with mixing. Free DNA was removed by washing the beads five times with SB17T. Unless indicated, all washes were performed by resuspending the beads in 100 μL wash solution, mixing for 30 seconds at 25° C., separating the beads with a magnet, and removing the wash solution. The aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 1 μL 0.5 M Tris-HCl, pH 7.5.

When photoselection was employed, the 50 μL binding reactions, (or 1 mL binding reactions after optional slow off-rate enrichment process dilution) were irradiated from above with a high-pressure mercury lamp (Optical Associates, Inc. model 0131-0003-01, 500W, with 310 nm mirror set). Candidate mixtures possessing a 5'-BrdU chromophore were irradiated for 37 seconds, those possessing an ANA chromophore were irradiated for 60 seconds, and those possessing an AQ or psoralen chromophore were irradiated for 10 minutes. An additional filter (5 mm plate glass) was used for the ANA, AQ and psoralen chromophores to eliminate unnecessary, but potentially damaging wavelengths below 320 nm. Complexes were captured as above, and non-crosslinked DNA was removed by washing the beads once with 4 M guanidine-HCl+0.05% TWEEN-20 at 50° C. for 10 minutes, once with 20 mM NaOH at 25° C. for 2 minutes, twice with SB17T, and once with 16 mM NaCl. Crosslinked DNA was not removed from the bead surface for the amplification steps.

D. Aptamer Amplification and Purification

Selected aptamer DNA was amplified and quantified by QPCR. 48 μL DNA was added to 12 μL QPCR Mix (5×KOD DNA Polymerase Buffer, 25 mM $MgCl_2$, 10 μM forward PCR primer, 10 μM biotinylated reverse PCR primer, 5×SYBR Green I, 0.125 U/μL KOD XL DNA Polymerase, and 1 mM each dATP, dCTP, dGTP, and dTTP) and thermal cycled in an a Bio-Rad MyIQ QPCR instrument with the following protocol: 1 cycle of 99.9° C. for 15 sec, 55° C. for 10 sec, 68° C. for 30 min, 30 cycles of 99.9° C. for 15 seconds, and 72° C. for 1 minute. Quantification was done with the instrument software and the number of copies of DNA selected with and without target protein was compared to determine signal/background ratios.

When photoselection was employed, a cDNA copy of the selected DNA was prepared by primer extension on the bead surface. Washed beads were resuspended in 20 μL cDNA extension mix (Primer Extension Buffer containing 5 μM reverse PCR primer, 0.5 mM each dATP, dCTP, dGTP, and dTTP, and 0.125 U/μL KOD XL DNA Polymerase) and incubated at 68° C. for 30 minutes with mixing. The beads were washed 3 times with SB17T, and the aptamer strand was eluted by from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 1 μL 0.5 M Tris-HCl, pH 7.5. The cDNA was amplified and quantified by QPCR as above for the 30 cycles of 99.9° C. for 15 seconds and 72° C. for 1 minute.

Following amplification, the PCR product was captured on MyOne-SA beads via the biotinylated antisense strand. 1.25 mL MyOne-SA beads (10 mg/mL) were washed twice with 0.5 mL 20 mM NaOH, once with 0.5 mL SB17T, resuspended in 1.25 mL 3 M NaCl+0.05% Tween, and stored at 4° C. 25 μL MyOne-SA beads (10 mg/mL in 3 M NaCl) were added to 50 μL double-stranded QPCR product and incubated at 25° C. for 5 minutes with mixing. The beads were washed once with SB17T, and the "sense" strand was eluted from the beads by adding 200 μL 20 mM NaOH, and incubating at 37° C. for 1 minute with mixing. The eluted strand was discarded and the beads were washed 3 times with SB17T and once with 16 mM NaCl.

Aptamer sense strand was prepared with the appropriate chromophore by primer extension from the immobilized antisense strand. The beads were resuspended in 20 μL primer extension reaction mixture (1× Primer Extension Buffer, 5 μM forward primer with appropriate 5' chromophore, 0.5 mM each dATP, dCTP, dGTP, and BndUTP, and 0.125 U/μL KOD XL DNA Polymerase) and incubated at 68° C. for 30 minutes with mixing. The beads were washed 3 times with SB17T, and the aptamer strand was eluted from the beads by adding 85 μL 20 mM NaOH, and incubating at 37° C. for 1 minute with mixing. 80 μL aptamer eluate was transferred to a new tube after magnetic separation, neutralized with 20 μL 80 mM HCl, and buffered with 5 μL 0.1 M HEPES, pH 7.5.

E. Selection Stringency and Feedback

The relative target protein concentration of the selection step was lowered each round in response to the S/B ratio as follows, where signal S and background B are defined in Section C above:

if $S/B < 10$, $[P]_{(i+1)} = [P]_i$ if $10 \leq S/B < 100$, $[P]_{(i+1)} = [P]_i / 3.2$ if $S/B \geq 100$, $[P]_{(i+1)} = [P]_i / 10$ where [P]=protein concentration and i=current round number.

Target protein concentration was lowered by adjusting the mass of target protein beads (and $(His)_6$ beads for background determination) added to the selection step.

After each selection round, the convergence state of the enriched DNA mixture was determined. 5 μL double-stranded QPCR product was diluted to 200 μL with 4 mM $MgCl_2$ containing 1×SYBR Green I. Samples were overlaid with 75 μL silicone oil (Sigma Aldrich) and analyzed for convergence using a $C_0t$ analysis which measures the hybridization time for complex mixtures of double stranded oligonucleotides. The sample is thermal cycled with the following protocol: 3 cycles of 98° C. for 1 minute and 85° C. for 1 minute; 1 cycle of 93° C. for 1 minute and 85° C. for 15 minutes. During the 15 minutes at 85° C., fluorescent images are measured at 5-second intervals. The fluorescence intensity is plotted logarithmically (time) to evaluate the diversity of the sequences.

F. Binding Affinity Activity Assay

Affinities of the enriched libraries were measured using MyOne TALON bead partitioning. DNA was renatured by heating to 95° C. and slowly cooling to 37° C. Complexes were formed by mixing a low concentration of radiolabeled DNA ($\sim 1 \times 10^{-11}$ M) with a range of concentrations of target protein ($1 \times 10^{-7}$ M to $1 \times 10^{-12}$ M final) in SB1 Buffer (described previously), and incubating at 37° C. A portion of each reaction was transferred to a nylon membrane and dried to determine total counts in each reaction. A small amount of 5 mg/mL MyOne TALON beads (Invitrogen) was added to the remainder of each reaction and mixed at 37° C. for one minute. A portion was passed through a MultiScreen HV Plate under vacuum to separate protein-bound complexes from unbound DNA and washed with 100 μL SB1 Buffer. The nylon membranes and MultiScreen HV Plates were phosphorimaged and the amount of radioactivity in each sample quantified using a FUJI FLA-3000. The fraction of captured DNA was plotted as a function of protein concentration and a non-linear curve-fitting algorithm was used to extract equilibrium binding constants ($K_d$ values) from the data. NT indicates that the enriched library for a particular base composition did not appear to have changed from the original candidate mixture, as determined by $C_0t$ analysis (described previously), and was therefore Not Tested (NT). The following table, Table 1, summarizes the dissociation constants obtained using the photoSELEX protocol.

TABLE 1

Equilibrium dissociation constants of the enriched libraries selected with different chromophores, reported in units of molarity.

| Target Protein | BrdU | AQ | ANA | Psor |
|---|---|---|---|---|
| β-catenin | $2.7 \times 10^{-8}$ | $3.6 \times 10^{-9}$ | $1.1 \times 10^{-9}$ | $1.6 \times 10^{-9}$ |
| bFGF | $3.1 \times 10^{-8}$ | $5.7 \times 10^{-10}$ | $7.1 \times 10^{-10}$ | $5.1 \times 10^{-10}$ |
| CMP-SAS | X | $6.2 \times 10^{-9}$ | $7.3 \times 10^{-9}$ | $4.9 \times 10^{-8}$ |
| endostatin | $1.3 \times 10^{-9}$ | $8.7 \times 10^{-10}$ | $8.8 \times 10^{-10}$ | $1.3 \times 10^{-9}$ |
| IL-6 | $1.0 \times 10^{-9}$ | $5.4 \times 10^{-10}$ | $4.0 \times 10^{-10}$ | X |
| myelo-peroxidase | $6.0 \times 10^{-10}$ | $2.8 \times 10^{-10}$ | $5.0 \times 10^{-10}$ | $1.5 \times 10^{-10}$ |
| SDF-1β | $8.1 \times 10^{-10}$ | $5.7 \times 10^{-10}$ | $3.8 \times 10^{-10}$ | X |
| TIMP-1 | $5.2 \times 10^{-9}$ | $7.3 \times 10^{-9}$ | $8.9 \times 10^{-9}$ | X |
| VEGF | $7.2 \times 10^{-10}$ | $4.2 \times 10^{-9}$ | $5.5 \times 10^{-10}$ | X |
| vWF | $2.6 \times 10^{-8}$ | $8.8 \times 10^{-9}$ | $8.1 \times 10^{-9}$ | X |

Measurements were not made on libraries that failed to converge (indicated with an x).

G. Crosslink Activity Assay

Figure 5:
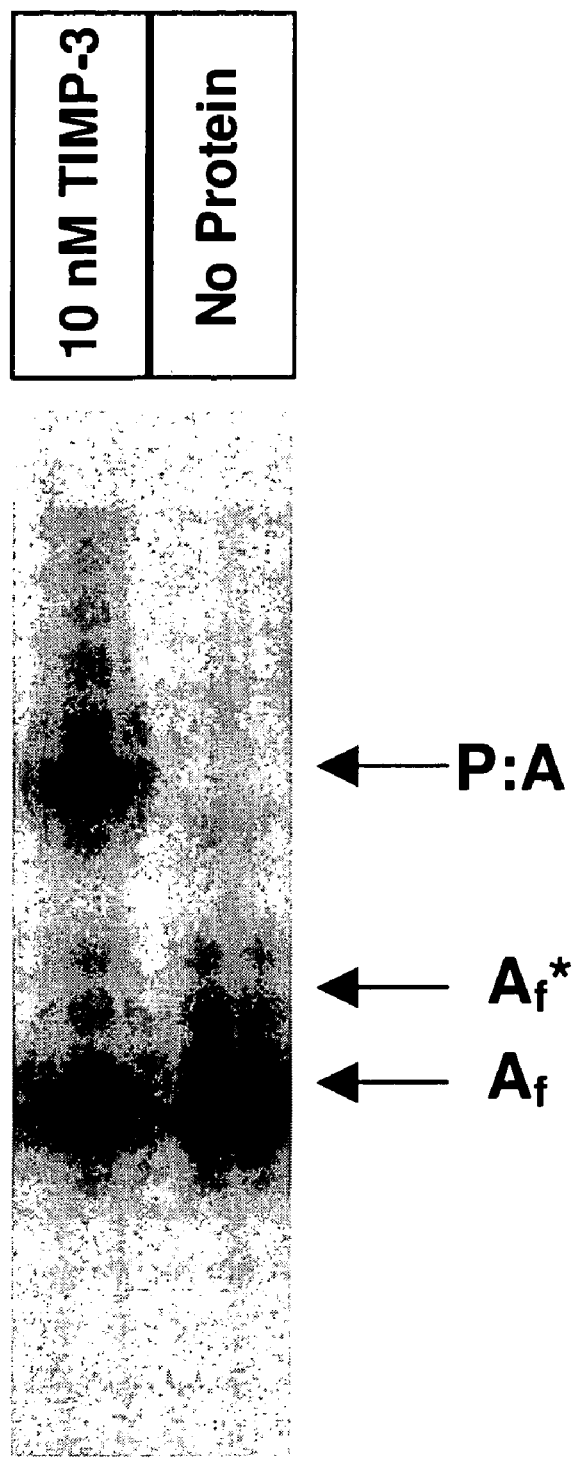
FIG. 5 shows a PAGE analysis of crosslink activity of TIMP-3 5'ANA/BndU enriched library using 5'-Fixed PhotoSELEX. The gel illustrates the separation of free aptamer ($A_f$), intramolecular crosslinked aptamer ($A_f^*$), and crosslinked protein:aptamer complexes (P:A).

The crosslink yield of enriched libraries was determined by measuring the percent of DNA crosslinked to protein under conditions of saturating protein and light. Radiolabeled DNA (50 pM) was mixed with reverse primer (16 nM) in SB17T, heated to 95° C. for 3 minutes, and cooled to 37° C. at 0.1° C./second. Target protein was added to the DNA mix to a final concentration of 10 nM and incubated at 37° C. for 30 minutes. Control samples with no protein were simultaneously prepared. Samples were crosslinked with the chromophore-specific conditions described above, but with a saturating dose (6 minutes for BrdU, 10 minutes for ANA, and 30 minutes for AQ and Psor). Samples were analyzed by denaturing PAGE, FIG. 5, and quantified and the results are tabulated in Table 2.

TABLE 2

Crosslink yields of the enriched libraries selected with different chromophores, reported in units of percent of total DNA crosslinked to protein.

| Target Protein | BrdU | AQ | ANA | Psor |
|---|---|---|---|---|
| β-catenin | 15 | 9 | 8 | 1 |
| bFGF | 4 | 9 | 15 | 4 |
| CMP-SAS | X | 3 | 5 | 2 |
| endostatin | 2 | 1 | 18 | 3 |
| IL-6 | 0 | 5 | 9 |  |
| myeloperoxidase | 4 | 13 | 9 | 8 |
| SDF-1β | 8 | 10 | 17 | X |
| TIMP-1 | 1 | 4 | 2 | X |

TABLE 2-continued

Crosslink yields of the enriched libraries selected with different chromophores, reported in units of percent of total DNA crosslinked to protein.

| Target Protein | BrdU | AQ | ANA | Psor |
|---|---|---|---|---|
| VEGF | 1 | 1 | 4 | X |
| vWF | 2 | 2 | 7 | X |

Measurements were not made on libraries that failed to converge (indicated with an X).

Example 2

Generation of a Truncated Aptamer to β-Catenin Using Truncation SELEX

A. Truncation SELEX Protocol.

Truncation of the selected aptamers is facilitated by appropriation of the 3' terminal fixed sequence to preclude its involvement in the active binding site. This is accomplished by hybridizing an oligonucleotide complementary to the 3' fixed sequence during the aptamer selection step of the SELEX process. Example 1 (above) describes the 5'-fixed photoSELEX protocol used here to the target protein β-catenin.

B. Truncation Affinity Assay

A photoaptamer (2092-68) to β-catenin whose sequence is displayed in FIG. 6, was prepared with and without the 3'-fixed region sequence by standard DNA synthesis techniques. Radiolabeled aptamer (100 μM) was denatured and renatured as described above, with, or without a 100-fold excess of unlabeled 3' primer. The samples were incubated with or without 10 nM β-catenin protein in SB17 for 30 minutes at 37° C., after which complexes were crosslinked by irradiation with an OAI Hg lamp (Optical Associates, Inc. model 0131-0003-01, 500W, with 310 nm mirror set) for 10 minutes at 37° C. Samples were mixed with 2× formamide loading buffer, heated for 10 minutes at 70° C., and loaded on a 10% polyacrylamide TBE-urea gel. Phosphorimages were collected with a FUJI FLA-3000 FIG. 7A. Crosslink activity was determined for each sample by quantifying the free aptamer and aptamer:protein signals with FUJI ImageGauge image analysis software and calculating the percent of total DNA crosslinked with target protein and subtracting the percent crosslinked without protein.

FIG. 7B shows that the crosslink activity was 13% when the 3' fixed region was present (2092-68_5) and the 3' primer was annealed. In the absence of the annealed 3' primer, crosslink activity dropped to 3%, but returned to full activity when the 3' fixed region was removed (2092-68_6), suggesting the 3' fixed region interfered with the structure of the active aptamer unless it was sequestered by an annealed primer or removed entirely.

Example 3

Identification of the Photocrosslinked Nucleotide within a Photoaptamer Sequence A. Random DNA Library Preparation Random DNA libraries with novel dT analogs were prepared in vitro by primer extension of an antisense template oligonucleotide consisting of a 40 nucleotide random sequence cassette flanked by 18-nucleotide fixed sequence cassettes for primer binding, and a 5' terminal biotin cassette for immobilization (FIG. 8). 3 nmol template oligo (AB)₂- anti-40N48.7 and 4.8 nmol primer (AT)$_4$-5P48 were heated to 95° C. in 50 μL 1×KOD Polymerase Buffer, cooled to ambient temperature, and added to a 300 μL mixture containing 1×KOD Polymerase Buffer, 0.2 mM each dATP, dCTP, dGTP, and dTTP analog, and 0.025 U/μL KOD XL DNA Polymerase, and incubated for 30 minutes at 70° C. Streptavidin-coated paramagnetic beads (Pierce MagnaBind-Streptavidin, hereinafter referred to as MagnaBind-SA) were prepared by washing 3 times with 5M NaCl and resuspending in 1.25M NaCl to 5 mg/mL. Capture of the biotinylated dsDNA product of the extension reaction was done by adding 1.2 mL SA beads (6 mg) to 300 μL DNA library reaction and incubating for 5 minutes at 37° C. with constant mixing. Following capture, the beads were washed 3 times with SB1T (SB1 (40 mM HEPES, pH 7.5, 120 mM NaCl, 5 mM KCl, 1 mM CaCl$_2$, 1 mM MgCl$_2$) with 0.05% TWEEN-20), and the non-biotinylated strand was eluted by incubating the beads in 1.6 mL 20 mM NaOH for 2 minutes at ambient temperature with constant mixing. The 1.6 mL eluate was neutralized with 0.4 mL 80 mM HCl and 15 μL 1M HEPES, pH 7.5 and concentrated by Centricon-30 to a final volume of 100 μL. The concentration of DNA was determined spectrophotometrically. Typical yields were 1-2 nmoL of single-stranded random DNA library.

B. Aptamer Partitioning—(His)$_6$-Tagged Protein Immobilized on MyOne TALON Beads Target protein beads were prepared by capturing (His)$_6$-tagged proteins on MyOne TALON paramagnetic beads. 20 mg MyOne TALON beads (500 μL of 40 mg/mL) were washed 3 times with 500 μL B/W Buffer (300 mM NaCl, 50 mM NaH$_2$PO$_4$/Na$_2$HPO$_4$, pH 8.0, 0.01% TWEEN-20) and resuspended in 2 mL B/W Buffer to 10 mg/mL. 120 μL protein (0.4 mg/mL) was added to 120 μL beads and incubated at ambient temperature for 30 minutes with constant mixing. Uncaptured protein was removed by washing the beads 3 times with 200 μL B/W Buffer and once with SB1T, and the beads were resuspended to a final volume of 200 μL SB1T. Control beads were prepared as above with (His)$_6$ peptide. Partitioning was done by capturing high affinity sequences on the target beads and washing extensively to remove unbound or weakly bound sequences. Selections were performed by combining 100 pmol DNA library and 0.3 mg target beads in 100 μL MyOne TALON Selection Buffer (SB1 containing 0.025% TWEEN-20, 0.01% HSA, 1 μM casein, 1 μM prothrombin, and 1 nmol oligo anti-His$_6$). Prothrombin is added to prevent the selection of relatively abundant sequences adopting a G-quartet conformation known to bind prothrombin in serum and plasma samples. Oligo anti-His$_6$ (FIG. 8) is the complementary sequence of a known aptamer that binds the (His)$_6$ domain of tagged proteins, and inactivates those aptamers by annealing. A separate selection reaction was done for each uniquely modified DNA library. Reactions were incubated for 10 minutes at 37° C. with constant mixing. Unbound DNA was removed by washing the beads 5 times at 37° C. with 100 μL Wash Buffer (SB1T containing 0.1 mg/mL herring sperm (hs) DNA). hsDNA was added to prevent rebinding of sequences that dissociate quickly from the beads. Bound aptamers were eluted from the beads by incubating for 5 minutes at 37° C. with 100 μL Elution Buffer (SB1T containing 2M Guanidinium-HCl) and collecting the eluate. Aptamer was further purified by capturing on primer beads (paramagnetic beads coated with an oligo complementary to the 3' fixed sequence cassette of the random library, see FIG. 8) and washing. Primer beads were purchased from Invitrogen and prepared by washing 10 mg beads once each with 1 mL 20 mM NaOH and SB1T, and resuspending in 2.5 mL 5M NaCl (to a final concentration of 4 mg/mL). 0.1 mg primer beads were added to 100 μL eluate, incubated for 15 minutes at 50° C. with constant mixing, and washed 5 times at ambient temperature with SB1T. Annealed aptamer was eluted from the primer beads by incubating with 80 μL 20 mM NaOH for 2 minutes at ambient temperature with constant mixing. The eluate was collected and neutralized with 20 μL 80 mM HCl.

C. Aptamer Partitioning—Protein Capture by ZORBAX Resin

Selections were performed by combining 100 pmol DNA library and 10 μg target protein in 100 μL ZORBAX Selection Buffer (SB1 containing 0.002% TWEEN-20) and incubating for 30 minutes at 37° C. A separate selection reaction was done for each uniquely modified DNA library. Protein:DNA complexes were captured by adding 10 μL ZORBAX resin (400 mg/mL in dH$_2$O) and incubating for 1 minute at 37° C. with constant mixing. Unbound DNA was removed by passing the mixture through a MultiScreen HV Plate under vacuum and washing once with 200 μL ZORBAX Selection Buffer. Washed resin was resuspended in 50 μL dH$_2$O and transferred to a 96-well plate. Bound aptamer was eluted from the resin by incubating for 10 minutes at 95° C., and cooling to ambient temperature. ZORBAX resin was removed by passing the mixture through a MultiScreen HV Plate fitted over a collection plate and centrifuging. Subsequent selections included a depletion step prior to selection to remove ZORBAX resin binders from the library. A selection reaction was prepared without protein, ZORBAX resin was added, and unbound DNA was recovered by passing the mixture through a MultiScreen HV Plate fitted over a collection plate and centrifuging as described above.

D. Aptamer Partitioning—Complex Retention by Microcon YM-100 Filtration

Selections were performed by combining 100 pmol DNA library and 10 μg target protein in 100 μL SB1T and incubating for 30 minutes at 37° C. The DNA library used with this partition method was designed as above but with an 80-nucleotide random cassette. A separate selection reaction was done for each uniquely modified DNA library. Protein:DNA complexes were captured by passing the mixture through a Microcon YM100 MWCO filter by centrifugation at 37° C. for 8 minutes at 500×g. Filters were first prewashed by centrifugation with 200 μL SB1T. Unbound DNA was removed by washing the retained complexes 3 times with 200 μL SB1T. Bound aptamer was collected by resuspending the retained complexes in 100 μL dH$_2$O, inverting the filter cartridge, and centrifuging at 37° C. for 1 minute at 500×g.

E. Aptamer Amplification and Quantification

Quantitative PCR was employed to both amplify the selected DNA and quantify the amount selected each round. 60 μL QPCR reactions were prepared containing 48 μL selected DNA, 1×KOD DNA Polymerase Buffer, 0.2 mM each dATP, dGTP, dCTP, and dTTP, 2 μM 5' primer (AT)$_4$-5P48, 2 μM 3' primer (AB)$_2$-(T)$_8$-3P7, 0.025 U/μL KOD XL DNA Polymerase, 1×SYBR Green 1, and 5 mM additional MgCl$_2$. Control reactions containing known quantities of template were also prepared. Amplification was performed with an ABI5700 Sequence Detection System by thermal cycling 1 time at 99.9° C. for 15 seconds, 55° C. for 10 seconds, and 68° C. for 30 minutes, followed by 30 times at 99.9° C. for 15 seconds, 55° C. for 10 seconds, and 68° C. for 60 seconds. The addition of SYBR Green 1 permits the monitoring of product formation by the ABI5700 and, when compared with the control reactions, the quantification of template in each reaction. Double-stranded PCR product was captured on SA (streptavidin) beads via the 5' terminal biotins of the antisense strand. 50 μL PCR product were incubated with 25 μL SA beads for 5 minutes at 37° C. with constant mixing, and washed once with 100 μL SB1T. The non-biotinylated sense strand was removed by washing once with 100 μL 20 mM NaOH, three times with 100 μL SB1T, and once with 100 μL 16 mM NaCl. The beads were resuspended in a 20 μL primer extension reaction mixture containing 120 mM Tris-HCl, pH 7.8 at 20° C., 10 mM KCl, 6 mM $(NH_4)_2SO_4$, 7 mM $MgSO_4$, 0.1% Triton X-100, 0.1 mg/mL BSA, 5 μM 5' primer $(AT)_4$-5P48, 0.5 mM each dATP, dCTP, dGTP, and dTTP analog, and 0.025 U/μL KOD XL DNA Polymerase. Reactions were incubated for 30 minutes at 68° C. with constant mixing, and the beads were washed three times at ambient temperature with 100 μL SB1T. The aptamer strand was eluted from the beads by incubating with 80 μL 20 mM NaOH for 2 minutes at ambient temperature with constant mixing. The eluate was collected and neutralized with 20 μL 80 mM HCl and 5 μL 100 mM HEPES, pH 7.5.

F. Selection Strategy

Two samples were prepared in each round of the selection step: one containing the target protein, and another containing either a tag protein or no protein. The number of copies of DNA selected each round in the presence (signal) and absence (background) of target protein were calculated from the QPCR results and compared. If signal/background >100, the amount of protein beads used in the subsequent selection was reduced 10×. If 100>signal/background >10, the amount of protein beads used in the subsequent selection was reduced 3×. If signal/background <10, the amount of protein beads used in the subsequent selection was unchanged. Rounds of selection were continued in this manner until libraries converged as determined by the complexity assay described below.

G. Determination of Library Complexity

Library complexity is determined by measuring rates of annealing of complementary strands after denaturation. Renaturation rates are second order with respect to the concentration of each strand. Highly converged pools with many copies of a small number of different sequences will have high concentrations of each strand and will renature more quickly than poorly converged pools. Renaturation was measured by SYBR Green 1 binding to double-stranded DNA using a custom thermalcycler equipped with a CCD camera. 5 μL PCR product was mixed with 195 μL 4 mM $MgCl_2$ containing 1×SYBR Green 1 and covered with 75 μL silicon oil. Samples were thermal cycled 3 times at 98° C. for 15 seconds and 85° C. for 60 seconds, and once at 98° C. for 15 seconds and 85° C. for 15 minutes. During the 15 minute incubation at 85° C., fluorescent signal intensity was measured by the CCD camera and plotted as a function of time. This graphical representation of reannealing rates shows the convergence of a single sample over several SELEX rounds, or permits a comparison of the convergence states of a set of different samples in a single round.

H. Affinity Assay—MyOne TALON Bead Partition

In a 60 μL reaction, a low concentration of radiolabeled DNA ($1\times10^{-11}$ M) was mixed with a range of concentrations of target protein ($1\times10^{-7}$ M to $1\times10^{-12}$ M) in SB1T and incubated for 30 minutes at 37° C. A 5 μL aliquot of each sample, representing ⅛ of the total reaction, was transferred to a nylon membrane and dried. 10 μL MyOne TALON beads (10 mg/mL in SB1T) were added to the remaining 55 μL and incubated for 1 minute at 37° C. with constant mixing. 47 μL were passed through a MultiScreen HV Plate under vacuum to separate bound complexes from unbound DNA, and washed with 100 μL SB1T. Both the nylon membrane and MultiScreen HV Plate were phosphorimaged and the amount of radioactivity in each sample was quantified using a FUJI FLA-3000. The fraction of captured DNA was plotted as a function of protein concentration and a non-linear curve-fitting algorithm was used to extract equilibrium binding constants ($K_d$ values) from the data. Binding isotherms of converged libraries were compared with those of appropriate random libraries to determine the extent of enrichment. Converged libraries with $K_d$ values at least 10× better than random were further evaluated.

I. Affinity Assay—ZORBAX Resin Partition

In a 60 μL reaction, a low concentration of radiolabeled DNA ($1\times10^{-11}$ M) was mixed with a range of concentrations of target protein ($1\times10^{-7}$ M to $1\times10^{-12}$ M) in ZORBAX Selection Buffer and incubated for 30 minutes at 37° C. A 5 μL aliquot of each sample, representing ⅛ of the total reaction, was transferred to a nylon membrane and dried. 5 μL ZORBAX resin (400 mg/mL in water) was added to the remaining 55 μL and incubated for 1 minute at 37° C. with constant mixing. 44 μL were passed through a MultiScreen HV Plate under vacuum to separate bound complexes from unbound DNA, and washed with 100 μL ZORBAX Selection Buffer. Both the nylon membrane and MultiScreen HV Plate were phosphorimaged and the amount of radioactivity in each sample was quantified using a FUJI FLA-3000. The fraction of captured DNA was plotted as a function of protein concentration and a non-linear curve-fitting algorithm was used to extract equilibrium binding constants ($K_d$ values) from the data. Binding isotherms of converged libraries were compared with those of appropriate random libraries to determine the extent of enrichment. Converged libraries with $K_d$ values at least 10× better than random were further evaluated.

J. Sequence Determination and Analysis and Aptamer Synthesis

Sequences were determined and analyzed in accordance with methods known in the art.

K. Crosslink Assay—PAGE Partition

In a 10 μL reaction, a low concentration of radiolabeled DNA ($1\times10^{-9}$ M) was mixed with an excess of target protein ($1\times10^{-7}$ M) in SB1T and incubated for 30 minutes at 37° C. Samples were irradiated with 1J of light (308 nm, 200 Hz using a HeNe excimer laser source) and diluted 2× in PAGE loading dye (98% formamide, 0.2% SDS, 20 mM $Na_2EDTA$, 0.02% each bromophenol blue, xylene cyanol, orange G). 10 μL samples were heated for 10 minutes at 70° C. and analyzed by denaturing PAGE using 8% polyacrylamide, 8M urea TBE gels. Gels were imaged with a FUJI FLA-3000 in phosphorimage mode and the percent of total aptamer migrating as crosslinked protein-aptamer complex were determined.

L. Gel-Mobility Shift-Based Photocrosslink Site Identification Protocol

Aptamer sequences for photocrosslink site identification experiments can be produced either enzymatically with an appropriate DNA polymerase or synthetically. The aptamer sequence can be prepared with all dT positions substituted with 5-bromo-dU, or with all 5-methyl-dC positions substituted with 5-bromo-dC (although partial substitutions can also be effective). The aptamer is either 5' or 3' end-labeled (with $^{32}P$, for example) using standard polynucleotide kinase or terminal nucleotidyl transferase methods, respectively. The radiolabeled photoaptamer (approximately $1\times10^{-9}$ M) is mixed with an excess of target protein in the appropriate reaction buffer and incubated at 37° C. for 30 minutes. The reaction is irradiated with 0.4-1.0 J of 308 nm light (200 Hz from a HeNe excimer laser source). An equal volume of denaturing PAGE loading dye (98% formamide, 0.2% SDS, 20 mM $Na_2EDTA$, 0.02% each bromophenol blue, xylene cyanol, orange G) is added and the mixture is heated at 70° C. for 10 min. Photocrosslinked complexes are separated from non-crosslinked DNA denaturing PAGE electrophoreses (8% polyacrylamide, 8 M urea, 1×TBE gel). The complexes are visualized by imaging with a FUJI FLA-3000 in phosphorimager mode. A gel slice containing the complexes is excised and the complexes are recovered from the gel slice and purified using standard molecular biology techniques.

To permit identification of the photocrosslinked nucleotide, the DNA component of the purified, radioactively end-labeled photoaptamer-target complexes is fragmented by treatment with piperidine. BrdU and BrdC positions are hypersensitive to cleavage when exposed to piperidine, resulting in a ladder of end-labeled DNA fragments. Because fragments that include the photocrosslinked protein are mobility shifted when the reaction products are electrophoresed on a sequencing gel, while non-protein-crosslinked fragments are not, the photocrosslinked nucleotide position can be readily identified. Typical piperidine cleavage reactions involve incubating the photocrosslinked complexes (or non-photocrosslinked control DNA) in 10% v/v piperidine, 10 mM EDTA at 95° C. for 45 min. Following this incubation, five volumes of water are added (to assist in evaporation of piperidine) to the reaction and the sample is dried in a vacuum centrifuge. The reaction products are suspended in a denaturing PAGE loading dye (98% formamide, 0.2% SDS, 20 mM Na$_2$EDTA, 0.02% each bromophenol blue, xylene cyanol, orange G) and the sample is heated at 70° C. for 10 min. The denatured sample is subjected to standard denaturing PAGE on a sequencing length and thickness gel. The separated fragments are visualized by imaging with a FUJI FLA-3000 in phosphorimager mode and the transition between non-mobility-shifted and mobility-shifted cleavage products is identified as the photocrosslinked nucleotide position. Because the photocrosslinked position is also sensitive to piperidine, the largest non-mobility shifted fragment terminates at the photocrosslinked nucleotide.

M. Optional Alternative Photocrosslink Site Identification Protocol

As above, except digest protein component of DNA-protein conjugates with proteinase K (other proteinases, or a proteinase cocktail, would also be effective) immediately prior to piperidine treatment. Proteinase digestion yields a crosslinked small peptide that is generally sufficient to provide a gel mobility shift and, for certain aptamers-protein complexes, may produce clearer results. The purified photoaptamer-target complexes are dried in a vacuum centrifuge and suspended in a 4-µL reaction mixture consisting of: 1 mg/mL proteinase K, 2 M urea, 0.5% w/v SDS, and 20 mM sodium phosphate, pH 9.0. Following an incubation at 60° C. for 20 min, the following piperidine reaction components are added: 1 µL 100 mM EDTA, 4 µL water, and 1 µL piperidine. The piperidine reaction parameters and analysis method are as described above.

Example 4

Replacement of 5-Methyl-dC with BrdC Maintains High Affinity Binding

Figure 9:
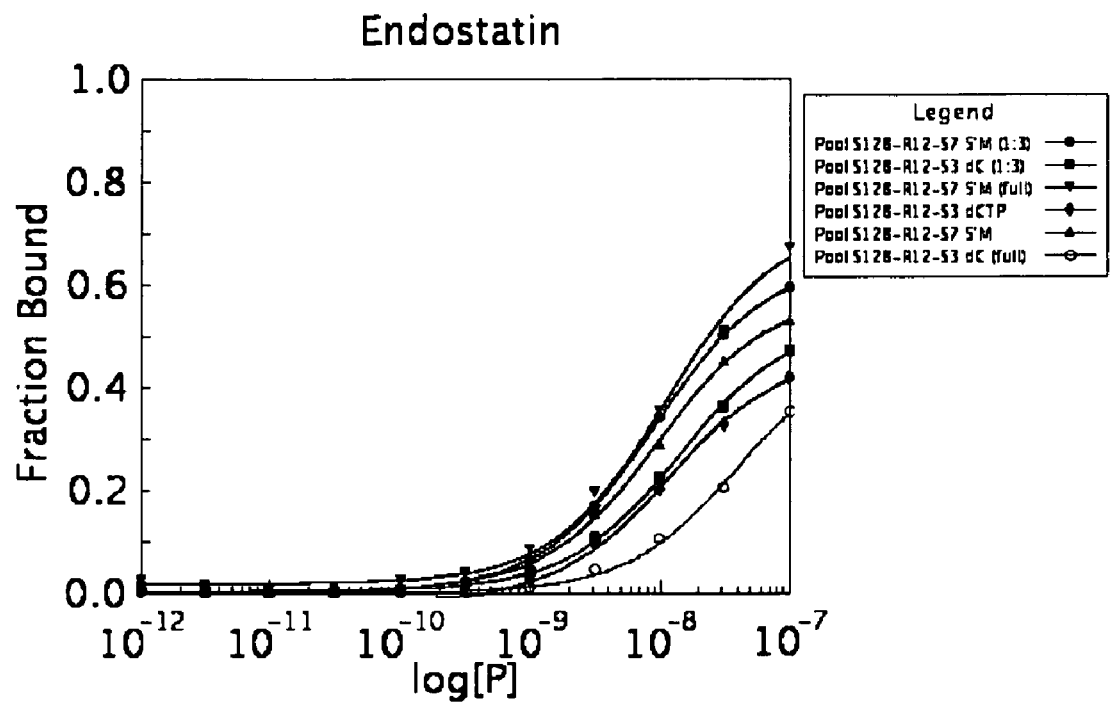
FIG. 9 depicts equilibrium binding curves for two enriched libraries prepared with different ratios of 5-MedC and 5-BrdC. Log [P] represents the concentration of endostatin protein in molarity. (● 5-MedC Pool 5128-R12-S7: C positions=1:3 ratio of 5-BrdC:5-MedC (1:3), ■ dC Pool S128-R12-S3: C positions=1:3 ratio of 5-BrdC:dC, ▼ 5-MedC Pool S128-R12-S7: C positions =all 5-BrdC, ◆ dC Pool S128-R12-S3: C positions =all dC, ▲ 5-MedC Pool S128-R12-S7: C positions =all 5-MedC, ○ dC Pool S128-R12-S3: C positions =all 5-BrdC).

Endostatin aptamer populations composed of either dA, dG, dC, and dT, or dA, dG, 5-methyl-dC, and dT, were affinity-selected by the Zorbax affinity SELEX method described above for the purpose of evaluating the potential of 5-methyl-dC as a steric placeholder for BrdC. The selected high affinity populations were prepared enzymatically as (1) the wild-type sequences (S128-R12-S3 dCTP and S128-R12-S7-5'M, respectively), (2) with each dC or 5-methyl-dC nucleotide position substituted with a bromo-dC nucleotide (S128-R12-S3 dC full and S128-R12-S7-5'M full, respectively), or (3) with approximately one-third (random positions) of the dC or 5-methyl-dC nucleotide positions substituted with a bromo-dC nucleotide (S128-R12-S3 dC 1:3 and S128-R12-S7-5'M 1:3, respectively). As shown in FIG. 9, these results demonstrate a significant reduction in target affinity when aptamer wild-type dC nucleotides are substituted with bromo-dC (replacement of 5-position protons with a bromines), but not when aptamer wild-type 5-methyl-dC nucleotides are substituted with bromo-dC (as with bromo-dU for dT substitutions, a replacement of 5-position methyl groups with sterically similar bromines).

Example 5

Conversion of High Affinity Aptamers to P-Cadherin and gp130 into Photoaptamers Capable of Forming a Covalent Crosslink with a Target Protein (His)$_6$-P-cadherin and (His)$_6$-gp130 Target Proteins Partitioned with TALON Beads A. Selections A random DNA library was prepared, composed of dATP, dCTP, dGTP, and a 5-TrpdUTP. In the first selection round, 0.3 mg MyOne TALON beads loaded with target protein (P-cadherin/IgG1-Fc/His$_6$ or gp130/IgG1-Fc/His$_6$) were mixed with 100 pmoles of random DNA library in selection buffer (SB1T) at 37° C. Equilibrium mixtures were washed to remove unbound DNA, protein:aptamer complexes were eluted with guanidinium-HCl, and the aptamer components were quantified and amplified by QPCR. Subsequent selection rounds were performed with 10 pmoles DNA library. Each round, values of DNA copies selected with beads coated with target protein (signal) were compared with those selected with beads coated with (His)$_6$ peptide (background) to determine the amount of protein beads to use for the subsequent selection round using the following guidelines:

If: Then:
S/B>100 adjust amount of target beads 10-fold lower than previous round
100>S/B>10 adjust amount of target beads 3.2-fold lower than previous round
S/B<10 do not adjust amount of target beads Target bead adjustments for each round are listed in Table 3. Background values did not increase for any of the libraries over the eight selection rounds, suggesting aptamers that bind the TALON beads or the (His)$_6$ domain of the target protein were not being selected.

TABLE 3

Relative protein concentrations used in each selection round for each protein target.

| | P-cadherin | | gp130 | |
|---|---|---|---|---|
| Round | [P]r | S/B | [P]r | S/B |
| 1 | 1 | 22.8 | 1 | 7.0 |
| 2 | $3.2 \times 10^{-1}$ | 124.0 | 1 | 193.3 |
| 3 | $1.0 \times 10^{-1}$ | 73.7 | $3.2 \times 10^{-1}$ | 558.5 |
| 4 | $3.2 \times 10^{-2}$ | 1172.9 | $3.2 \times 10^{-2}$ | 779.1 |
| 5 | $3.2 \times 10^{-3}$ | 731.9 | $3.2 \times 10^{-3}$ | 37.3 |
| 6 | $3.2 \times 10^{-4}$ | 1484.9 | $1.0 \times 10^{-3}$ | 2568.3 |
| 7 | $3.2 \times 10^{-5}$ | 163.6 | $1.0 \times 10^{-4}$ | 15.9 |
| 8 | $1.0 \times 10^{-5}$ | 4.3 | $3.2 \times 10^{-5}$ | 57.4 |

[P]r is the concentration of target protein used in the SELEX round relative to the concentration used in Round 1. S/B is the signal value (copies DNA selected with beads coated with target protein) divided by the background value (copies DNA selected with beads coated with (His)$_6$ peptide).

B. Library Convergence

Amplification products were evaluated each round for state of sequence convergence using the renaturation assay described previously. Renaturation plots are illustrated in FIG. 10. In this Example, the response of a converged library has a sigmoidal shape with an inflection point value less than 100 seconds and an RFUmax value greater than 60. By these criteria, sufficient convergence occurred during Round 5 for the P-cadherin library and Round 6 for the gp130 library. Round 8 libraries for each protein were chosen for further evaluation.

C. Enriched Library Affinity Measurements

Figure 11A:
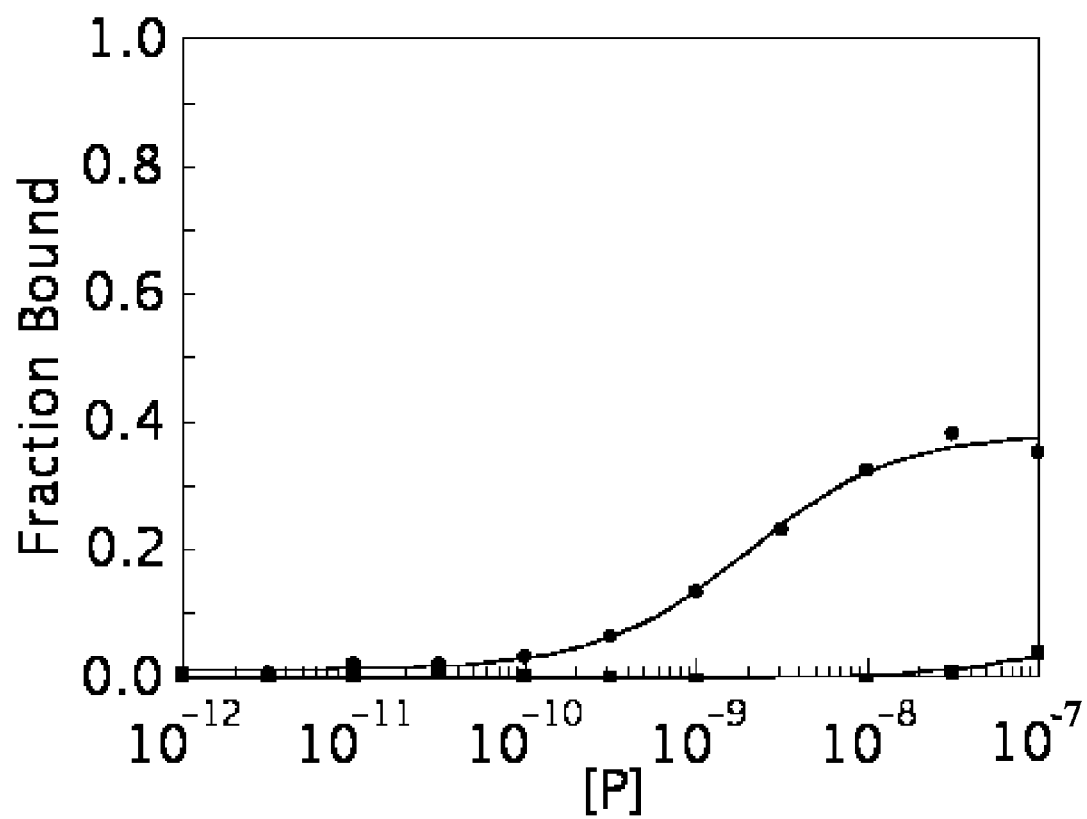
FIGS. 11A and 11B depict equilibrium binding curves for random and enriched libraries. [P] represents protein concentration in molarity.
Figure 11B:
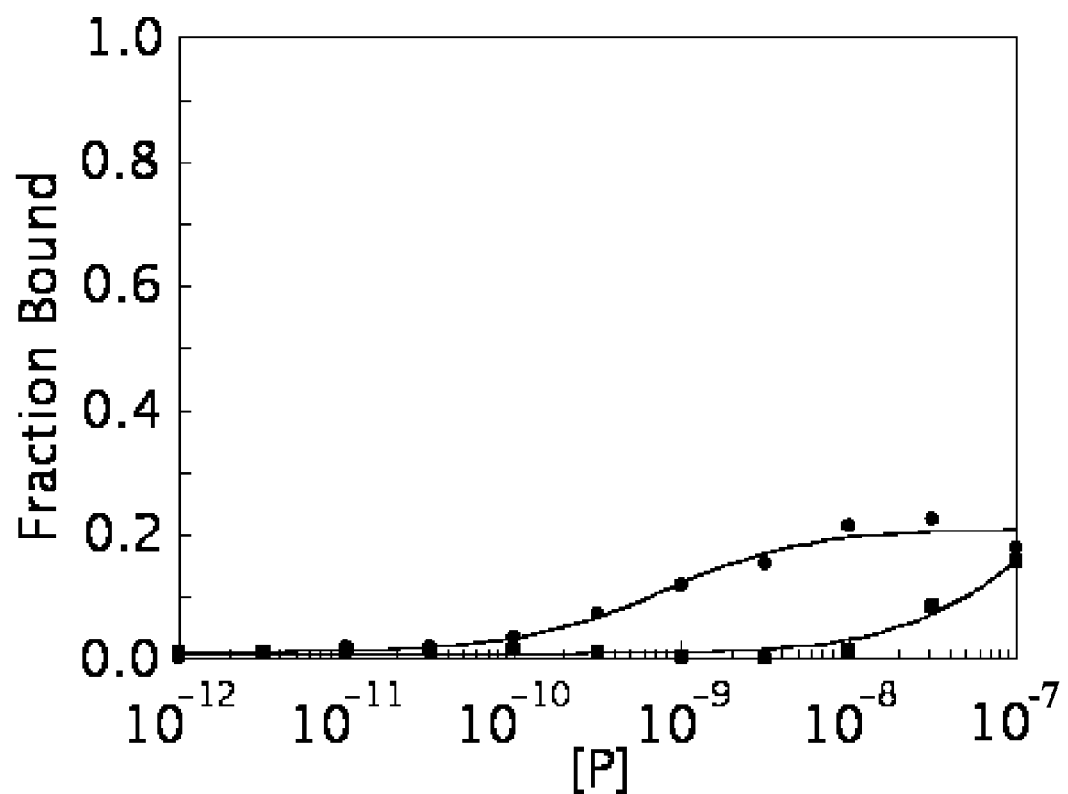

The affinity of each library for its target protein was measured with the TALON bead partition affinity assay described in the methods. The binding responses and calculated equilibrium binding constants ($K_d$) of each library and the starting random library with the equivalent composition are illustrated in FIG. 11. $K_d$ values of the enriched libraries (P-cadherin $K_d$=2.0×10$^{-9}$ M, gp130 $K_d$=7.9×10$^{-10}$ M) were significantly higher than those of the random libraries (P-cadherin $K_d$>1×10$^{-7}$ M, gp130 $K_d$>1×10$^{-7}$ M). These results indicated a high affinity aptamer likely existed in each of these Round 8 libraries.

D. Sequence Analysis

The high affinity libraries were cloned and 32 representatives were sequenced and analyzed as described in the methods. Sequence alignments are illustrated in FIG. 12. Of the 32 isolates sequenced for each library, some existed in multiple copies (noted in the Count column of FIG. 12), while others existed as a single copy. Some isolates shared a common sequence string (boldface) but varied outside of the string, and others had varying positions within a string. Those sharing a common string are considered to be members of a sequence "family" whose string may represent a component necessary for high affinity target binding. Those not sharing a common string are called "orphans" and may or may not have a unique component necessary for high affinity target binding. A multiple copy representative of each family, and any multiple copy orphans were chosen for affinity measurements.

E. Aptamer Affinity Measurements

Figure 13A:
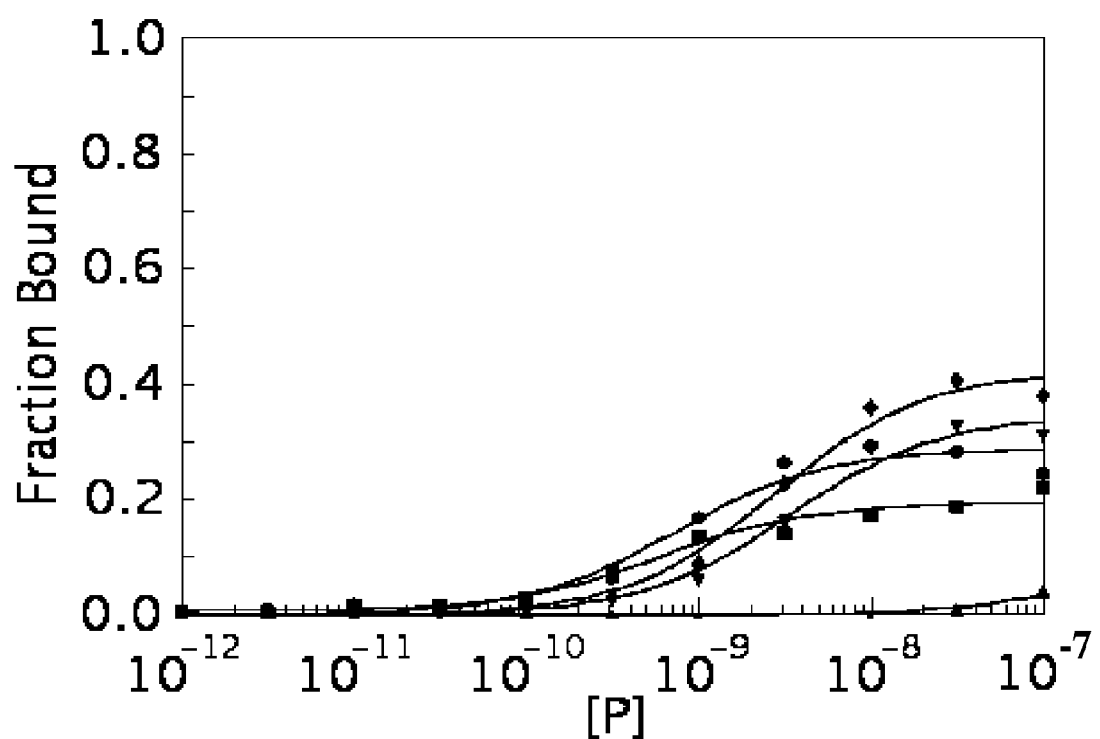
FIGS. 13A and 13B depict equilibrium binding curves for chosen aptamers and a random library. [P] represents the protein concentration in molarity.
Figure 13B:
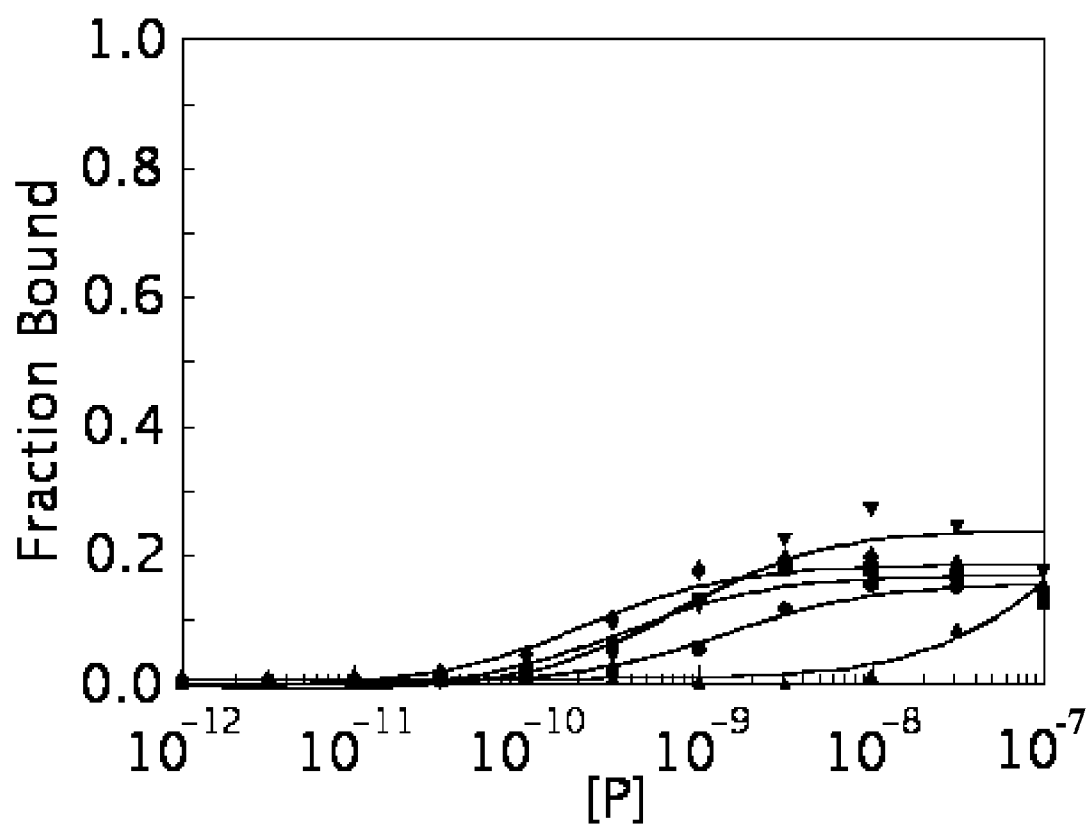

The affinity of each chosen aptamer for its target protein was measured with the TALON bead partition affinity assay described in the methods. Binding responses and calculated equilibrium binding constants ($K_d$) of each chosen aptamer are illustrated in FIG. 13. Of the aptamers tested, the ones with the highest affinity were P-cadherin aptamers 1679-70 ($K_d$=7.24×100 M) and 1679-71 ($K_d$=5.89×100 M) and gp130 aptamers 1704-3 ($K_d$=2.12×100 M) and 1704-12 ($K_d$=3.49×10$^{-10}$ M). These aptamers were chosen for further analysis.

F. Conversion of Aptamer to Photoaptamer

Figure 14A:
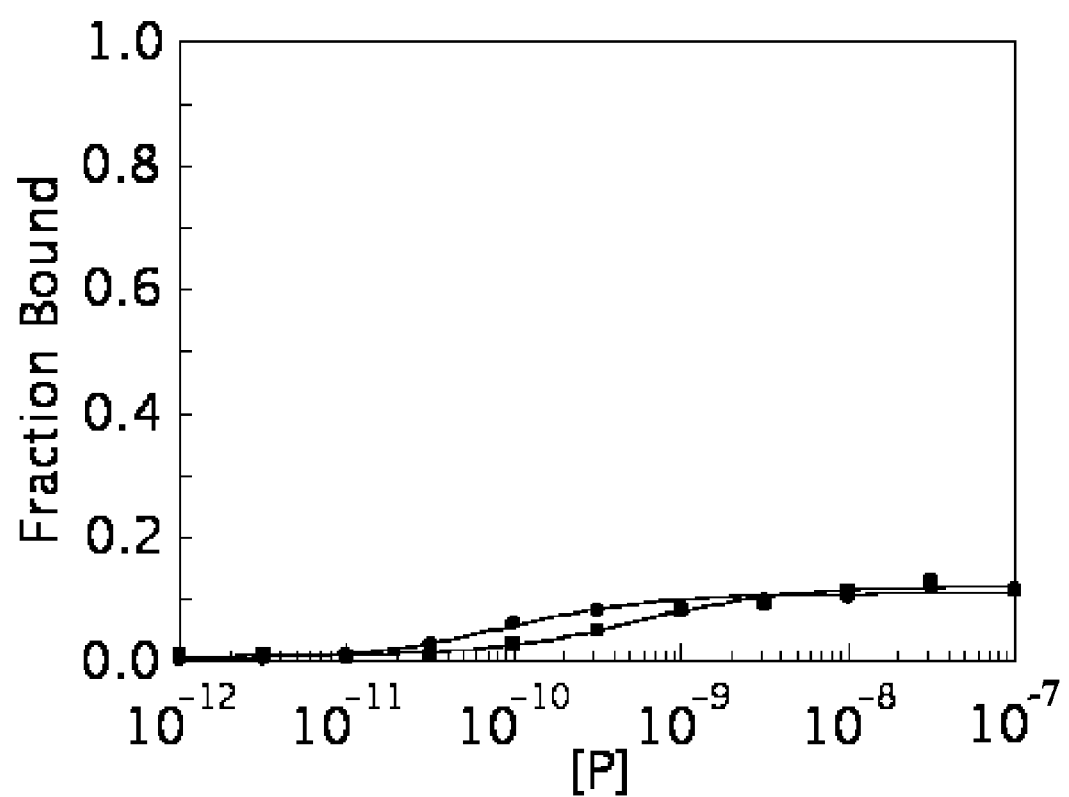
FIGS. 14A, 14B, and 14C depict equilibrium binding curves for 5-MedC and 5-BrdC versions of chosen aptamers. [P] represents the protein concentration in molarity.
Figure 14B:
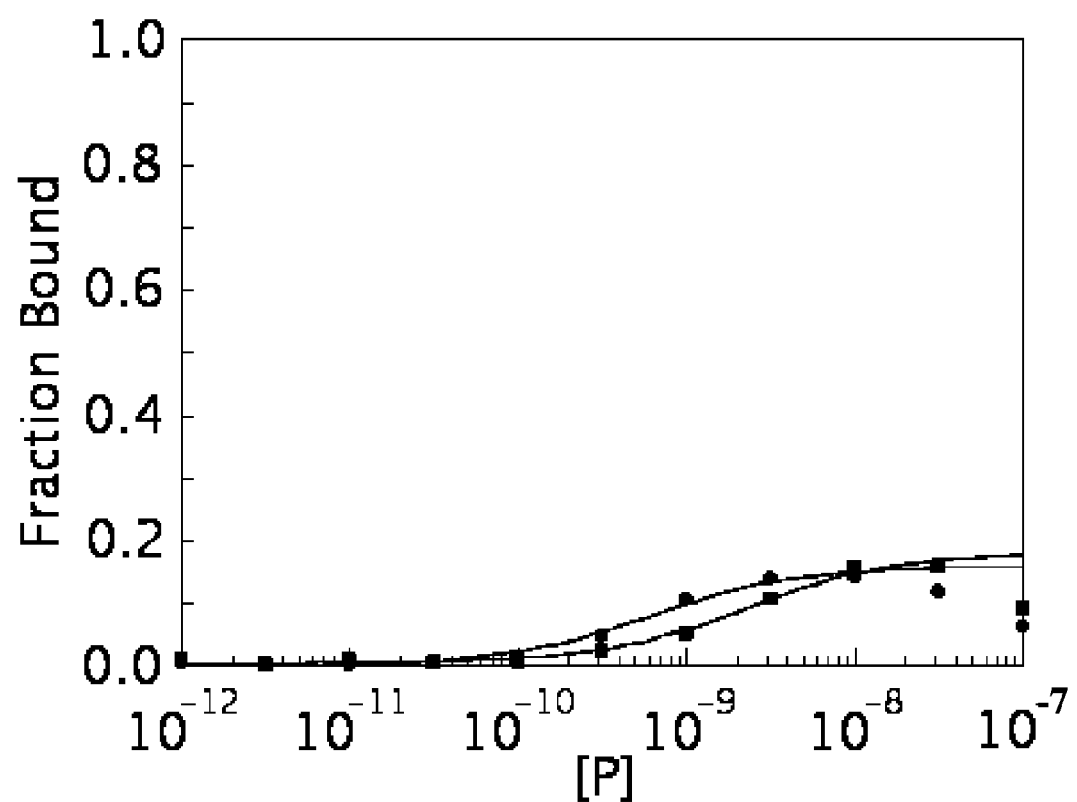
Figure 14C:
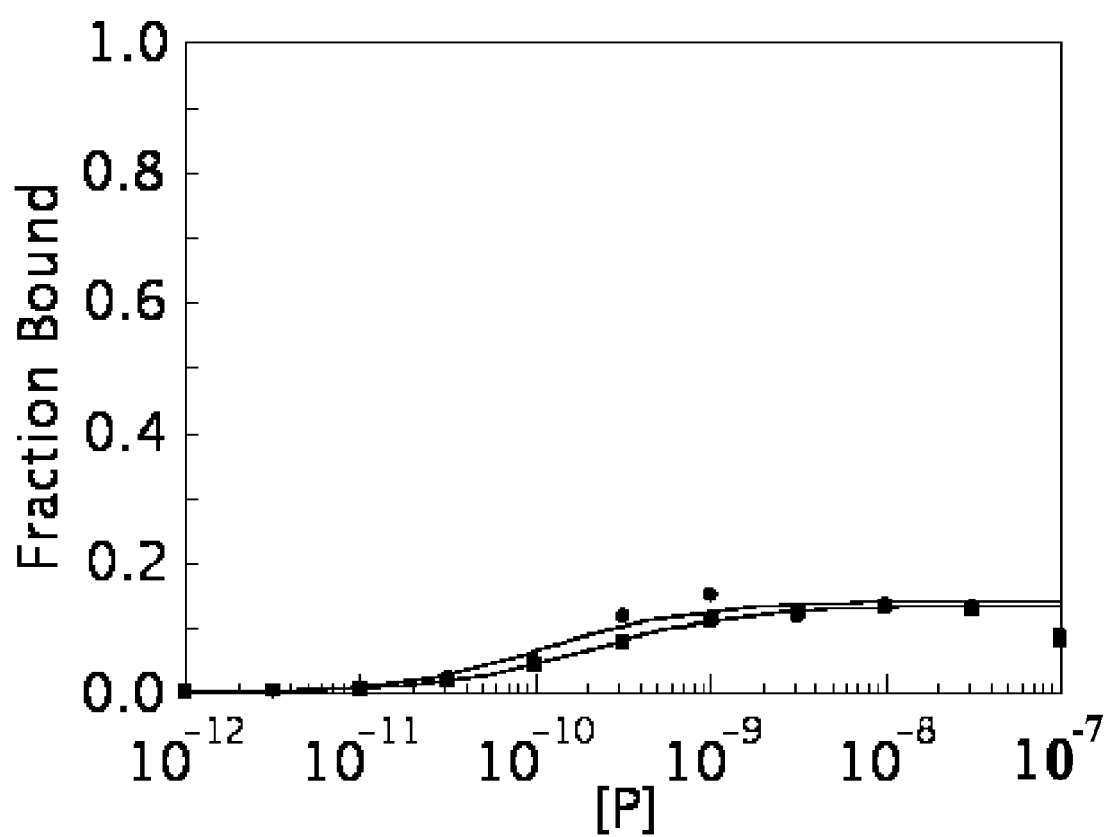
Figure 15:
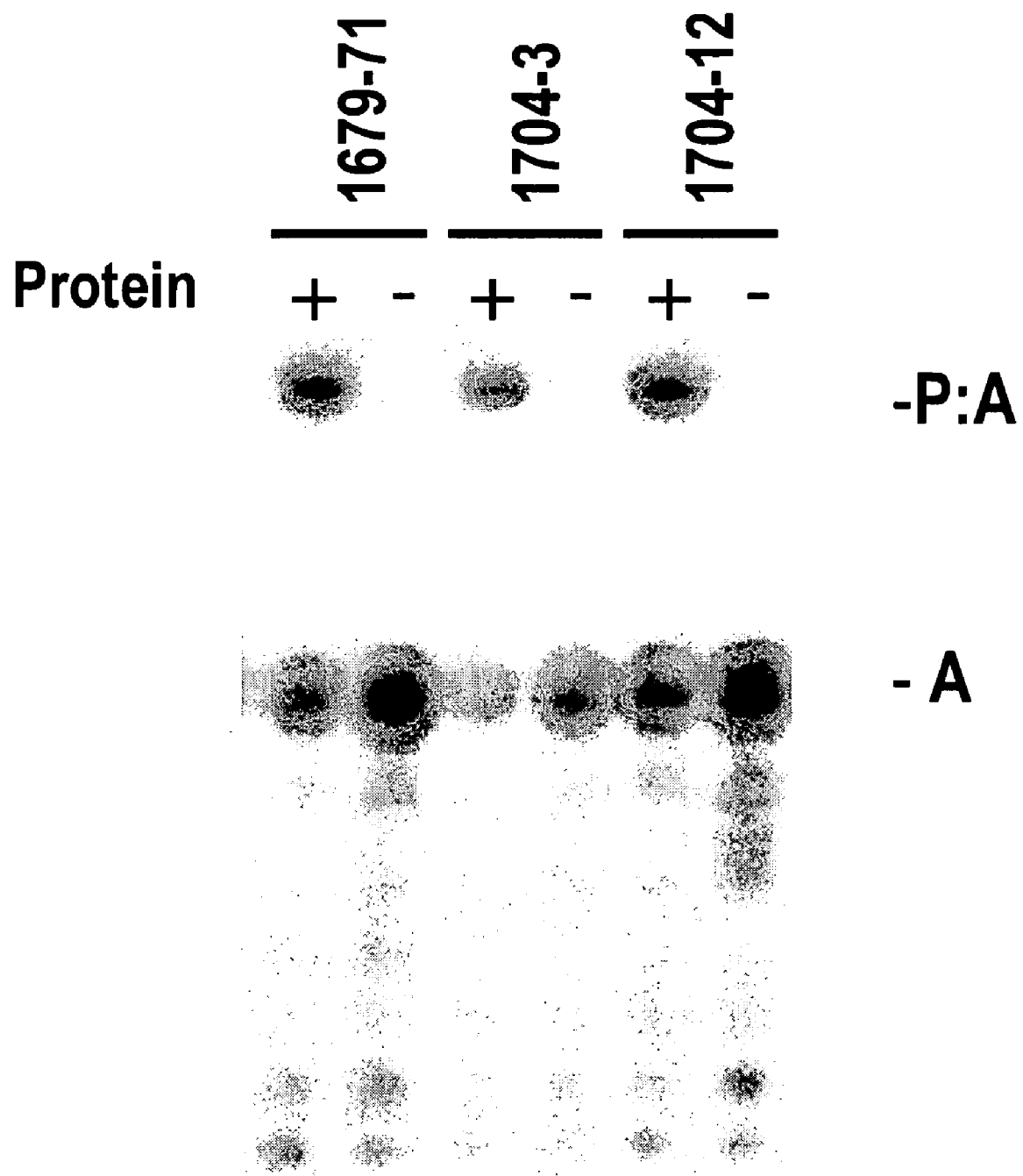
FIG. 15 depicts PAGE analysis of photocrosslink activity of P-cadherin photoaptamer 1679-71 and gp130 aptamers 1704-3 and 1704-12. Covalent protein:aptamer complexes (P:A) migrate slower than free aptamer (A).
Figure 16A:
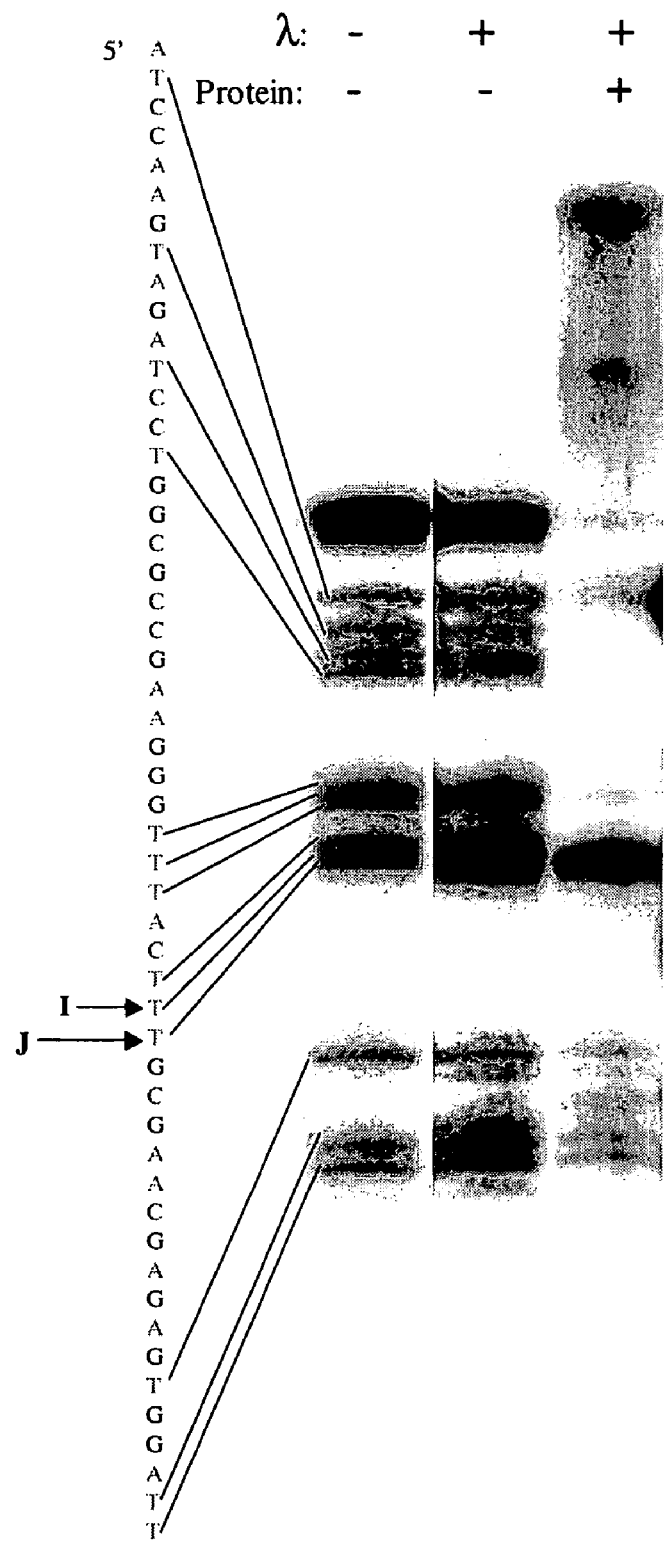
FIGS. 16A-16D depict the identification and substitution of non-photocrosslinking BrdU nucleotides with dT nucleotides in two photoaptamers isolated from candidate mixtures composed of dA, dG, dC, and BrdU.
Figure 16B:
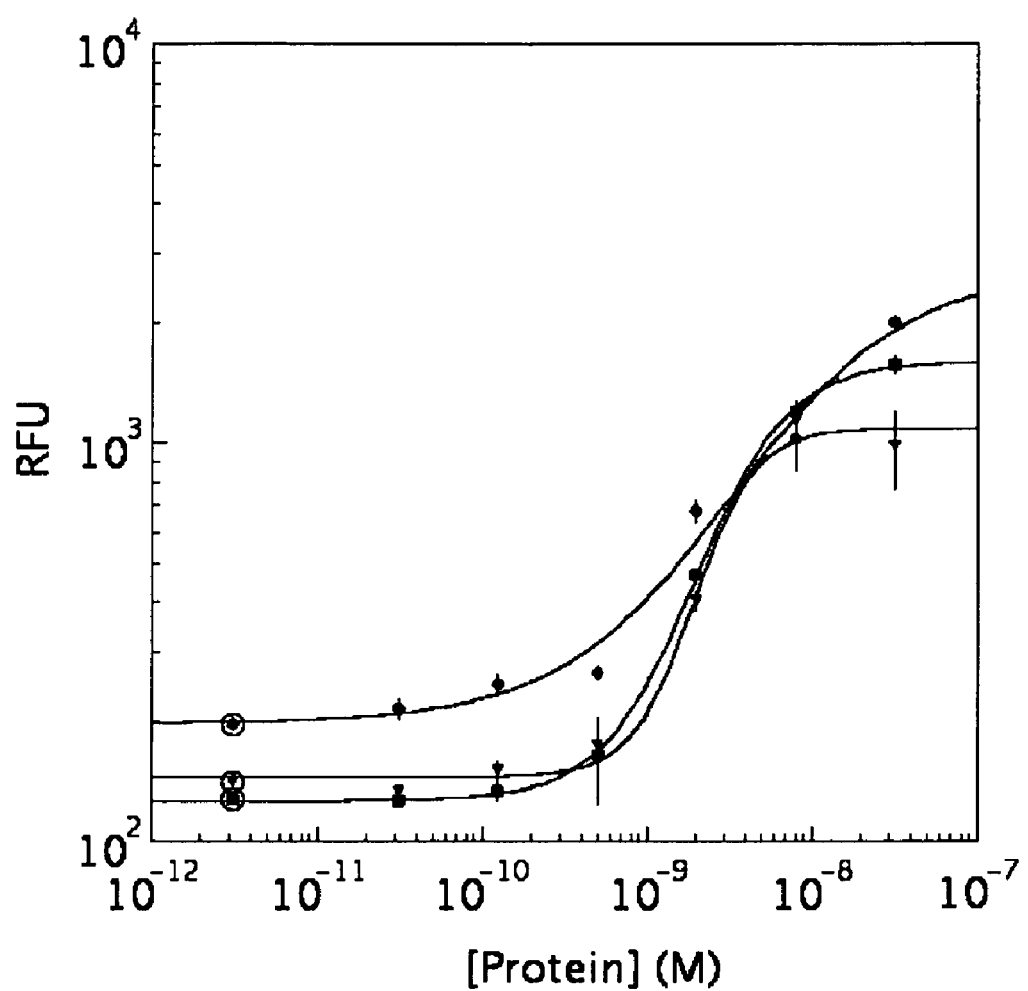
Figure 16C:
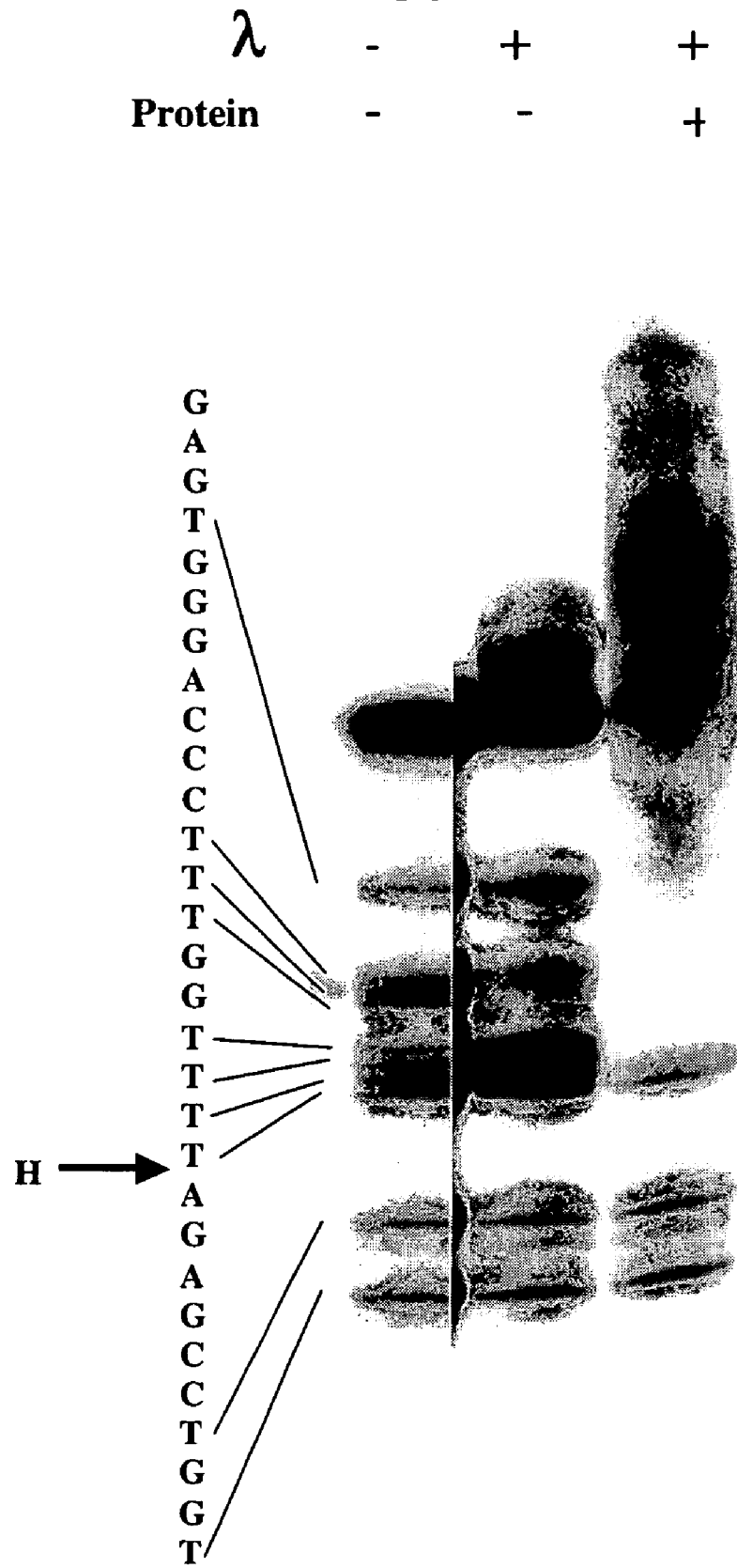
Figure 16D:
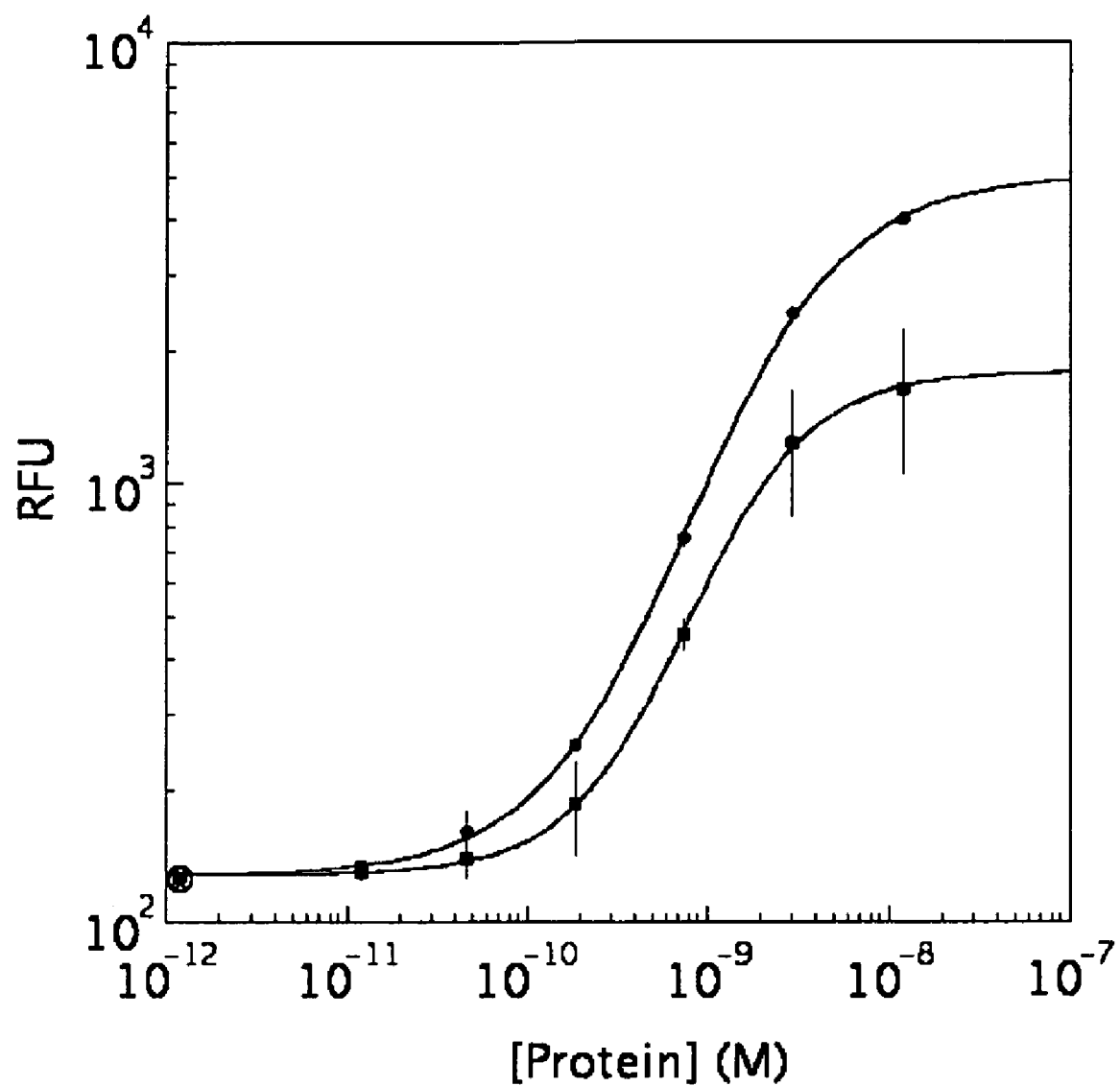

Conversion of a high affinity aptamer to a photoaptamer capable of forming a covalent crosslink with a target protein upon irradiation with 308 nm light is accomplished by replacing every 5-MedC position of the aptamer with 5-BrdC and determining the crosslink activity with the gel crosslink assay described previously. BrdC versions of each candidate aptamer were prepared and purified by PAGE and radiolabeled. To confirm there is no loss in affinity by replacement of 5-MedC with 5-BrdC, both versions were assayed for affinity with the TALON bead partition affinity assay. As illustrated in FIG. 14, very little loss of affinity was observed after 5-BrdC replacement. To determine crosslink activity, candidates were equilibrated with a saturating concentration of target protein and irradiated with 308 nm light. Samples were analyzed by PAGE, where crosslinked protein:aptamer complexes migrate slower than free aptamer, and the percent of total aptamer crosslinked to protein was determined. The results in FIG. 15 indicated 27% of aptamer 1679-71 was crosslinked to P-cadherin, 34% of aptamer 1704-3 was crosslinked to gp130, and 23% of aptamer 1704-12 was crosslinked to gp130 under these conditions.

Example 6

Substitution of Non-Photocrosslinking BrdU Nucleotides with dT

The method for obtaining optimized photoaptamers (reduced non-specific photocrosslinking) involves the substitution of non-photocrosslinking BrdU or BrdC nucleotides with dT or 5-methyl-dC, respectively (in each case, a methyl for bromo substitution), in photoaptamers isolated from candidate DNA mixtures composed of dA, dG, dC, and BrdU, or of dA, dG, 5-methyl-dC, and dT. In the following examples involving two photoaptamers isolated from candidate mixtures composed of dA, dG, dC, and BrdU by an application of photoSELEX, the BrdU position(s) involved in photocrosslinking was identified by the gel mobility shift-based photocrosslink site identification method described previously. Following photocrosslink site identification, the aptamers were chemically synthesized with dT nucleotides in place of all BrdU nucleotides, except for the single positions identified as sites of photocrosslinking. These single BrdU photoaptamer variants were screened, together with the wild-type parental photoaptamers, for target affinity/photocrosslinking. The results shown in FIG. 16 illustrate that the BrdU nucleotides that do not photocrosslink to the target protein in photoaptamers derived from an application of photoSELEX can be replaced with dT nucleotides without a significant loss in affinity or photoreactivity.

Example 7

Displacement of Streptavidin Binding Sequences to Improve Aptamer Selection

A. Preparation of Candidate Mixtures

Candidate mixtures containing dATP, dCTP, dGTP, and BndUTP were prepared by polymerase extension of a primer annealed to a biotinylated template for 94 protein targets. 100 nmoles of biotinylated template was captured with 5 mL 50% slurry of Pierce Ultralink Streptavidin beads, and adjusted to 1M NaCl in a final volume of 15 mL. 100 nmol forward primer in 5 mL Primer Extension Buffer (final 120 mM Tris-HCl, pH 7.8 at 20° C., 10 mM KCl, 6 mM (NH$_4$)$_2$SO$_4$, 7 mM MgSO$_4$, 0.1 mg/mL BSA, 0.1% Triton X-100, 0.25 U/µL KOD XL DNA Polymerase, and 0.5 mM each dATP, dCTP, dGTP, and BndUTP) was added to the slurry and incubated at 70° C. for 120 minutes. Beads were washed three times with 30 mL SB17T Buffer (40 mM HEPES, pH 7.5, 120 mM NaCl, 5 mM KCl, 5 mM MgCl$_2$, 1 mM EDTA, 0.05% TWEEN-20). The aptamer strand was eluted from the beads with 42 mL 20 mM NaOH for 5 minutes with shaking. The eluted strand was neutralized and buffered with 1.2 mL 700 mM HCl, 180 mM HEPES, pH 7.5, 0.45% Tween 20. The extension on the same beads was repeated with a fresh aliquot of the primer extension mixture as necessary to obtain the desired amount of material. Candidate mixtures were concentrated with a Centricon-30, and quantified by UV absorbance spectroscopy. 1 nmol of input candidate DNA mixture was used for each target.

B. Preparation of Target Proteins

Untagged target proteins were biotinylated as described in Example 1.

C. Aptamer Selection with Biotin Washes

Selections were performed with slow off-rate enrichment process as described in Example 1, section C. In addition, selections were repeated starting with the output DNA library after two rounds. Biotin washes to displace aptamers binding directly to the streptavidin beads were incorporated into the repeated selections. After capture of the complexes on streptavidin beads, the beads were washed 2×, 1 minute each, with SB17, 2×, 5 minutes each, with 25 µM biotin in SB17, and finally 2×, 1 minutes each, with SB17. All of the washes were carried out at 37° C.

D. Aptamer Amplification and Purification

Selected aptamer DNA was amplified and purified as described in Example 1.

E. Selection Stringency and Feedback

Target protein was adjusted at each round as described in Example 1. Protein concentration adjustments for two targets as determined by signal to background measurements are shown in Table 4. The increased signal to background observed upon addition of biotin washes was due to decreases in the background signal of aptamers binding to streptavidin beads.

and 31% binding to the streptavidin beads in the absence of protein, respectively. No specific binding to target protein at the concentrations tested was observed for these targets in the streptavidin bead affinity assay. Enriched libraries that had been selected with biotin washes demonstrated much better activity. Binding of the libraries to Gro-α and Protein C exhibited only 1% and 2% binding to the streptavidin beads in the absence of protein, respectively. The enriched library to Gro-α was measured to be $6.4 \times 10^{-10}$ M, and the enriched library to Protein C was measured to be $3.3 \times 10^{-9}$ M. Displacement of streptavidin binding aptamers by biotin resulted in the ability to select high affinity aptamers to these targets.

The foregoing describes various embodiments, aspects, and examples of this disclosure. No particular embodiment, example, or element of a particular embodiment or example is to be construed as a critical, required, or essential element or feature of any of the claims. Further, no element described herein is required for the practice of the methods described herein unless expressly described as "essential" or "critical."

It will be appreciated that various modifications and substitutions can be made to the disclosed embodiments without departing from the scope of the invention as set forth in the claims below. The specification, including the figures and examples, is to be regarded in an illustrative manner, rather than a restrictive one, and all such modifications and substi-

TABLE 4

Relative protein concentrations used in each selection round for each protein target.

| | Gro-α | | | | Protein C | | | |
|---|---|---|---|---|---|---|---|---|
| | No Biotin Washing | | With Biotin Washing | | No Biotin Washing | | With Biotin Washing | |
| Round | P[r] | S/B | P[r] | S/B | P[r] | S/B | P[r] | S/B |
| 1 | 1 | 9.5 | 1 | 9.5 | 1 | 2.6 | 1 | 2.6 |
| 2 | 1 | 2.7 | 1 | 2.7 | 1 | 2.3 | 1 | 2.3 |
| 3 | 1 | 1 | 1 | 4.9 | 1 | 7.1 | 1 | 6.1 |
| 4 | 1 | 1.6 | 1 | 2.8 | 1 | 2 | 1 | 18.4 |
| 5 | 1 | 1 | 1 | 8.2 | 1 | 1 | $3.2 \times 10^{-1}$ | 25.8 |
| 6 | 1 | 2.6 | 1 | 18.3 | 1 | 1 | $1.0 \times 10^{-1}$ | 24.4 |
| 7 | 1 | 1 | $3.2 \times 10^{-1}$ | 27.1 | 1 | 1 | $3.20 \times 10^{-2}$ | 15.5 |
| 8 | 1 | 2.3 | $1.0 \times 10^{-1}$ | 35.1 | 1 | 20.7 | $1.00 \times 10^{-2}$ | 7.5 |

[P]r is the concentration of target protein used in the SELEX round relative to the concentration used in Round 1. S/B is the signal value (copies DNA selected with beads coated with target protein) divided by the background value (copies DNA selected with streptavidin beads).

F. Enriched Library Affinity Measurements

The affinity of each library for its target protein was measured with the streptavidin bead partition affinity assay. In a 60 µL reaction, a low concentration of radiolabeled DNA ($1 \times 10^{-11}$ M mixed with a range of concentrations of target protein ($1 \times 10^{-7}$ M to $1 \times 10^{-12}$ M) in SB17T and incubated for 30 minutes at 37° C. A 5 µL aliquot of each sample, representing ⅛ of the total reaction, was transferred to a nylon membrane and dried. 5.5 µL MyOne Streptavidin beads (10 mg/mL in SB17T) were added to the remaining 55 µL and incubated for 1 minute at 37° C. with constant mixing. 47 µL were passed through a MultiScreen HV Plate under vacuum to separate bound complexes from unbound DNA, and washed with 100 µL SB17T. Both the nylon membrane and MultiScreen HV Plate were phosphorimaged and the amount of radioactivity in each sample was quantified using a FUJI FLA-3000. The fraction of captured DNA was plotted as a function of protein concentration and a non-linear curve-fitting algorithm was used to extract equilibrium binding constants ($K_d$ values) from the data. Without biotin washes, the enriched libraries to Gro-α and Protein C exhibited 13% tutions are intended to be included within the scope of the disclosure. Accordingly, the scope should be determined by the appended claims and their legal equivalents, rather by the examples given above. For example, steps recited in any of the method or process claims can be executed in any feasible order and are not limited to an order presented in any of the embodiments, the examples, or the claims.

A number of patents, patent application publications, and scientific publications are cited throughout and/or listed at the end of the description. Each of these is incorporated herein by reference in their entirety. Likewise, all publications mentioned in an incorporated publication are incorporated by reference in their entirety.

Examples in cited publications and limitations related therewith are intended to be illustrative and not exclusive. Other limitations of the cited publications will become apparent to those of skill in the art upon a reading of the specification and a study of the drawings.

The words "comprise", "comprises", and "comprising" are to be interpreted inclusively rather than exclusively.

What is claimed is:

1. A method for identifying a photoaptamer, the method comprising:

a) preparing a candidate mixture of nucleic acids, wherein each nucleic acid comprises:

i) at least one non-photoreactive placeholding modified pyrimidine; and ii) at least one modified pyrimidine independently selected from the group consisting of the modified pyrimidines having the following structure:

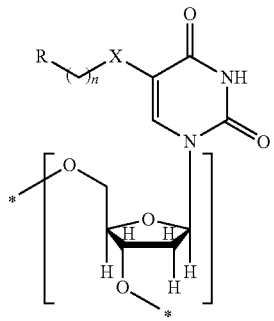

-continued
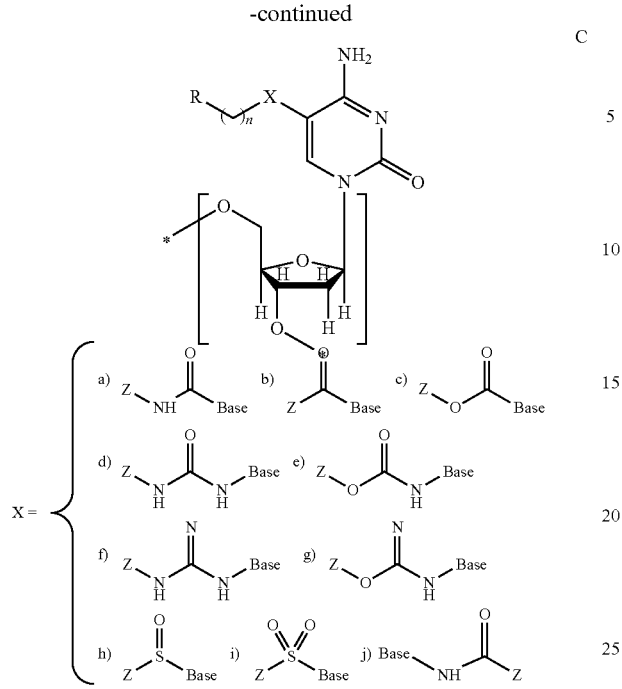
Base = Uridine (U) or Cytidine (C) (attachment is to the 5-position)
Z = R plus $(CH_2)_n$ connecting group, where n = 0-3
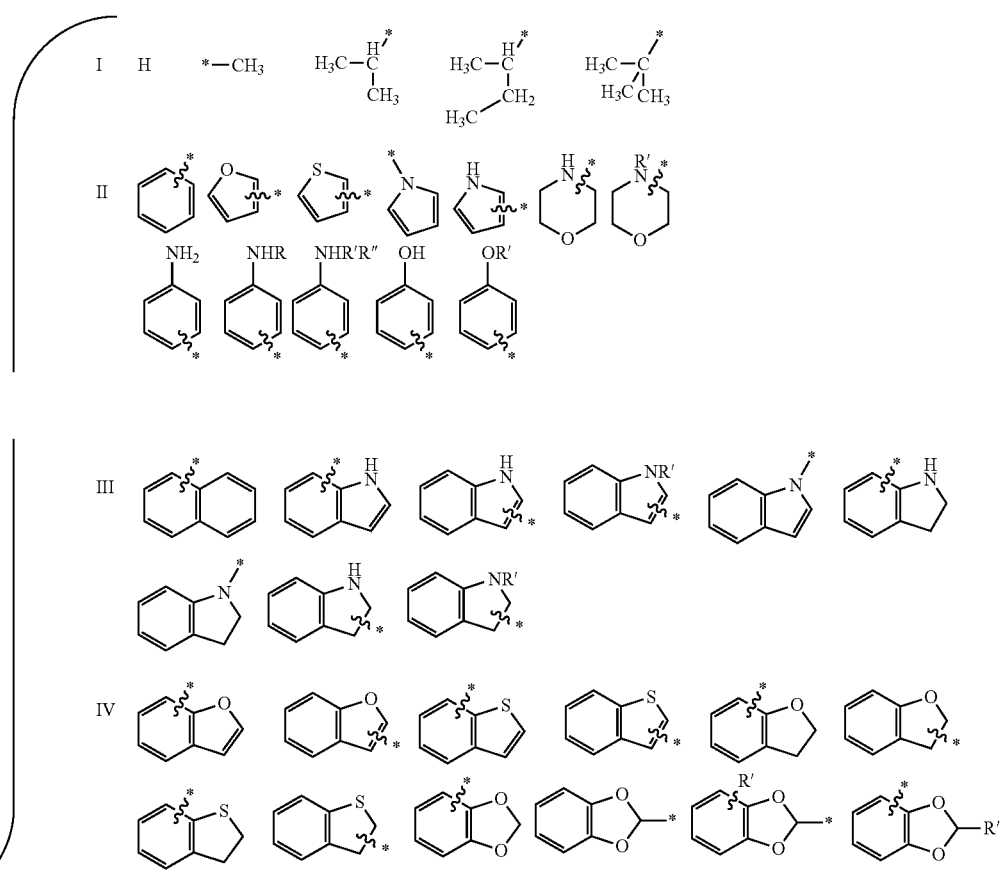

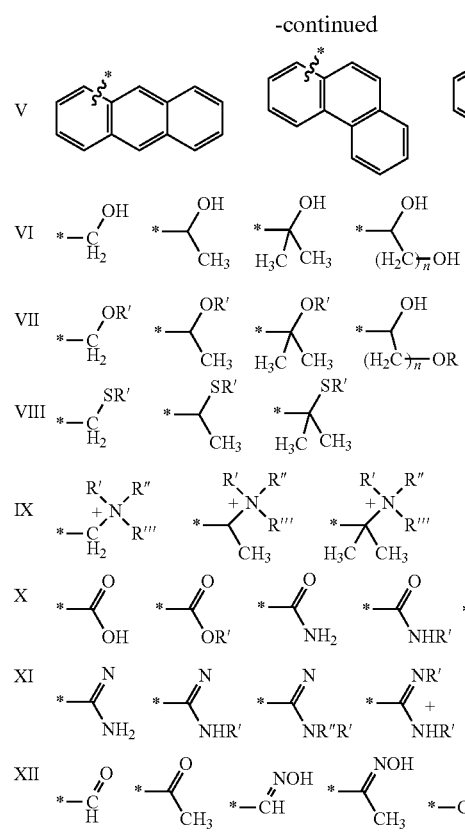

*Denotes point of attachment of the R group to $(CH_2)_n$;

b) contacting the candidate mixture with a target, wherein nucleic acids having an increased affinity to the target relative to the candidate mixture may be partitioned from the remainder of the candidate mixture;
c) partitioning the increased affinity nucleic acids from the remainder of the candidate mixture;
d) amplifying the increased affinity nucleic acids to yield a nucleic acid ligand-enriched mixture of nucleic acids;
e) repeating (b)-(d) as desired;
f) producing from said nucleic acid ligand-enriched mixture of nucleic acids a candidate photoaptamer or a mixture of candidate photoaptamers by replacing in each nucleic acid of the ligand-enriched mixture of nucleic acids one or more non-photoreactive placeholding pyrimidines with a photoreactive pyrimidine;
g) contacting said candidate photoaptamer(s) with said target wherein a candidate photoaptamer-target complex is formed;
h) irradiating said candidate photoaptamer-target complex;
i) determining whether said candidate photoaptamer-target complex has photocrosslinked;
j) repeating (f)-(i) as desired; and
k) identifying at least one photoaptamer to the target.

2. The method of claim 1 wherein said non-photoreactive placeholding modified pyrimidine comprises a methyl group at the C-5 position and said photoreactive pyrimidine comprises a Br or I at the C-5 position.

3. The method of claim 1 wherein said non-photoreactive placeholding modified pyrimidine is 5-methyl-cytosine.

4. The method of claim 1 wherein said non-photoreactive placeholding modified pyrimidine is thymine.

5. The method of claim 1 wherein said photoreactive pyrimidine is 5-Br-cytosine.

6. The method of claim 1 wherein said photoreactive pyrimidine is 5-Br-uracil.

7. A method for identifying a photoaptamer, the method comprising:
a) preparing a candidate mixture of nucleic acids comprising at least one non-photoreactive placeholding modified pyrimidine;
b) contacting the candidate mixture with a target, wherein nucleic acids having an increased affinity to the target relative to the candidate mixture may be partitioned from the remainder of the candidate mixture;
c) partitioning the increased affinity nucleic acids from the remainder of the candidate mixture;
d) amplifying the increased affinity nucleic acids to yield a nucleic acid ligand-enriched mixture of nucleic acids;
e) repeating (b)-(d) as desired;
f) producing from said nucleic acid ligand-enriched mixture of nucleic acids a candidate photoaptamer or a mixture of candidate photoaptamers by replacing in each nucleic acid of the ligand-enriched mixture of nucleic acids one or more non-photoreactive placeholding pyrimidines with a photoreactive pyrimidine;
g) contacting said candidate photoaptamer(s) with said target wherein a candidate photoaptamer-target complex is formed;

h) irradiating said candidate photoaptamer-target complex;
i) determining whether said candidate photoaptamer-target complex has photocrosslinked;
j) repeating (f)-(i) as desired; and
k) identifying at least one photoaptamer to the target.

8. A method for identifying an aptamer, the method comprising:
   a) preparing a candidate mixture of nucleic acids;
   b) contacting the candidate mixture with a biotinylated target molecule, wherein nucleic acids having an increased affinity to the target molecule relative to other nucleic acids in the candidate mixture bind the target molecule, forming nucleic acid-target molecule complexes;
   c) partitioning the nucleic acid-target molecule complexes from the candidate mixture by contacting the candidate mixture with a solid support having streptavidin bound to the solid support and washing the solid support with a solution containing biotin;
   d) dissociating the nucleic acid-target molecule complexes to form free nucleic acids;
   e) amplifying the free nucleic acids to yield a mixture of nucleic acids enriched with nucleic acids that are capable of binding to the target molecule with increased affinity;
   f) repeating (b) through (e) as desired; and
   g) identifying at least one aptamer to the target molecule.

9. The method of claim 7 wherein said non-photoreactive placeholding modified pyrimidine comprises a methyl group at the C-5 position and said photoreactive pyrimidine comprises a Br or I at the C-5 position.

10. The method of claim 7 wherein said non-photoreactive placeholding modified pyrimidine is 5-methyl-cytosine.

11. The method of claim 7 wherein said non-photoreactive placeholding modified pyrimidine is thymine.

12. The method of claim 7 wherein said photoreactive pyrimidine is 5-Br-cytosine.

13. The method of claim 7 wherein said photoreactive pyrimidine is 5-Br-uracil.

* * * * *

SEQUENCE LISTING

<160> NUMBER OF SEQ ID NOS: 44

<210> SEQ ID NO 1
<211> LENGTH: 76
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(4)
<223> OTHER INFORMATION: T is dT-biotin
<220> FEATURE:
<221> NAME/KEY: misc_feature
<222> LOCATION: (20)..(59)
<223> OTHER INFORMATION: N = a, c, g, t

<400> SEQUENCE: 1
atatcccgct cgtcgtctgn nnnnnnnnnn nnnnnnnnnn nnnnnnnnnn nnnnnnnnnc    60
aggcagacgg tcactc                                                    76

<210> SEQ ID NO 2
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: U is 5-bromodeoxyuracil, 4-azido-2-nitro-
      aniline, anthraquinone, or psoralen
<220> FEATURE:
<221> NAME/KEY: misc_feature
<222> LOCATION: (1)..(26)
<223> OTHER INFORMATION: DNA/RNA mixture

<400> SEQUENCE: 2
uatatatatg agtgaccgtc tgcctg                                         26

<210> SEQ ID NO 3
<211> LENGTH: 25
<212> TYPE: DNA
<213> ORGANISM: Artificial
<220> FEATURE:
<223> OTHER INFORMATION: Synthetic

<400> SEQUENCE: 3
atatatatga gtgaccgtct gcctg                                          25

<210> SEQ ID NO 4
<211> LENGTH: 23
<212> TYPE: DNA
<213> ORGANISM: Artificial
<220> FEATURE:
<223> OTHER INFORMATION: Synthetic

<400> SEQUENCE: 4 tttttttttcc cgctcgtcgt ctg                                           23

<210> SEQ ID NO 5
<211> LENGTH: 27
<212> TYPE: DNA
<213> ORGANISM: Artificial
<220> FEATURE:
<223> OTHER INFORMATION: Synthetic
<220> FEATURE:
<221> NAME/KEY: misc_feature

```
<222> LOCATION: (2)..(4)
<223> OTHER INFORMATION: T is dT-biotin

<400> SEQUENCE: 5
atattttttt ttcccgctcg tcgtctg                                          27

<210> SEQ ID NO 6
<211> LENGTH: 79
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (2)..(4)
<223> OTHER INFORMATION: T is dT-biotin
<220> FEATURE:
<221> NAME/KEY: misc_feature
<222> LOCATION: (23)..(62)
<223> OTHER INFORMATION: N = a, c, g, t

<400> SEQUENCE: 6
atatgtgtct gtctgtgtcc tcnnnnnnnn nnnnnnnnnn nnnnnnnnnn nnnnnnnnnn      60
nnggtggagt gtggtgagg                                                  79

<210> SEQ ID NO 7
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1)
<223> OTHER INFORMATION: U is 5-bromodeoxyuracil, 4-azido-2-nitro-
      aniline, anthraquinone, psoralen
<220> FEATURE:
<221> NAME/KEY: misc_feature
<222> LOCATION: (1)..(26)
<223> OTHER INFORMATION: DNA/RNA mixture

<400> SEQUENCE: 7
uatatatatc ctcaccacac tccacc                                           26

<210> SEQ ID NO 8
<211> LENGTH: 25
<212> TYPE: DNA
<213> ORGANISM: Artificial
<220> FEATURE:
<223> OTHER INFORMATION: Synthetic

<400> SEQUENCE: 8
atatatatcc tcaccacact ccacc                                            25

<210> SEQ ID NO 9
<211> LENGTH: 26
<212> TYPE: DNA
<213> ORGANISM: Artificial
<220> FEATURE:
<223> OTHER INFORMATION: Synthetic

<400> SEQUENCE: 9
ttttttttgt gtctgtctgt gtcctc                                           26

<210> SEQ ID NO 10
<211> LENGTH: 30
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (2)..(4)
<223> OTHER INFORMATION: T is dT-biotin

<400> SEQUENCE: 10 atatttttt ttgtgtctgt ctgtgtcctc                                       30

<210> SEQ ID NO 11
<211> LENGTH: 81
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(81)
<223> OTHER INFORMATION: U is 5-benzyl-dU
<220> FEATURE:
<221> NAME/KEY: misc_feature
<222> LOCATION: (1)..(81)
<223> OTHER INFORMATION: DNA/RNA mixture
<220> FEATURE:
<221> NAME/KEY: misc_feature
<222> LOCATION: (8)..(8)
<223> OTHER INFORMATION: T is 5'- 4-Azido-2-nitro-aniline (ANA)

<400> SEQUENCE: 11
atatatatga gtgaccgtct gcctgagctg cgguugauga uauacuucgc uuucacugcu      60
cacaccagac gacgagcggg a                                               81

<210> SEQ ID NO 12
<211> LENGTH: 65
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(65)
<223> OTHER INFORMATION: U is 5-benzyl-dU
<220> FEATURE:
<221> NAME/KEY: misc_feature
<222> LOCATION: (1)..(65)
<223> OTHER INFORMATION: DNA/RNA mixture
<220> FEATURE:
<221> NAME/KEY: misc_feature
<222> LOCATION: (8)..(8)
<223> OTHER INFORMATION: T is 5' - 4-Azido-2-nitro-aniline (ANA)

<400> SEQUENCE: 12
atatatatga gtgaccgtct gcctgagctg cgguugauga uauacuucgc uuucacugcu      60
cacac                                                                 65

<210> SEQ ID NO 13
<211> LENGTH: 24
<212> TYPE: DNA
<213> ORGANISM: Artificial
<220> FEATURE:
<223> OTHER INFORMATION: Synthetic

<400> SEQUENCE: 13
tttttttttc ccgctcgtcg tctg                                            24

<210> SEQ ID NO 14
<211> LENGTH: 33
<212> TYPE: DNA
<213> ORGANISM: Artificial
<220> FEATURE:
```

```
<223> OTHER INFORMATION: Synthetic
<220> FEATURE:
<221> NAME/KEY: misc_feature
<222> LOCATION: (1)..(33)
<223> OTHER INFORMATION: T is 5-benzyl-dU

<400> SEQUENCE: 14
ccgtatgccg ccgtcggcgt tttaagacct tag                                33

<210> SEQ ID NO 15
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: T is 5-benzyl-dU
<220> FEATURE:
<221> NAME/KEY: misc_feature
<222> LOCATION: (1)..(2)
<223> OTHER INFORMATION: C is 5-bromo-dC

<400> SEQUENCE: 15
ccgtatgccg ccgtcggcgt tttaagacct tag                                33

<210> SEQ ID NO 16
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: T is 5-benzyl-dU
<220> FEATURE:
<221> NAME/KEY: misc_feature
<222> LOCATION: (8)..(9)
<223> OTHER INFORMATION: C is 5-bromo-dC

<400> SEQUENCE: 16
ccgtatgccg ccgtcggcgt tttaagacct tag                                33

<210> SEQ ID NO 17
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: T is 5-benzyl-dU
<220> FEATURE:
<221> NAME/KEY: misc_feature
<222> LOCATION: (11)..(12)
<223> OTHER INFORMATION: C is 5-bromo-dC

<400> SEQUENCE: 17
ccgtatgccg ccgtcggcgt tttaagacct tag                                33

<210> SEQ ID NO 18
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
```

```
<223> OTHER INFORMATION: T is 5-benzyl-dU
<220> FEATURE:
<221> NAME/KEY: misc_feature
<222> LOCATION: (15)..(15)
<223> OTHER INFORMATION: C is 5-bromo-dC
<220> FEATURE:
<221> NAME/KEY: misc_feature
<222> LOCATION: (18)..(18)
<223> OTHER INFORMATION: C is 5-bromo-dC

<400> SEQUENCE: 18
ccgtatgccg ccgtcggcgt tttaagacct tag                                33

<210> SEQ ID NO 19
<211> LENGTH: 33
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(33)
<223> OTHER INFORMATION: T is 5-benzyl-dU
<220> FEATURE:
<221> NAME/KEY: misc_feature
<222> LOCATION: (28)..(29)
<223> OTHER INFORMATION: C is 5-bromo-dC

<400> SEQUENCE: 19
ccgtatgccg ccgtcggcgt tttaagacct tag                                33

<210> SEQ ID NO 20
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 20
tcgtctatat atttacagtg tgggccgtgc tgccacgagg                         40

<210> SEQ ID NO 21
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 21
gagaggctct gatatattta cgtagtctgc gagaccagtc                         40

<210> SEQ ID NO 22
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 22
```
tgagcgcggg ggattgacca atatcgtatg atacgggtgg                    40

<210> SEQ ID NO 23
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 23
atcatgggct tgattggcaa catatcgtat gatacgtgca                    40

<210> SEQ ID NO 24
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(39)
<223> OTHER INFORMATION: T is 5' - tryptamino - dU

<400> SEQUENCE: 24
ctgacgacgt tcggtattca tcttccaata ccacgcggg                     39

<210> SEQ ID NO 25
<211> LENGTH: 38
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(38)
<223> OTHER INFORMATION: T is 5' - tryptamino - dU

<400> SEQUENCE: 25
tcggaggggg atctgcctgg cttgctacgc gcggtcgt                      38

<210> SEQ ID NO 26
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 26
taccttgaaa ggggacatga tgccttcgta tcgggttcgc                    40

<210> SEQ ID NO 27
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 27
cgcattgcca actgatatga tccaacagcc ttgtacgtga                                40

<210> SEQ ID NO 28
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 28
gtgtggaggg ctgcggtagg gagcatcagt agccgggtgg                                40

<210> SEQ ID NO 29
<211> LENGTH: 39
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(30)
<223> OTHER INFORMATION: T is 5' - tryptamino - dU

<400> SEQUENCE: 29
gggtcggtgg tgtgggtgg gtgggtgggc ttctgtgat                                  39

<210> SEQ ID NO 30
<211> LENGTH: 41
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(41)
<223> OTHER INFORMATION: T is 5' - tryptamino - dU

<400> SEQUENCE: 30
tgcctgaggc gcgtcttaga tccatttcga gttagggcgg t                              41

<210> SEQ ID NO 31
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 31
tggtacagct cttggatcca tttcgagtta gggcccccgg                                40

<210> SEQ ID NO 32
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 32

```
ggcctatgcg tgggtgattt gaagggcggc tggtcggtag                              40

<210> SEQ ID NO 33
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 33
gctggggtag gctgggggt cgctggtcgg ggtgggcggg                               40

<210> SEQ ID NO 34
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 34
gcggtaggta gagttagggg ggtggctggt cggttgcgct                              40

<210> SEQ ID NO 35
<211> LENGTH: 36
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(36)
<223> OTHER INFORMATION: T is 5' - tryptamino - dU

<400> SEQUENCE: 35
ggcgcttgca tccattcgtt tagcgcaagg gctcag                                  36

<210> SEQ ID NO 36
<211> LENGTH: 26
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(26)
<223> OTHER INFORMATION: T is 5' - tryptamino - dU

<400> SEQUENCE: 36
cggcttggat ccattcgttt agtggg                                             26

<210> SEQ ID NO 37
<211> LENGTH: 40
<212> TYPE: DNA
<213> ORGANISM: Artificial
<220> FEATURE:
<223> OTHER INFORMATION: Synthetic
<220> FEATURE:
```

<221> NAME/KEY: misc_feature
<222> LOCATION: (1)..(40)
<223> OTHER INFORMATION: T is 5' - tryptamino - dU

<400> SEQUENCE: 37
accaacccgc tttgatccat tagtttagcg cctaggtggg                             40

<210> SEQ ID NO 38
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 38
gtagtaagcg gattcattaa ctgtctcatc cctgactgag                             40

<210> SEQ ID NO 39
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 39
ggtcggcgat ttgcggcgct tgatgaaggg tttagccccc                             40

<210> SEQ ID NO 40
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 40
tatttgggag gattcctaac cctatgtcca actcggccca                             40

<210> SEQ ID NO 41
<211> LENGTH: 40
<212> TYPE: DNA
<213> ORGANISM: Artificial
<220> FEATURE:
<223> OTHER INFORMATION: Synthetic
<220> FEATURE:

```
<221> NAME/KEY: misc_feature
<222> LOCATION: (1)..(40)
<223> OTHER INFORMATION: T is 5' - tryptamino - dU

<400> SEQUENCE: 41
taactagtta cgactgttgg aaccctttgg cggcactgca                              40

<210> SEQ ID NO 42
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 42
tctatcgtgt ttgattggtg cgctgcattg gcaggacgcg                              40

<210> SEQ ID NO 43
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 43
gtaaggggat tgcaccagtt gaggcctttt ggggtggcgg                              40

<210> SEQ ID NO 44
<211> LENGTH: 40
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(40)
<223> OTHER INFORMATION: T is 5' - tryptamino - dU

<400> SEQUENCE: 44
aagggcaggc atggagctgt cggtaagcta ggtttggcca                              40
```